United States Patent
Hofstadler et al.

(10) Patent No.: US 9,023,655 B2
(45) Date of Patent: *May 5, 2015

(54) SAMPLE PROCESSING UNITS, SYSTEMS, AND RELATED METHODS

(71) Applicant: IBIS Biosciences, Inc., Carlsbad, CA (US)

(72) Inventors: Steven A. Hofstadler, Vista, CA (US); Jared J. Drader, San Marcos, CA (US); Jose R. Gutierrez, San Marcos, CA (US); Paul J. Gleason, Laguna Niguel, CA (US); Rex O. Bare, Preston, CT (US); Robert D. Miller, Costa Mesa, CA (US); Jeffrey C. Smith, Irvine, CA (US)

(73) Assignee: IBIS Biosciences, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/102,200

(22) Filed: Dec. 10, 2013

(65) Prior Publication Data

US 2014/0224042 A1    Aug. 14, 2014

Related U.S. Application Data

(63) Continuation of application No. 13/595,189, filed on Aug. 27, 2012, now Pat. No. 8,609,430, which is a (Continued)

(51) Int. Cl.
*G01N 1/10*    (2006.01)
*G01N 1/00*    (2006.01)

(Continued)

(52) U.S. Cl.
CPC .. *G01N 1/10* (2013.01); *G01N 1/02* (2013.01); *G01N 35/0098* (2013.01); *G01N 35/025* (2013.01); *G01N 2035/00524* (2013.01)

(58) Field of Classification Search
CPC ............ G01N 35/0092; G01N 35/025; G01N 2035/00524

USPC ............ 436/149, 150, 94, 93, 91; 422/63, 64, 422/65, 50

See application file for complete search history.

(56) References Cited

U.S. PATENT DOCUMENTS

| | | | |
|---|---|---|---|
| 4,075,475 | A | 2/1978 | Risby et al. |
| 4,683,195 | A | 7/1987 | Mullis et al. |

(Continued)

FOREIGN PATENT DOCUMENTS

| | | | |
|---|---|---|---|
| DE | 19732086 | A1 | 1/1999 |
| DE | 19802905 | A1 | 7/1999 |

(Continued)

OTHER PUBLICATIONS

Aaserud D.J., et al., "Accurate Base Composition of Double-Strand DNA by Mass Spectrometry," American Society for Mass Spectrometry, 1996, vol. 7 (12), pp. 1266-1269.

(Continued)

*Primary Examiner* — Christine T Mui
(74) *Attorney, Agent, or Firm* — Casimir Jones, S.C.; Wi Middleton

(57) ABSTRACT

Sample processing units useful for mixing and purifying materials, such as fluidic materials are provided. A sample processing unit typically includes a container configured to contain a sample comprising magnetically responsive particles, and one or more magnets that are in substantially fixed positions relative to the container. A sample processing unit also generally includes a conveyance mechanism configured to convey the container to and from a position that is within magnetic communication with the magnet, e.g., such that magnetically responsive particles with captured analytes can be retained within the container when other materials are added to and/or removed from the container. Further, a sample processing unit also typically includes a rotational mechanism that is configured to rotate the container, e.g., to effect mixing of sample materials disposed within the container. Related carrier mechanisms, sample processing stations, systems, and methods are also provided.

19 Claims, 27 Drawing Sheets

Related U.S. Application Data continuation of application No. 13/221,608, filed on Aug. 30, 2011, now Pat. No. 8,252,599, which is a continuation of application No. 12/561,175, filed on Sep. 16, 2009, now Pat. No. 8,148,163.

(60) Provisional application No. 61/097,525, filed on Sep. 16, 2008.

(51) Int. Cl.
  *G01N 1/02* (2006.01)
  *G01N 35/00* (2006.01)
  *G01N 35/02* (2006.01)

(56) References Cited

U.S. PATENT DOCUMENTS

| | | |
|---|---|---|
| 4,683,202 A | 7/1987 | Mullis |
| 4,965,188 A | 10/1990 | Mullis et al. |
| 5,015,845 A | 5/1991 | Allen et al. |
| 5,072,115 A | 12/1991 | Zhou |
| 5,143,905 A | 9/1992 | Sivasubramanian et al. |
| 5,213,961 A | 5/1993 | Bunn et al. |
| 5,219,727 A | 6/1993 | Wang et al. |
| 5,288,611 A | 2/1994 | Kohne |
| 5,436,129 A | 7/1995 | Stapleton |
| 5,451,500 A | 9/1995 | Stapleton |
| 5,472,843 A | 12/1995 | Milliman |
| 5,476,774 A | 12/1995 | Wang et al. |
| 5,484,908 A | 1/1996 | Froehler et al. |
| 5,502,177 A | 3/1996 | Matteucci et al. |
| 5,503,980 A | 4/1996 | Cantor |
| 5,504,327 A | 4/1996 | Sproch et al. |
| 5,504,329 A | 4/1996 | Mann et al. |
| 5,523,217 A | 6/1996 | Lupski et al. |
| 5,527,669 A | 6/1996 | Resnick et al. |
| 5,527,675 A | 6/1996 | Coull et al. |
| 5,547,835 A | 8/1996 | Koster |
| 5,567,587 A | 10/1996 | Kohne |
| 5,576,204 A | 11/1996 | Blanco et al. |
| 5,580,733 A | 12/1996 | Levis et al. |
| 5,605,798 A | 2/1997 | Koster |
| 5,608,217 A | 3/1997 | Franzen et al. |
| 5,612,179 A | 3/1997 | Simons |
| 5,622,824 A | 4/1997 | Koster |
| 5,625,184 A | 4/1997 | Vestal et al. |
| 5,639,606 A | 6/1997 | Willey |
| 5,641,632 A | 6/1997 | Kohne |
| 5,645,985 A | 7/1997 | Froehler et al. |
| 5,683,869 A | 11/1997 | Ramsay Shaw et al. |
| 5,686,242 A | 11/1997 | Bruice et al. |
| 5,691,141 A | 11/1997 | Koster |
| 5,700,642 A | 12/1997 | Monforte et al. |
| 5,702,895 A | 12/1997 | Matsunaga et al. |
| 5,707,802 A | 1/1998 | Sandhu et al. |
| 5,712,125 A | 1/1998 | Uhlen |
| 5,716,825 A | 2/1998 | Hancock et al. |
| 5,727,202 A | 3/1998 | Kucala |
| 5,745,751 A | 4/1998 | Nelson et al. |
| 5,747,246 A | 5/1998 | Pannetier et al. |
| 5,747,251 A | 5/1998 | Carson et al. |
| 5,753,467 A | 5/1998 | Jensen et al. |
| 5,753,489 A | 5/1998 | Kistner et al. |
| 5,759,771 A | 6/1998 | Tilanus |
| 5,763,169 A | 6/1998 | Sandhu et al. |
| 5,763,588 A | 6/1998 | Matteucci et al. |
| 5,770,367 A | 6/1998 | Southern et al. |
| 5,770,461 A | 6/1998 | Sakazume et al. |
| 5,777,324 A | 7/1998 | Hillenkamp |
| 5,814,442 A | 9/1998 | Natarajan et al. |
| 5,822,824 A | 10/1998 | Dion |
| 5,828,062 A | 10/1998 | Jarrell et al. |
| 5,830,653 A | 11/1998 | Froehler et al. |
| 5,830,655 A | 11/1998 | Monforte et al. |
| 5,830,853 A | 11/1998 | Backstrom et al. |
| 5,832,489 A | 11/1998 | Kucala |
| 5,834,255 A | 11/1998 | Van Gemen et al. |
| 5,845,174 A | 12/1998 | Yasui et al. |
| 5,849,492 A | 12/1998 | Rogan |
| 5,849,497 A | 12/1998 | Steinman |
| 5,849,901 A | 12/1998 | Mabilat et al. |
| 5,851,765 A | 12/1998 | Koster |
| 5,856,174 A | 1/1999 | Lipshutz et al. |
| 5,864,137 A | 1/1999 | Becker et al. |
| 5,866,429 A | 2/1999 | Bloch |
| 5,869,242 A | 2/1999 | Kamb |
| 5,871,697 A | 2/1999 | Rothberg et al. |
| 5,872,003 A | 2/1999 | Koster |
| 5,876,936 A | 3/1999 | Ju |
| 5,876,938 A | 3/1999 | Stolowitz et al. |
| 5,885,775 A | 3/1999 | Haff et al. |
| 5,900,481 A | 5/1999 | Lough et al. |
| 5,928,905 A | 7/1999 | Stemmer et al. |
| 5,928,906 A | 7/1999 | Koster et al. |
| 5,965,363 A | 10/1999 | Monforte et al. |
| 5,965,383 A | 10/1999 | Vogel et al. |
| 5,972,693 A | 10/1999 | Rothberg et al. |
| 5,976,798 A | 11/1999 | Parker et al. |
| 5,981,176 A | 11/1999 | Wallace |
| 5,981,190 A | 11/1999 | Israel |
| 5,994,066 A | 11/1999 | Bergeron et al. |
| 6,001,564 A | 12/1999 | Bergeron et al. |
| 6,005,096 A | 12/1999 | Matteucci et al. |
| 6,007,690 A | 12/1999 | Nelson et al. |
| 6,007,992 A | 12/1999 | Lin et al. |
| 6,015,666 A | 1/2000 | Springer et al. |
| 6,018,713 A | 1/2000 | Coli et al. |
| 6,024,925 A | 2/2000 | Little et al. |
| 6,028,183 A | 2/2000 | Lin et al. |
| 6,043,031 A | 3/2000 | Koester et al. |
| 6,046,005 A | 4/2000 | Ju et al. |
| 6,051,378 A | 4/2000 | Monforte et al. |
| 6,054,278 A | 4/2000 | Dodge et al. |
| 6,055,487 A | 4/2000 | Margery et al. |
| 6,060,246 A | 5/2000 | Summerton et al. |
| 6,061,686 A | 5/2000 | Gauvin et al. |
| 6,063,031 A | 5/2000 | Cundari et al. |
| 6,074,823 A | 6/2000 | Koster |
| 6,074,831 A | 6/2000 | Yakhini et al. |
| 6,090,558 A | 7/2000 | Butler et al. |
| 6,104,028 A | 8/2000 | Hunter et al. |
| 6,110,710 A | 8/2000 | Smith et al. |
| 6,111,251 A | 8/2000 | Hillenkamp |
| 6,133,436 A | 10/2000 | Koster et al. |
| 6,140,053 A | 10/2000 | Koster |
| 6,146,144 A | 11/2000 | Fowler et al. |
| 6,146,854 A | 11/2000 | Koster et al. |
| 6,153,389 A | 11/2000 | Haarer et al. |
| 6,159,681 A | 12/2000 | Zebala |
| 6,180,339 B1 | 1/2001 | Sandhu et al. |
| 6,180,372 B1 | 1/2001 | Franzen |
| 6,187,842 B1 | 2/2001 | Kobayashi et al. |
| 6,194,144 B1 | 2/2001 | Koster |
| 6,197,498 B1 | 3/2001 | Koster |
| 6,214,555 B1 | 4/2001 | Leushner et al. |
| 6,218,118 B1 | 4/2001 | Sampson et al. |
| 6,221,587 B1 | 4/2001 | Ecker et al. |
| 6,221,598 B1 | 4/2001 | Schumm et al. |
| 6,221,601 B1 | 4/2001 | Koster et al. |
| 6,221,605 B1 | 4/2001 | Koster |
| 6,225,450 B1 | 5/2001 | Koster |
| 6,235,476 B1 | 5/2001 | Bergmann et al. |
| 6,235,478 B1 | 5/2001 | Koster |
| 6,235,480 B1 | 5/2001 | Shultz et al. |
| 6,238,871 B1 | 5/2001 | Koster |
| 6,238,927 B1 | 5/2001 | Abrams et al. |
| 6,239,159 B1 | 5/2001 | Brown et al. |
| 6,258,538 B1 | 7/2001 | Koster et al. |
| 6,261,769 B1 | 7/2001 | Everett et al. |
| 6,265,716 B1 | 7/2001 | Hunter et al. |
| 6,265,718 B1 | 7/2001 | Park et al. |
| 6,266,131 B1 | 7/2001 | Hamada et al. |
| 6,266,144 B1 | 7/2001 | Li |
| 6,268,129 B1 | 7/2001 | Gut et al. |

(56) References Cited

U.S. PATENT DOCUMENTS

| | | |
|---|---|---|
| 6,268,131 B1 | 7/2001 | Kang et al. |
| 6,268,144 B1 | 7/2001 | Koster |
| 6,268,146 B1 | 7/2001 | Shultz et al. |
| 6,270,973 B1 | 8/2001 | Lewis et al. |
| 6,270,974 B1 | 8/2001 | Shultz et al. |
| 6,274,726 B1 | 8/2001 | Laugharn et al. |
| 6,277,573 B1 | 8/2001 | Koster |
| 6,277,578 B1 | 8/2001 | Shultz et al. |
| 6,277,634 B1 | 8/2001 | McCall et al. |
| 6,300,076 B1 | 10/2001 | Koster |
| 6,303,297 B1 | 10/2001 | Lincoln et al. |
| 6,312,893 B1 | 11/2001 | Van Ness et al. |
| 6,312,902 B1 | 11/2001 | Shultz et al. |
| 6,322,970 B1 | 11/2001 | Little et al. |
| 6,361,940 B1 | 3/2002 | Van Ness et al. |
| 6,372,424 B1 | 4/2002 | Brow et al. |
| 6,389,428 B1 | 5/2002 | Rigault et al. |
| 6,391,551 B1 | 5/2002 | Shultz et al. |
| 6,393,367 B1 | 5/2002 | Tang et al. |
| 6,419,932 B1 | 7/2002 | Dale |
| 6,423,966 B2 | 7/2002 | Hillenkamp et al. |
| 6,428,955 B1 | 8/2002 | Koster et al. |
| 6,428,956 B1 | 8/2002 | Crooke et al. |
| 6,432,651 B1 | 8/2002 | Hughes et al. |
| 6,436,635 B1 | 8/2002 | Fu et al. |
| 6,436,640 B1 | 8/2002 | Simmons et al. |
| 6,453,244 B1 | 9/2002 | Oefner |
| 6,458,533 B1 | 10/2002 | Felder et al. |
| 6,468,743 B1 | 10/2002 | Romick et al. |
| 6,468,748 B1 | 10/2002 | Monforte et al. |
| 6,475,143 B2 | 11/2002 | Iliff |
| 6,475,736 B1 | 11/2002 | Stanton |
| 6,475,738 B2 | 11/2002 | Shuber et al. |
| 6,479,239 B1 | 11/2002 | Anderson et al. |
| 6,500,621 B2 | 12/2002 | Koster |
| 6,553,317 B1 | 4/2003 | Query |
| 6,558,902 B1 | 5/2003 | Hillenkamp |
| 6,563,025 B1 | 5/2003 | Song et al. |
| 6,566,055 B1 | 5/2003 | Monforte et al. |
| 6,568,055 B1 | 5/2003 | Tang et al. |
| 6,582,916 B1 | 6/2003 | Schmidt et al. |
| 6,586,584 B2 | 7/2003 | McMillian et al. |
| 6,589,485 B2 | 7/2003 | Koster |
| 6,602,662 B1 | 8/2003 | Koster et al. |
| 6,605,433 B1 | 8/2003 | Fliss et al. |
| 6,610,492 B1 | 8/2003 | Stanton et al. |
| 6,613,509 B1 | 9/2003 | Chen |
| 6,613,520 B2 | 9/2003 | Ashby |
| 6,623,928 B2 | 9/2003 | Van Ness et al. |
| 6,638,714 B1 | 10/2003 | Linnen et al. |
| 6,680,476 B1 | 1/2004 | Hidalgo et al. |
| 6,682,889 B1 | 1/2004 | Wang et al. |
| 6,705,530 B2 | 3/2004 | Kiekhaefer |
| 6,706,530 B2 | 3/2004 | Hillenkamp |
| 6,783,939 B2 | 8/2004 | Olmsted et al. |
| 6,800,289 B2 | 10/2004 | Nagata et al. |
| 6,813,615 B1 | 11/2004 | Colasanti et al. |
| 6,836,742 B2 | 12/2004 | Brekenfeld |
| 6,852,487 B1 | 2/2005 | Barany et al. |
| 6,856,914 B1 | 2/2005 | Pelech |
| 6,875,593 B2 | 4/2005 | Froehler et al. |
| 6,906,316 B2 | 6/2005 | Sugiyama et al. |
| 6,906,319 B2 | 6/2005 | Hoyes |
| 6,914,137 B2 | 7/2005 | Baker |
| 6,977,148 B2 | 12/2005 | Dean et al. |
| 6,994,962 B1 | 2/2006 | Thilly |
| 7,022,835 B1 | 4/2006 | Rauth et al. |
| 7,024,370 B2 | 4/2006 | Epler et al. |
| 7,108,974 B2 | 9/2006 | Ecker et al. |
| 7,198,893 B1 | 4/2007 | Köster et al. |
| 7,217,510 B2 | 5/2007 | Ecker et al. |
| 7,226,739 B2 | 6/2007 | Ecker et al. |
| 7,255,992 B2 | 8/2007 | Ecker et al. |
| 7,285,422 B1 | 10/2007 | Little et al. |
| 7,312,036 B2 | 12/2007 | Sampath et al. |
| 7,321,828 B2 | 1/2008 | Cowsert et al. |
| 7,349,808 B1 | 3/2008 | Kreiswirth et al. |
| 7,390,458 B2 | 6/2008 | Burow et al. |
| 7,419,787 B2 | 9/2008 | Köster |
| 7,501,251 B2 | 3/2009 | Köster et al. |
| 7,666,588 B2 | 2/2010 | Ecker et al. |
| 7,718,354 B2 | 5/2010 | Ecker et al. |
| 7,741,036 B2 | 6/2010 | Ecker et al. |
| 7,781,162 B2 | 8/2010 | Ecker et al. |
| 2001/0039263 A1 | 11/2001 | Matthes et al. |
| 2002/0001812 A1 | 1/2002 | Smith et al. |
| 2002/0006611 A1 | 1/2002 | Portugal et al. |
| 2002/0042112 A1 | 4/2002 | Koster et al. |
| 2002/0042506 A1 | 4/2002 | Kristyanne et al. |
| 2002/0045178 A1 | 4/2002 | Cantor et al. |
| 2002/0055101 A1 | 5/2002 | Bergeron et al. |
| 2002/0120408 A1 | 8/2002 | Kreiswirth et al. |
| 2002/0137057 A1 | 9/2002 | Wold et al. |
| 2002/0138210 A1 | 9/2002 | Wilkes et al. |
| 2002/0150927 A1 | 10/2002 | Matray et al. |
| 2002/0168630 A1 | 11/2002 | Fleming et al. |
| 2002/0187490 A1 | 12/2002 | Tiedje et al. |
| 2003/0017487 A1 | 1/2003 | Xue et al. |
| 2003/0027135 A1 | 2/2003 | Ecker et al. |
| 2003/0039976 A1 | 2/2003 | Haff |
| 2003/0050470 A1 | 3/2003 | An et al. |
| 2003/0064483 A1 | 4/2003 | Shaw et al. |
| 2003/0073112 A1 | 4/2003 | Zhang et al. |
| 2003/0084483 A1 | 5/2003 | Simpson et al. |
| 2003/0101172 A1 | 5/2003 | De La Huerga |
| 2003/0104410 A1 | 6/2003 | Mittmann |
| 2003/0104699 A1 | 6/2003 | Minamihaba et al. |
| 2003/0113738 A1 | 6/2003 | Liu et al. |
| 2003/0113745 A1 | 6/2003 | Monforte et al. |
| 2003/0119018 A1 | 6/2003 | Omura et al. |
| 2003/0129589 A1 | 7/2003 | Koster et al. |
| 2003/0134312 A1 | 7/2003 | Burgoyne |
| 2003/0148281 A1 | 8/2003 | Glucksmann |
| 2003/0148284 A1 | 8/2003 | Vision et al. |
| 2003/0167133 A1 | 9/2003 | Ecker et al. |
| 2003/0167134 A1 | 9/2003 | Ecker et al. |
| 2003/0175695 A1 | 9/2003 | Ecker et al. |
| 2003/0175696 A1 | 9/2003 | Ecker et al. |
| 2003/0175697 A1 | 9/2003 | Ecker et al. |
| 2003/0175729 A1 | 9/2003 | Van Eijk et al. |
| 2003/0186247 A1 | 10/2003 | Smarason et al. |
| 2003/0187588 A1 | 10/2003 | Ecker et al. |
| 2003/0187593 A1 | 10/2003 | Ecker et al. |
| 2003/0190605 A1 | 10/2003 | Ecker et al. |
| 2003/0190635 A1 | 10/2003 | McSwiggen |
| 2003/0194699 A1 | 10/2003 | Lewis et al. |
| 2003/0203398 A1 | 10/2003 | Bramucci et al. |
| 2003/0220844 A1 | 11/2003 | Marnellos et al. |
| 2003/0224377 A1 | 12/2003 | Wengel et al. |
| 2003/0225529 A1 | 12/2003 | Ecker et al. |
| 2003/0228571 A1 | 12/2003 | Ecker et al. |
| 2003/0228597 A1 | 12/2003 | Cowsert et al. |
| 2003/0228613 A1 | 12/2003 | Bornarth et al. |
| 2004/0005555 A1 | 1/2004 | Rothman et al. |
| 2004/0013703 A1 | 1/2004 | Ralph et al. |
| 2004/0014957 A1 | 1/2004 | Eldrup et al. |
| 2004/0023207 A1 | 2/2004 | Polansky |
| 2004/0023209 A1 | 2/2004 | Jonasson |
| 2004/0029129 A1 | 2/2004 | Wang et al. |
| 2004/0038206 A1 | 2/2004 | Zhang et al. |
| 2004/0038208 A1 | 2/2004 | Fisher et al. |
| 2004/0038234 A1 | 2/2004 | Gut et al. |
| 2004/0038385 A1 | 2/2004 | Langlois et al. |
| 2004/0081993 A1 | 4/2004 | Cantor et al. |
| 2004/0101809 A1 | 5/2004 | Weiss et al. |
| 2004/0110169 A1 | 6/2004 | Ecker et al. |
| 2004/0111221 A1 | 6/2004 | Beattie et al. |
| 2004/0117129 A1 | 6/2004 | Ecker et al. |
| 2004/0117354 A1 | 6/2004 | Azzaro et al. |
| 2004/0121309 A1 | 6/2004 | Ecker et al. |
| 2004/0121310 A1 | 6/2004 | Ecker et al. |
| 2004/0121311 A1 | 6/2004 | Ecker et al. |
| 2004/0121312 A1 | 6/2004 | Ecker et al. |
| 2004/0121313 A1 | 6/2004 | Ecker et al. |

(56) References Cited

U.S. PATENT DOCUMENTS

| | | |
|---|---|---|
| 2004/0121314 A1 | 6/2004 | Ecker et al. |
| 2004/0121315 A1 | 6/2004 | Ecker et al. |
| 2004/0121329 A1 | 6/2004 | Ecker et al. |
| 2004/0121335 A1 | 6/2004 | Ecker et al. |
| 2004/0121340 A1 | 6/2004 | Ecker et al. |
| 2004/0122598 A1 | 6/2004 | Ecker et al. |
| 2004/0122857 A1 | 6/2004 | Ecker et al. |
| 2004/0126764 A1 | 7/2004 | Lasken et al. |
| 2004/0137013 A1 | 7/2004 | Katinger et al. |
| 2004/0185438 A1 | 9/2004 | Ecker |
| 2004/0191769 A1 | 9/2004 | Marino et al. |
| 2004/0202997 A1 | 10/2004 | Ecker et al. |
| 2004/0253583 A1 | 12/2004 | Ecker et al. |
| 2004/0253619 A1 | 12/2004 | Ecker et al. |
| 2005/0026147 A1 | 2/2005 | Walker et al. |
| 2005/0026641 A1 | 2/2005 | Hokao |
| 2005/0027459 A1 | 2/2005 | Ecker et al. |
| 2005/0065813 A1 | 3/2005 | Mishelevich et al. |
| 2005/0130216 A1 | 6/2005 | Becker et al. |
| 2005/0142584 A1 | 6/2005 | Willson et al. |
| 2005/0250125 A1 | 11/2005 | Novakoff |
| 2005/0266411 A1 | 12/2005 | Hofstadler et al. |
| 2006/0020391 A1 | 1/2006 | Kreiswirth et al. |
| 2006/0172330 A1 | 8/2006 | Osborn et al. |
| 2006/0201887 A1 | 9/2006 | Siddiqi |
| 2006/0205040 A1 | 9/2006 | Sampath |
| 2006/0240412 A1 | 10/2006 | Hall et al. |
| 2006/0259249 A1 | 11/2006 | Sampath et al. |
| 2008/0096214 A1 | 4/2008 | Ammann et al. |
| 2008/0311558 A1 | 12/2008 | Ecker et al. |
| 2009/0004643 A1 | 1/2009 | Ecker et al. |
| 2009/0023150 A1 | 1/2009 | Koster et al. |
| 2009/0042203 A1 | 2/2009 | Koster |
| 2009/0092977 A1 | 4/2009 | Koster |
| 2009/0182511 A1 | 7/2009 | Ecker et al. |
| 2010/0145626 A1 | 6/2010 | Ecker et al. |
| 2010/0184035 A1 | 7/2010 | Hall et al. |

FOREIGN PATENT DOCUMENTS

| | | |
|---|---|---|
| DE | 19824280 A1 | 12/1999 |
| DE | 19852167 A1 | 5/2000 |
| DE | 19943374 A1 | 3/2001 |
| DE | 10132147 A1 | 2/2003 |
| EP | 281390 A2 | 9/1988 |
| EP | 633321 A1 | 1/1995 |
| EP | 620862 B1 | 4/1998 |
| EP | 1035219 A1 | 9/2000 |
| EP | 1138782 A2 | 10/2001 |
| EP | 1234888 A2 | 8/2002 |
| EP | 1308506 A1 | 5/2003 |
| EP | 1310571 A2 | 5/2003 |
| EP | 1333101 A1 | 8/2003 |
| EP | 1365031 A1 | 11/2003 |
| EP | 1234888 A3 | 1/2004 |
| EP | 1748072 A1 | 1/2007 |
| FR | 2811321 A1 | 1/2002 |
| GB | 2325002 A | 11/1998 |
| GB | 2339905 A | 2/2000 |
| JP | 57171266 | 10/1982 |
| JP | 5276999 A2 | 10/1993 |
| JP | 11137259 A | 5/1999 |
| JP | 24024206 A2 | 1/2004 |
| JP | 2004000200 A2 | 1/2004 |
| JP | 24201679 A2 | 7/2004 |
| JP | 2004201641 A | 7/2004 |
| WO | WO-8803957 A1 | 6/1988 |
| WO | WO-9015157 A1 | 12/1990 |
| WO | WO-9204961 A1 | 4/1992 |
| WO | WO-9205182 A1 | 4/1992 |
| WO | WO-9208117 A1 | 5/1992 |
| WO | WO-9209703 A1 | 6/1992 |
| WO | WO-9219774 A1 | 11/1992 |
| WO | WO-9303186 A1 | 2/1993 |
| WO | WO-9303383 A1 | 2/1993 |
| WO | WO-9305182 A1 | 3/1993 |
| WO | WO-9308297 A1 | 4/1993 |
| WO | WO-9325913 A1 | 12/1993 |
| WO | WO-9416101 A2 | 7/1994 |
| WO | WO-9419490 A1 | 9/1994 |
| WO | WO-9421822 A1 | 9/1994 |
| WO | WO-9504161 A1 | 2/1995 |
| WO | WO-9511996 A1 | 5/1995 |
| WO | WO-9513395 A1 | 5/1995 |
| WO | WO-9513396 A2 | 5/1995 |
| WO | WO-9531997 A1 | 11/1995 |
| WO | WO-9606187 A1 | 2/1996 |
| WO | WO-9616186 A1 | 5/1996 |
| WO | WO-9629431 A2 | 9/1996 |
| WO | WO-9632504 A2 | 10/1996 |
| WO | WO-9635450 A1 | 11/1996 |
| WO | WO-9637630 A1 | 11/1996 |
| WO | WO-9733000 A1 | 9/1997 |
| WO | WO-9734909 A1 | 9/1997 |
| WO | WO-9737041 A2 | 10/1997 |
| WO | WO-9747766 A1 | 12/1997 |
| WO | WO-9803684 A1 | 1/1998 |
| WO | WO-9812355 A1 | 3/1998 |
| WO | WO-9814616 A1 | 4/1998 |
| WO | WO-9815652 A1 | 4/1998 |
| WO | WO-9820020 A2 | 5/1998 |
| WO | WO-9820157 A2 | 5/1998 |
| WO | WO-9820166 A2 | 5/1998 |
| WO | WO-9826095 A1 | 6/1998 |
| WO | WO-9831830 A1 | 7/1998 |
| WO | WO-9835057 A1 | 8/1998 |
| WO | WO-9840520 A1 | 9/1998 |
| WO | WO-9854571 A1 | 12/1998 |
| WO | WO-9854751 A1 | 12/1998 |
| WO | WO-9905319 A2 | 2/1999 |
| WO | WO-9912040 A2 | 3/1999 |
| WO | WO-9913104 A1 | 3/1999 |
| WO | WO-9914375 A2 | 3/1999 |
| WO | WO-9929898 A2 | 6/1999 |
| WO | WO-9931278 A1 | 6/1999 |
| WO | WO-9956863 A1 | 11/1999 |
| WO | WO-9957318 A2 | 11/1999 |
| WO | WO-9958713 A2 | 11/1999 |
| WO | WO-9960183 A1 | 11/1999 |
| WO | WO-0032750 A1 | 6/2000 |
| WO | WO-0038636 A1 | 7/2000 |
| WO | WO-0063362 A1 | 10/2000 |
| WO | WO-0066762 A2 | 11/2000 |
| WO | WO-0066789 A2 | 11/2000 |
| WO | WO-0077260 A1 | 12/2000 |
| WO | WO-0100828 A2 | 1/2001 |
| WO | WO-0107648 A1 | 2/2001 |
| WO | WO-0110554 A2 | 2/2001 |
| WO | WO-0112853 A1 | 2/2001 |
| WO | WO-0120018 A2 | 3/2001 |
| WO | WO-0123604 A2 | 4/2001 |
| WO | WO-0123608 A2 | 4/2001 |
| WO | WO-0132930 A1 | 5/2001 |
| WO | WO-0140497 A2 | 6/2001 |
| WO | WO-0146404 A1 | 6/2001 |
| WO | WO-0151661 A2 | 7/2001 |
| WO | WO-0151662 A1 | 7/2001 |
| WO | WO-0157263 A1 | 8/2001 |
| WO | WO-0157518 A2 | 8/2001 |
| WO | WO-0173119 A2 | 10/2001 |
| WO | WO-0173199 A2 | 10/2001 |
| WO | WO-0177392 A2 | 10/2001 |
| WO | WO-0196388 A2 | 12/2001 |
| WO | WO-0202811 A2 | 1/2002 |
| WO | WO-0210186 A1 | 2/2002 |
| WO | WO-0210444 A2 | 2/2002 |
| WO | WO-0218641 A2 | 3/2002 |
| WO | WO-0221108 A2 | 3/2002 |
| WO | WO-0222873 A1 | 3/2002 |
| WO | WO-0224876 A2 | 3/2002 |
| WO | WO-0250307 A1 | 6/2002 |
| WO | WO-02057491 A2 | 7/2002 |
| WO | WO-02070664 A2 | 9/2002 |

(56) References Cited

FOREIGN PATENT DOCUMENTS

| WO | WO-02070728 A2 | 9/2002 |
|---|---|---|
| WO | WO-02070737 A2 | 9/2002 |
| WO | WO-02077278 A1 | 10/2002 |
| WO | WO-02099034 A2 | 12/2002 |
| WO | WO-02099095 A2 | 12/2002 |
| WO | WO-02099129 A2 | 12/2002 |
| WO | WO-02099130 A2 | 12/2002 |
| WO | WO-03001976 A2 | 1/2003 |
| WO | WO-03002750 A2 | 1/2003 |
| WO | WO-03008636 A2 | 1/2003 |
| WO | WO-03012058 A2 | 2/2003 |
| WO | WO-03012074 A2 | 2/2003 |
| WO | WO-03014382 A2 | 2/2003 |
| WO | WO-03016546 A1 | 2/2003 |
| WO | WO-03018636 A2 | 3/2003 |
| WO | WO-03020890 A2 | 3/2003 |
| WO | WO-03033732 A2 | 4/2003 |
| WO | WO-03054162 A2 | 7/2003 |
| WO | WO-03054755 A2 | 7/2003 |
| WO | WO-03060163 A2 | 7/2003 |
| WO | WO-03075955 A1 | 9/2003 |
| WO | WO-03088979 A2 | 10/2003 |
| WO | WO-03093506 A2 | 11/2003 |
| WO | WO-03097869 A2 | 11/2003 |
| WO | WO-03100035 A2 | 12/2003 |
| WO | WO-03100068 A1 | 12/2003 |
| WO | WO-03102191 A1 | 12/2003 |
| WO | WO-03104410 A2 | 12/2003 |
| WO | WO-03106635 A2 | 12/2003 |
| WO | WO-2004003511 A2 | 1/2004 |
| WO | WO-2004009849 A1 | 1/2004 |
| WO | WO-2004011651 A1 | 2/2004 |
| WO | WO-2004013357 A2 | 2/2004 |
| WO | WO-2004040013 A1 | 5/2004 |
| WO | WO-2004044123 A2 | 5/2004 |
| WO | WO-2004044247 A2 | 5/2004 |
| WO | WO-2004052175 A2 | 6/2004 |
| WO | WO-2004053076 A2 | 6/2004 |
| WO | WO-2004053141 A2 | 6/2004 |
| WO | WO-2004053164 A1 | 6/2004 |
| WO | WO-2004060278 A2 | 7/2004 |
| WO | WO-2004070001 A2 | 8/2004 |
| WO | WO-2004072230 A2 | 8/2004 |
| WO | WO-2004072231 A2 | 8/2004 |
| WO | WO-2004101809 A2 | 11/2004 |
| WO | WO-2005003384 A1 | 1/2005 |
| WO | WO-2005009202 A2 | 2/2005 |
| WO | WO-2005012572 A1 | 2/2005 |
| WO | WO-2005024046 A2 | 3/2005 |
| WO | WO-2005036369 A2 | 4/2005 |
| WO | WO-2005054454 A1 | 6/2005 |
| WO | WO-2005075686 A1 | 8/2005 |
| WO | WO-2005086634 A2 | 9/2005 |
| WO | WO-2005091971 A2 | 10/2005 |
| WO | WO-2005098047 A2 | 10/2005 |
| WO | WO-2005116263 A2 | 12/2005 |
| WO | WO-2006089762 A1 | 8/2006 |
| WO | WO-2006094238 A2 | 9/2006 |
| WO | WO-2006135400 A2 | 12/2006 |
| WO | WO-2007014045 A2 | 2/2007 |
| WO | WO-2007086904 A2 | 8/2007 |
| WO | WO-2008104002 A2 | 8/2008 |
| WO | WO-2008118809 A1 | 10/2008 |

OTHER PUBLICATIONS

Aaserud D.J., et al., "DNA Sequencing with Blackbody Infrared Radioactive Dissociation of Electrosprayed Ions," International Journal of Mass Spectrometry and Icon Processes, 1997, vol. 167/168, pp. 705-712.

Adam E., et al., "Characterization of Intertype Specific Epitopes on Adenovirus Hexons," Archives of Virology, 1998, vol. 143 (9), pp. 1669-1682.

Adam E., et al., "Intertype Specific Epitope Structure of Adenovirus Hexon," Acta Microbiologica et Immunologica Hungarica, 1998, vol. 45 (3-4), pp. 311-316.

Adam E., et al., "Molecular Structure of the Two-Dimensional Hexon Crystalline Array and of Adenovirus Capsid," Acta Microbiologica et Immunologica Hungarica, 1998, vol. 45 (3-4), pp. 305-310.

Adrian T., et al., "DNA Restriction Analysis of Adenovirus Prototypes 1 to 41," Archives of Virology, 1986, vol. 91 (3-4), pp. 277-290.

Adzhar A., et al., "Universal Oligonucleotides for the Detection of Infectious Bronchitis Virus by Thepolymerase Chain Reaction," Avian Pathology, 1996, vol. 25 (4), pp. 817-836.

Agostini H.T., et al., "Complete Genome of a JC Virus Genotype Type 6 from the Brain of an African American with Progressive Multifocal Leukoencephalopathy," Journal of Human Virology, 1998, vol. 1 (4), pp. 267-272.

Aires De Sousa M., et al., "Bridges from Hospitals to the Laboratory: Genetic Portraits of Methicillin-Resistant *Staphylococcus aureus* Clones," FEMS Immunology and Medical Microbiology, 2004, vol. 40 (2), pp. 101-111.

Akalu A., et al., "Rapid Identification of Subgenera of Human Adenovirus by Serological and PCR Assays," Journal of Virological Methods, 1998, vol. 71 (2), pp. 187-196.

Alba M.M., et al., "VIDA: A Virus Database System for the Organization of Animal Virus Genome Open Reading Frames," Nucleic Acids Research, 2001, vol. 29 (1), pp. 133-136.

Allaouchiche B., et al., "Clinical Impact of Rapid Oxacillin Susceptibility Testing Using a PCR Assay in *Staphylococcus aureus* Bactaeremia," The Journal of Infection, 1999, vol. 39 (3), pp. 198-204.

Allawi H.T., et al., "Thermodynamics and NMR of Internal G.T. Mismatches in DNA," Biochemistry, 1997, vol. 36 (34), pp. 10581-10594.

Altschuel S.F., et al., "Basic Local Alignment Search Tool," Journal of Molecular Biology, 1990, vol. 215 (3), pp. 403-410.

Altschul S.F., et al., "Gapped BLAST and PSI-BLAST: A New Generation of Protein Database Search Programs," Nucleic Acids Research, 1997, 25 (17), 3389-3402.

Alves-Silva J., et al., "The Ancestry of Brazilian mtDNA Linages," The American Journal of Human Genetics, 2000, vol. 67 (2), pp. 444-461.

Amano Y., et al., "Detection of Influenza Virus: Traditional Approaches and Development of Biosensors," Analytical and Bioanalytical Chemistry, 2005, vol. 381 (1), pp. 156-164.

Amexis G., et al., "Quantitative Mutant Analysis of Viral Quasispecies by Chip-Based Matrix Assisted LaserDesorption Ionization Time-of-Flight Mass Spectrometry," Proceedings of the National Academy of Sciences, 2001, vol. 98 (21), pp. 12097-12102.

Anderson M.L.M., "Quantitative Filter Hybridization" in: Nucleic Acid Hybridization, Hames B.D., ed., IRL Press, 1985, pp. 73-111.

Anderson S., et al., "Sequence and Organization of the Human Mitochondrial Genome," Nature, 1981, vol. 290 (5806), pp. 457-465.

Andreasson H., et al., "Mitochondrial Sequence Analysis for Forensic Identification Using Pyrosequencing Technology," BioTechniques, 2002, vol. 32 (1), pp. 124-133.

Anthony R.M., et al., "Use of the Polymerase Chain Reaction for Rapid Detection of High-Level Mupirocin Resistance in Staphylococci," European Journal of Clinical Microbiology & Infectious Diseases, 1999, vol. 18 (1), pp. 30-34.

Arbique J., et al., "Comparison of the Velogene Rapid MRSA Identification Assay, Denka MRSAScreen Assay, and BBL Crystal MRSA ID System for Rapid Identification of Methicillin-Resistant *Staphylococcus aureus*," Diagnostic Microbiology and Infectious Diseases, 2001, vol. 40 (1-2), pp. 5-10.

Archer G.L., et al., "Detection of Methicillin Resistance in Staphylococci by Using a DNA Probe," Antimicrobial Agents and Chemotherapy, 1990, vol. 34 (9), pp. 1720-1724.

Armstrong P., et al., "Sensitive and Specific Colorimetric Dot Assay to Detect Eastern Equine Encephalomyelitis Viral RNA in Mosquitoes After PCR Amplification," Journal of Medicinal Entomology, 1995, vol. 32 (1), pp. 42-52.

(56) References Cited

OTHER PUBLICATIONS

Arnal C., et al., "Quantification of Hepatitis A Virus in Shellfish by Competitive Reverse Transcription PCR with Coextraction of Standard RNA," Applied and Environmental Microbiology, 1999, vol. 65 (1), pp. 322-326.

Aronsson F., et al., "Persistence of the Influenza A/WSN/33 Virus RNA at Midbrain Levels of Immunodefective Mice," Journal of Neurovirology, 2001, vol. 7 (2), pp. 117-124.

Ausubel F.M., et al., Eds., Current Protocols in Molecular Biology, vol. 1, John Wiley & Sons Inc., 2004, Table of Contents.

Ausubel F.M., et al., eds., Short Protocols in Molecular Biology: A Compendium of Methods from Current Protocols in Molecular Biology, 2nd Edition, John Wiley & Sons, 1992, Units 2.9, 3.4-3.17, 4.6-4.10, and 10.8.

Ausubel F.M., et al., "Unit 2.11 "Synthesis and Purification of Oligonucleotides," in: Current Protocols in Molecular Biology," 1998, John Wiley & Sons, Inc., pp. 2.11-2.11.21.

Avellon A., et al., "Rapid and Sensitive Diagnosis of Human Adenovirus Infections by a Generic Polymerase Chain Reaction," Journal of Virological Methods, 2001, vol. 92 (2), pp. 113-120.

Azevedo A.M., et al., "Detection of Influenza, Parainfluenza, Adenovirus and Respiratory Syncytial Virus during Asthma Attacks in Children Older than 2 Years Old," Allergologia Immunopathologia, 2003, vol. 31 (6), pp. 311-317.

Baba T., et al., "Genome and Virulence Determinants of High Virulence Community-Acquired MRSA," Lancet, 2002, vol. 359 (9320), pp. 1819-1827.

Bahrmahd A.R., et al., "Polymerise Chain Reaction of Bacterial Genomes with Single Universal Primer: Application to Distinguishing Mycobacteria Species," Molecular and Cellular Probes, 1996, vol. 10 (2), pp. 117-122.

Bahrmahd A.R., et al., "Use of Restriction Enzyme Analysis of Amplified DNA Coding for the hsp65 Gene and Polymerase Chain Reaction with Universal Primer for Rapid Differtiation of Mycobacterium Species in the Clinical Laboratory," Scandinavian Journal of Infectious Diseases, 1998, vol. 30 (5), pp. 477-480.

Bai J., et al., "Matrix-Assisted Laser Desorption/Ionization Mass Spectrometry of Restriction Enzyme-Digested Plasmid DNA Using an Active Nafion Substrate," Rapid Communications in Mass Spectrometry, 1994, vol. 8 (9), pp. 687-691.

Baker G.C., et al., "Review and Re-Analysis of Domain-Specific 16S Primers," Journal of Microbiological Methods, 2003, vol. 55 (3), pp. 541-555.

Banik U., et al., "Multiplex PCR Assay for Rapid Identification of Oculopathogenic Adenoviruses by Amplification of the Fiber and Hexon Genes," Journal of Clincal Microbiology, 2005, vol. 43 (3), pp. 1064-1068.

Barbour A.G., et al., "Identification of an Uncultivatable *Borrelia* Species in the Hard Tick *Amblyomma americanum*: Possible Agent of a Lyme Disease-Like Illness," The Journal of Infectious Diseases, 1996, vol. 173 (2), pp. 403-409.

Barns S.M., et al., "Detection of Diverse New *Francisella*-like Bacteria in Environmental Samples," Applied and Environmental Microbiology, 2005, vol. 71 (9), pp. 5494-5500.

Baron E.J., "Genetic Aspects of Methicillin Resistance in *Staphylococcus aureus* and MethodsUsed for its Detection in Clinical Laboratories in the United States," Journal of Chemotherapy, 1995, vol. 7 (Suppl. 3), pp. 87-92.

Barr I.G., et al., "An Influenza A(H3) Reassortant was Epidemic in Australia and New Zealand in 2003," Journal of Medical Virology, 2005, vol. 76 (3), pp. 391-397.

Barski P., et al., "Rapid Assay for Detection of Methicillin-Resistant *Staphylococcus aureus* Using Multiplex PCR," Molecular and Cellular Probes, 1996, vol. 10 (6), pp. 471-475.

Bastia T., et al., "Organelle DNA Analysis of *Solanum* and *Brassica* Somatic Hybrids by PCR with Universal Primers," Theoretical and Applied Genetics, 2001, vol. 102 (8), pp. 1265-1272.

Batey R.T., et al., "Preparation of Isotopically Labeled Ribonucleotides for Multidimensional NMR Spectroscopy of RNA," Nucleic Acids Research, 1992, vol. 20 (17), pp. 4515-4523.

Baumer A., et al., "Age-Related Human mtDNA Deletions: A Heterogeneous Set of Deletions Arising at aSingle Pair of Directly Repeated Sequences," American Journal of Human Jenetics, 1994, vol. 54 (4), pp. 618-630.

Beall B., et al., "Sequencing emm-Specific PCR Products for Routine andAccurate Typing of Group A Streptococci," Journal of Clincal Microbiology, 1996, vol. 34 (4), pp. 953-958.

Beall B., et al., "Survey of emm Gene Sequences and T-Antigen Types from Systemic *Streptococcus pyogenes* Infection Isolates Collected in San Francisco, California; Atlanta, Georgia; and Connecticut in 1994 and 1995," Journal of Clincal Microbiology, 1997, vol. 35 (5), pp. 1231-1235.

Benko, M. et al., "Family Adenoviridae," Virus taxonomy. VIIIth report of the International Committee on Taxonomy of Viruses, 2004, Academic Press, New York, pp. 213-228.

Benson D.A., et al., "GenBank," Nucleic Acids Research, 1999, vol. 27 (1), pp. 12-17.

Benson L.M., et al, "Advantages of *Thermococcus kodakaraenis* (KOD) DNA Polymerase for PCR-Mass Spectrometry Based Analyses," American Society for Mass Spectrometry, 2003, vol. 14 (6), pp. 601-604.

Berencsi G., et al., "Molecular Biological Characterization of Adenovirus DNA," Acta Microbiologica et Immunologica Hungarica, 1998, vol. 45 (3-4), pp. 297-304.

Bishop M.J., et al., "Molecular Sequence Databases" in: Nucleic Acid and Protein Sequence Analysis, 4th Chapter, Bishop M.J., et al., Eds, IRL Press, 1987, pp. 83-113.

Bisno A.L., "*Streptococcus pyogenes*" in: Infectious Diseases and Their Etiologic Agents, vol. 2, Mandell, Eds., Churchill Livingston, New York, 1995, pp. 1786-1799.

Black R.M., et al., "Detection of Trace Levels of Tricothecene Mycotoxins in Human Urineby Gas Chromatography-Mass Spectrometry," Journal of Chromatography, 1986, vol. 367 (1), pp. 103-115.

Blaiotta G., et al., "PCR Detection of Staphylococcal Enterotoxin Genes in *Staphyiococcus* Spp. Strains Isolated from Meat and Dairy Products. Evidence for New Variants of seG and Sel in *S. aureus* AB-8802," Journal of Applied Microbiology, 2004, vol. 97 (4), pp. 719-730.

Blast Search results, Mar. 7, 2006.

Boivin-Jahns V., et al., "Bacterial Diversity in a Deep-Subsurface Clay Environment," Applied and Environmental Microbiology, 1996, vol. 62 (9), pp. 3405-3412.

Bolton E.T., et al., "A General Method for the Isolation of RNA Complementary to DNA," Proceedings of the National Academy of Sciences, 1962, vol. 48, pp. 1390-1397.

Bonk T., et al., "Matrix-Assisted Laser Desorption/Ionization Time-of-Flight Mass Spectrometry-Based Detection of Microsatellite Instabilities in Coding DNA Sequences: A Novel Approach to Identify DNA-Mismatch Repair-Deficient Cancer Cells," Clinical Chemistry, 2003, vol. 49 (4), pp. 552-561.

Borrow R., et al., "SiaD PCR Elisa for Confirmation and Identification of Serogroup Y and W135 Meningococcal Infections," FEMS Microbiology Letters, 1998, vol. 159 (2), pp. 209-214.

Boubaker K., et al., "Panton-Valentine Leukocidin and Staphylococcal Skin Infections in Schoolchildren," Emerging Infectious Diseases, 2004, vol. 10 (1), pp. 121-124.

Bowen J.E., et al., "The Native Virulence Plasmid Combination Affects the Segregational Stability of a Thetareplicating Shuttle Vector in *Bacillus anthracis* Var," Journal of Applied Microbiology, 1999, vol. 87 (2), pp. 270-278.

Bowers K.M., et al., "Screening for Methicillin Resistance in *Staphylococars aureus* and Coagulasenegative Staphylococci: Evaluation of Three Selective and Mastalex-MRSA latex Agglutination," British Journal of Biomedical Science, 2003, vol. 60 (2), pp. 71-74.

Brakstad O.G., et al., "Direct Identification of *Staphylococcus aureus* in Blood Cultures Bydetection of the Gene, Encoding the Thermostable Nuclease or the Gene Product," Acta Pathologica, Microbiologica et Immunologica Scandinavica, 1995, vol. 103 (3), pp. 209-218.

Brakstad O.G., et al., "Multiplex Polymerase Chain Reaction for Detection of Genes for *Staphylococcus aureus* Themonuclease and

(56) References Cited

OTHER PUBLICATIONS

Methicillin Resistance and Correlation with Oxacillin Resistance," Acta Pathologica, Microbiologica et Immunologica Scandinavica, 1993, vol. 101 (9), pp. 681-688.
Brandt C.D., et al., "Infections in 18,000 Infants and Children in a Controlled Study of Respiratory Tract Disease. I. Adenovirus Pathogenicity in Relation to Serologic Type and Illness Syndrome," American Journal of Epidemiology, 1969, vol. 90 (6), pp. 484-500.
Brayshaw D.P., "Methicillin-Resistant *Staphylococcus aureus*: Evaluation of Detection Techniques on Laboratory-Passaged Organisms," British Journal of Biomedical Science, 1999, vol. 56 (3), pp. 170-176.
Brightwell G., et al., "Development of Internal Controls for PCR Detection of *Bacillus anthracis*," Molecular and Cellular Probes, 1998, vol. 12 (6), pp. 367-377.
Brightwell G., et al., "Genetic Targets for the Detection and Identifiaction of Venezuelan Equine Encephalitis Viruses," Archives of Virology, 1998, vol. 143 (4), pp. 731-742.
Bronzoni R.V.M., et al., "Duplex Reverse Transcription-PCR Followed by Nested PCR Assays for Detection and Identification of Brazilian *Alphaviruses* and *Flaviviruses*," Journal of Clincal Microbiology, 2005, vol. 43 (2), pp. 696-702.
Bronzoni R.V.M., et al., "Multiplex Nested PCR for Brazilian *Alphavirus* Diagnosis," Transactions of the Royal Society of Tropical Medicine and Hygiene, 2004, vol. 98 (8), pp. 456-461.
Brown I.H., "Advances in Molecular Diagnostics for Avian Influenza," Developments in Biologicals, 2006, vol. 124, pp. 93-97.
Brownstein M.J., et al., "Modulation of Non-Templated Nucleotide Addition by Taq DNA Polymerase: Primer Modifications that Facilitate Genotyping," BioTechniques, 1996, vol. 20 (6), pp. 1004-1010.
Brunaud V., et al., "T-DNA Integration into the *Arabidopsis* Genome Depends on Sequence of Pre-Insertion Sites," EMBO Reports, 2002, vol. 3 (12), pp. 1152-1157.
Buck G.A., et al., "Design Strategies and Performance of Custom DNA Sequencing Primers," BioTechniques, 1999, vol. 27 (3), pp. 528-536.
Buetow K.H., et al., "High-Throughput Development and Characterization of a Genomewide Collection of Gene-Based Single Nucleotide Polymorphism Markers by Chip-Based Matrix-Assisted Laser Desorption/Ionization Time-of-Flight Mass Spectrometry," Proceedings of the National Academy of Sciences, 2001, vol. 98 (2), pp. 581-584.
Butel J.S., et al., "Cell and Molecular Biology of Simian Virus 40: Implications for Human Infections and Disease," Journal of the National Cancer Institute, 1999, vol. 91 (2), pp. 119-134.
Butler J., "DNA Profiling and Quantitation of Human DNA," CCQM Bio Analysis Working Group, 2005.
Butler J.M., et al., High Throughput Genotyping of Forensic STRs and SNPs using Time-of-Flight Mass Spectrometry, 9th International Symposium on Human Identification, 1998, Orlando FL.
Campbell W.P., et al., "Detection of California Serogroup Bunyavirus in Tissue Culture and Mosquito Pools by PCR," Journal of Virological Methods, 1996, vol. 57 (2), pp. 175-179.
Carracedo A., et al., "DNA Commission of the International Society for Forensic Genetics: Guidelines Formitochondrial DNA Typing," Forensic Science International, 2000, vol. 110 (2), pp. 79-85.
Carroll K.C., et al., "Rapid Detection of the Staphylococcal mecA Gene from BACTEC BloodCulture Bottles by the Polymerase Chain Reaction," American Journal of Clinical Pathology, 1996, vol. 106 (5), pp. 600-605.
Case J.T., et al., "Maternal Inheritance of Mitochondrial DNA Polymorphisms in Cultured Human Fibrolasts," Somatic Cell Genetics, 1981, vol. 7 (1), pp. 103-108.
Cattoli G., et al., "Comparison of Three Rapid Detection Systems for Type A Influenza Virus on Tracheal Swabs of Experimentally and Naturally Infected Birds," Avian Pathology, 2004, vol. 33 (4), pp. 432-437.
Cavassini M., et al., "Evaluation of MRSA-Screen, a Simple Anti-PBP 2a Slide Latex AgglutinationKit, for Rapid Detection of Methicillin Resistance in *Staphylococcus aureus*," Journal of Clincal Microbiology, 1999, vol. 37 (5), pp. 1591-1594.
Certificate of Correction mailed Jan. 6, 2009 for U.S. Appl. No. 10/660,996, filed Sep. 12, 2003.
Certificate of Correction mailed Aug. 7, 2007 for U.S. Appl. No. 10/660,997, filed Sep. 12, 2003.
Certificate of Correction mailed Dec. 12, 2006 for U.S. Appl. No. 10/156,608, filed May 24, 2002.
Certificate of Correction mailed Jul. 17, 2007 for U.S. Appl. No. 09/891,793, filed Jun. 26, 2001.
Certificate of Correction mailed Mar. 31, 2008 for U.S. Appl. No. 09/891,793, filed Jun. 26, 2001.
Certificate of Correction mailed Mar. 31, 2008 for U.S. Appl. No. 10/156,608, filed May 24, 2002.
Certificate of Correction mailed Mar. 31, 2008 for U.S. Appl. No. 10/660,997, filed Sep. 12, 2003.
Cespedes A., et al., "Polymerase Chain Reaction-Restriction Fragment Length Polymorphism Analysis of a Short Fragment of the Cytochrome b Gene for Identification of Flatfish Species," Journal of Food Protection, 1998, vol. 61 (12), pp. 1684-1685.
Chamberlin M., et al., "New RNA Polymerase from *Escherichia coli* Infected with Bacteriophage T7," Nature, 1970, vol. 228 (5268), pp. 227-231.
Chandra S., et al., "Virus Reduction in the Preparation and Intravenous Globulin: In Vitro Experiments," Transfusion, 1999, vol. 39 (3), pp. 249-257.
Chang P.K., et al., "aflT, a MFS Transporter-Encoding Gene Located in the Aflatoxin Gene Cluster, does not have a Significant Role in Aflatoxin Secretion," Fungal Genetics and Biology, 2004, vol. 41 (10), pp. 911-920.
Chaves F., et al., "Molecular Characterization of Resistance to Mupirocin in Methicillin-Susceptible and -Resistant Isolates of *Staphylococcus aureus* from Nasal Samples," Journal of Clinical Microbiology, 2004, vol. 42 (2), pp. 822-824.
Chelly J., et al., "Transcription of the Dystrophin Gene in Human Muscle and Non-Muscle Tissue," Nature, 1988, vol. 333 (6176), pp. 858-860.
Chen C.A., et al., "Universal Primers for Amplification of Mitochondrial Small Subunit Ribosomal RNA-Encoding Gene in *Scleractinan* Corals," Marine Biotechnology, 2000, vol. (2), pp. 146-153.
Chen C.H., et al., Laser Desorption Mass Spectrometry for FastDNA Sequencing [online], Nov. 1994, Retrieved from the Internet:< URL:http://www.ornl.gove/sci/techresources/Human_Genome/publicat/94SANTA/sequencing/seqtoc.shtml>.
Chen J., et al., "A Universal PCR Primer to Detect Members of the Potyviridae and its Use to Examine the Taxonomic Status of Several Members of the Family," Archives of Virology, 2001, vol. 146 (4), pp. 757-766.
Chen N., et al., "The Genomic Sequence of Ectromelia Virus, the Causative Agent of Mousepox," Virology, 2003, vol. 317 (1), pp. 165-186.
Chen R., et al., "Trapping, Detection, and Charge and Mass Measurement of Large Individual Ions (up to 1.1×108 Daltons) by Electrospray Ionization FTICR MS," 42nd ASMS Conference on Mass Spectrometry, 1994.
Chen Y.Z., et al., "A BAC-Based STS-Content Map Spanning a 35-Mb Region of Human Chromosome 1p35-36," Genomics, 2001, vol. 74 (1), pp. 55-70.
Chen Z., et al., "Genetic Mapping of the Cold-Adapted Phenotype of B/Ann Arbor/1/66, the Master Donor Virus for Live Attenuated Influenza Vaccines (FluMist)," Virology, 2006, vol. 345 (2), pp. 416-423.
Chiu N.H., et al., "Mass Spectrometry of Single-Stranded Restriction Fragments Captured by an Undigested Complementary Sequence," Nucleic Acids Research, 2000, vol. 28 (8), pp. E31.
Chmielewicz B., et al., "Development of a PCR-Based Assay for Detection, Quantification, and Genotyping of Human Adenoviruses," Clinical Chemistry, 2005, vol. 51 (8), pp. 1365-1373.
Cho M., et al., "Application of the Ribonuclease P (RNaseP) RNA Gene Sequence for Phylogenetic Analysis of the Genus Saccharomonospora," International Journal of Systematic Bacteriology, 1998, vol. 48 (4), pp. 1223-1230.

(56) References Cited

OTHER PUBLICATIONS

Choi S., et al., "Real-Time PCR Quantification of Human Adenoviruses in Urban Rivers Indicates Genome Prevalence but Low Infectivity," Applied and Environmental Microbiology, 2005, vol. 71 (11), pp. 7426-7433.
Choi Y.K., et al., "Detection and Subtying of Swine Influenza H1N1, H1 N2 and H3N2 Viruses in Clinical Samples Using Two Multiplex RT-PCR Assays," Journal of Virological Methods, 2002, vol. 102 (1-2), pp. 53-59.
Christel L.A., et al., "Rapid, Automated Nucleic Acid Probe Assays Using Silicon Microstructures for Nucleic Acid Concentration," Journal of Biomechanical Engineering, 1999, vol. 121 (1), pp. 22-27.
Claas E.C., et al., "Internally Controlled Real-Time PCT Monitoring of Adenovirus DNA Load inSerum or Plasma of Transplant Recipients," Journal of Clincal Microbiology, 2005, vol. 43 (4), pp. 1738-1744.
Cloney L., et al., "Rapid Detection of mecA in Methicillin Resistant *Staphylococcus aureus* Using Cycling Probe Technology," Molecular and Cellular Probes, 1999, vol. 13 (13), pp. 191-197.
Collins D.W., et al., "Numerical Classification of Coding Sequences," Nucleic Acids Research, 1992, vol. 20 (6), pp. 1405-1410.
Conrads G., et al., "16S-23S rDNA Internal Transcribed Spacer Sequences for Analysis of the Phylogenetic Relationships Among Species of the Genus *Fusobacterium*," International Journal of Systematic and Evolutionary Microbiology, 2002, vol. 52 (2), pp. 493-499.
Contreras-Salazar B., et al., "Up Regulation of the Epstein-Barr Virus (EBV)—Encoded Membrane Protein LMP in the Burkitt's Lymphoma Line Daudi after Exposure to N-Butyrate and after EBV Superinfection," Journal of Virology, 1990, vol. 64 (11), pp. 5441-5447.
Co-pending U.S. Appl. No. 10/318,463, filed Dec. 13, 2002.
Co-pending U.S. Appl. No. 10/323,186, filed Dec. 18, 2002.
Co-pending U.S. Appl. No. 10/323,187, filed Dec. 18, 2002.
Co-pending U.S. Appl. No. 10/324,721, filed Dec. 18, 2002.
Co-pending U.S. Appl. No. 10/521,662, filed Jul. 21, 2003.
Co-pending U.S. Appl. No. 10/807,019, filed Mar. 23, 2004.
Co-pending U.S. Appl. No. 10/845,052, filed May 12, 2004.
Co-pending U.S. Appl. No. 10/964,571, filed Oct. 12, 2004.
Co-pending U.S. Appl. No. 11/209,439, filed Aug. 23, 2005.
Co-pending U.S. Appl. No. 90/010,209, filed Jun. 27, 2008.
Co-pending U.S. Appl. No. 90/010,210, filed Jun. 27, 2008.
Co-pending U.S. Appl. No. 90/010,447, filed Apr. 9, 2009.
Co-pending U.S. Appl. No. 90/010,448, filed Apr. 9, 2009.
Co-pending U.S. Appl. No. 60/639,068, filed Dec. 22, 2004.
Co-pending U.S. Appl. No. 60/648,188, filed Jan. 28, 2005.
Co-pending U.S. Appl. No. 60/369,405, filed Apr. 1, 2002.
Co-pending U.S. Appl. No. 60/397,365, filed Jul. 19, 2002.
Co-pending U.S. Appl. No. 60/431,319, filed Dec. 6, 2002.
Co-pending U.S. Appl. No. 60/443,443, filed Jan. 29, 2003.
Co-pending U.S. Appl. No. 60/443,788, filed Jan. 30, 2003.
Co-pending U.S. Appl. No. 60/447,529, filed Feb. 14, 2003.
Co-pending U.S. Appl. No. 60/453,607, filed Mar. 10, 2003.
Co-pending U.S. Appl. No. 60/461,494, filed Apr. 9, 2003.
Co-pending U.S. Appl. No. 60/470,175, filed May 12, 2003.
Co-pending U.S. Appl. No. 60/501,926, filed Sep. 11, 2003.
Co-pending U.S. Appl. No. 60/509,911, filed Oct. 9, 2003.
Co-pending U.S. Appl. No. 60/604,329, filed Aug. 24, 2004.
Co-pending U.S. Appl. No. 60/615,387, filed Sep. 30, 2004.
Co-pending U.S. Appl. No. 60/701,404, filed Jul. 21, 2005.
Co-pending U.S. Appl. No. 60/705,631, filed Aug. 3, 2005.
Co-pending U.S. Appl. No. 60/720,843, filed Sep. 27, 2005.
Co-pending U.S. Appl. No. 60/747,607, filed May 18, 2006.
Co-pending U.S. Appl. No. 60/771,101, filed Feb. 6, 2006.
Co-pending U.S. Appl. No. 60/773,124, filed Feb. 13, 2006.
Co-pending U.S. Appl. No. 60/891,479, filed Feb. 23, 2007.
Co-pending U.S. Appl. No. 60/941,641, filed Jun. 1, 2007.
Cornel A.J., et al., "Polymerase Chain Reaction Species Diagnostic Assay for Anopheles Quadrimaculatus Cryptic Species (Diptera:Culicidae) Based on Ribosomal DNA ITS2 Sequences," Journal of Medical Entomology, 1996, vol. 33 (1), pp. 109-116.
Couto I., et al., "Development of Methicillin Resistance in Clinical Isolates of *Staphylococcus sciuri* by Transcriptional Activation of the mecA Homologue Native to the Species," Journal of Bacteriology, 2003, vol. 185 (2), pp. 645-653.
Crain P.F., et al., "Applications of Mass Spectrometry to the Characterization of Oligonucleotides and Nucleic Acids," Current Opinion in Biotechnology, 1998, vol. 9 (1), pp. 25-34.
Crawford-Miksza L., et al., "Analysis of 15 Adenovirus Hexon Proteins Reveals the Location and Structure of Seven Hypervariable Regions Containing Serotype-Specific Residues," Journal of Virology, 1996, vol. 70 (3), pp. 1836-1844.
Crawford-Miksza L.K., et al., "Adenovirus Serotype Evolution is Driven by Illegitimate Recombination in the Hypervariable Regions of the Hexon Protein," Virology, 1996, vol. 224 (2), pp. 357-367.
Crawford-Miksza L.K., et al., "Strain Variation in Adenovirus Serotypes 4 and 7a Causing Acute Respiratory Disease," Journal of Clincal Microbiology, 1999, vol. 37 (4), pp. 1107-1112.
Crespillo M., et al., "Mitochondrial DNA Sequences for 118 Individuals from Northeastern Spain," International Journal of Legal Medicine, 2000, vol. 114 (1-2), pp. 130-132.
Cui L., et al., "Contribution of a Thickened Cell Wall and Its Glutamine Nonamidated Component to the Vancomycin Resistance Expressed by *Staphylococcus aureus* Mu50," Antimicrobial Agents and Chemotherapy, 2000, vol. 44 (9), pp. 2276-2285.
Dasen G., et al., "Classification and Identification of Propiolbacteria based on Ribosomal RNA Genes and PCR," Systematic and Applied Microbiology, 1998, vol. 21 (2), pp. 251-259.
De Jong J.C., et al., "Adenoviruses from Human Immunodeficiency Virus-Infected Individuals, Including Two Strains that Represent New Candidate and D, Respectively," Journal of Clincal Microbiology, 1999, vol. 37 (12), pp. 3940-3945.
De La Puente-Redondo V.A., et al., "Comparison of Different PCR Approaches for Typing of *Francisella tularensis* Strains," Journal of Clinical Microbiology, 2000, vol. 38 (3), pp. 1016-1022.
DeForce D.L., et al., "Analysis of Oligonucleotides by ESI-MS," Advances in Chromatography, 2000, vol. 40, pp. 539-566.
DeForce D.L.D., et al., "Characterization of DNA Oligonudeotides by Coupling of Capillary zone Eletrophoresis to Electrospray Ionization Q-TOF Mass Spectrometry," Analytical Chemistry, 1998, vol. 70 (14), Chemistry, 1998, vol. 70 (14), pp. 3060-3068.
Del Blanco Garcia N., et al., "Genotyping of *Francisella tularensis* Strains by Pulsed-field gene Sequencing," Journal of Clinical Microbiology, 2002, vol. 40 (8), pp. 2964-2972.
Del Vecchio V.G., et al., "Molecular Genotyping of Methicillin-Resistant *Staphylococcus aureus* via Fluorophore-Enhanced Repetitive-Sequence PCR," Journal of Clinical Microbiology, 1995, vol. 33 (8), pp. 2141-2144.
Demesure B., et al., "A Set of Universal Primers for Amplification of Polymorphic Non-Coding Regions of Mitochondrial and Chioroplast DNA in Plants," Molecular Ecology, 1995, vol. 4, pp. 129-131.
Denis M., et al., "Development of a Semiquantitative PCR Assay Using Internal Standard and Colorimetricdetection on Microwell Plate for *Pseudorabies virus*," Molecular and Cellular Probes, 1997, vol. 11 (6), pp. 439-448.
Deurenberg R.H., et al., "Rapid Detection of Panton-Valentine Leukocidin from Clinical Isolates of *Staphylococcus aureus* Strains by Real-Time PCR," FEMS Microbiology Letters, 2004, vol. 240 (2), pp. 225-228.
Deurenberg R.H., et al., "The Prevalence of the *Staphylococcus aureus* tst Gene among Community- and Hospital-Acquired Strains and Isolates from Wegener's Granulomatosis Patients," FEMS Microbiology Letters, 2005, vol. 245 (1), pp. 185-189.
Deyde V.M., et al., "Genomic Signature-Based Identification of Influenza A Viruses Using RTPCR/Electro-Spray Ionization Mass Spectrometry (ESI-MS) Technology," PLoS One, 2010, vol. 5 (10), pp. e13293.
Di Guilmi A.M., et al., "Human Adenovirus Serotype 3 (Ad3) and the Ad3 fiber Protein Bind to a 130-kDa Membrane Protein on HLa Cells," Virus Research, 1995, vol. 38 (1), pp. 71-81.

(56) References Cited

OTHER PUBLICATIONS

Dias Neto E., et al., "Shotgun Sequencing of the Human Transcriptome with ORF Expressed Sequence Tags," Proceedings of the National Academy of Sciences, 2000, vol. 97 (7), pp. 3491-3496.
Diep B.A., et al., "Complete Genome Sequence of USA300, an Epidemic Clone of Community Acquired Meticillin-Resistant *Staphylococcus aureus*," Lancet, 2006, vol. 367 (9512), pp. 731-739.
Dinauer D.M., et al., "Sequence-Based Typing of HLA Class II DQB1," Tissue Antigens, 2000, vol. 55 (4), pp. 364-368.
Ding C., et al., "A High-Throughput Gene Expression Analysis Technique Using Compettiive PCR and Matrixassisted Laser Desorption Ionization Time-of-Flight MS," Proceedings of the National Academy of Sciences, 2003, vol. 100 (6), pp. 3059-3064.
Donehower L.A., et al., "The Use of Primers from Highly Conserved Pol Regions to Identify Uncharacterized Retroviruses by the Polymerase Chain Reaction," Journal of Virological Methods, 1990, vol. 28 (1), pp. 33-46.
Donofrio J.C., et al., "Detection of Influenza A and B in Respiratory Secretions with the Polymerase Chain Reaction," PCR Methods and Applications, 19922, vol. 1 (4), pp. 263-268.
Doty P., et al., "Strand Separation and Specific Recombination in Deoxyribonucleic Acids: Physical Chemical Studies," Proceedings of the National Academy of Sciences, 1960, vol. 46 (4), pp. 461-476.
Drosten C., et al., "Identification of a Novel Coronavirus in Patients with Sever Acute Respiratory Syndrome," New England Journal of Medicine, 2003, vol. 348 (20), pp. 1967-1976.
Dubernet S., et al., "A PCR-Based Method for Identification of *Lactobacilli* at to Genus Level," FEMS Microbiology Letters, 2002, vol. 214 (2), pp. 271-275.
Ebner K., et al., "Molecular Detection and Quantitative Analysis of the Entire Spectrum of Human Advenviruses by a Two-Reaction Real-Time PCR Assay," Journal of Clinical Microbiology, 2005, vol. 43 (7), pp. 3049-3053.
Ebner K., et al., "Typing of Human Adenoviruses in Specimens from Immunosuppressed Patients by PCR-Fragment Length Analysis and Real-Time Quantitative PCR," Journal of Clinical Microbiology, 2006, vol. 44 (8), pp. 2808-2815.
Echavarria M., et al., "Detection of Adenoviruses (AdV) in Culture-Negative EnvironmentalSamples by PCR During an AdV—Associated Respiratory Disease Outbreak," Journal of Clinical Microbiology, 2000, vol. 38 (8), pp. 2982-2984.
Echavarria M., et al., "PCR Method for Detection of Adenovirus in Urine of Healthy and Human Immunodeficiency Virus-Infected Individuals," Journal of Clinical Microbiology, 1998, vol. 36 (11), pp. 3323-3326.
Echavarria M., et al., "Prediction of Severe Disseminated Adenovirus Infection by Serum PCR," Lancet, 2001, vol. 358 (9279), pp. 384-385.
Echavarria M., et al., "Rapid Detection of Adenovirus in Throat Swab Specimens by PCR During Respiratory Disease Outbreaks among Military Recruits," Journal of Clinical Microbiology, 2003, vol. 41 (2), pp. 810-812.
Echavarria M., et al., "Use of PCR to Demonstrate Presence of Adenovirus Species B, C, or F as Well as Coinfection with Two Adenovirus Species in Children with Flu-Like Symptoms," Journal of Clinical Microbiology, 2006, vol. 44 (2), pp. 625-627.
Ecker D.J., et al., "Ibis T5000: A Universal Biosensor Approach for Microbiology," Nature Reviews Microbiology, 2008, vol. 6 (7), pp. 553-558.
Ecker D.J., et al., "Rapid Identification and Strain-Typing of Respiratory Pathogens for Epidemic Surveillance," Proceedings of the National Academy of Sciences, 2005, vol. 102 (22), pp. 8012-8017.
Ecker D.J., et al., "The Ibis T5000 Universal Biosensor. An Automated Platform for Pathogen Identification and Strain Typing," Journal of the Association for Laboratory Automation, 2006, vol. 11 (6), pp. 341-351.
Ecker Supporting Information [online], May 23, 2005 [retrieved on Jul. 31, 2011]. Retrieved from the Internet< URL: http://www.pnas.org/content/102/22/8012/suppl/DC1>.

Edwards K.M., et al., "Adenovirus Infections in Young Children," Pediatrics, 1985, vol. 76 (3), pp. 420-424.
Ellis J.S., et al., "Molecular Diagnosis of Influenza," Reviews in Medical Virology, 2002, vol. 12 (6), pp. 375-389.
Ellis J.S., et al., "Multiplex Reverse Transcription-PCR for Surveillance of Influenza A and B Viruses in England and Wales in 1995 and 1996," Journal of Clinical Microbiology, 1997, vol. 35(8), pp. 2076-2082.
Elnifro E.M., et al., "PCR and Restriction Endonuclease Analysis for Rapid Identification of Adenovirus subgenera," Journal of Clinical Microbiology, 2000, vol. 38 (6), pp. 2055-2061.
Elsayed S., et al., "Development and Validation of a Molecular Beacon Probe-Based Real-Time Polymerase Chain Reaction Assay for Rapid Detection of Methicillin Resistance in *Staphylococcus aureus*," Archives of Pathology and Laboratory Medicine, 2003, vol. 127 (7), pp. 845-849.
EMBL "*Arabidopsis thaliana* T-DNA Flanking Sequence, Left Border, Clone 346C06," Accession No. AJ552897, Mar. 29, 2003.
EMBL "Dog (Clone: CXX.147) Primer for STS 147, 3" End, Sequence Tagged Site," Accession No. L15697, Mar. 4, 2000.
EMBL "Sequence 10 from Patent US 6563025," Accession No. AR321656, Aug. 18, 2003.
EMBL "Human, muscle, Mitochondrial Mutant, 22 nt, segment 2 of 2," Accession No. S90302, Sep. 1, 2004.
EMBL "Synthetic Construct DNA, Reverse Primer for Human STS sts-AA031654 at 1p36" Accession No. AB068711, May 21, 2003.
Enright M.C., et al., "A Multilocus Sequence Typing Scheme for *Streptococcus pneumoniae*: Identification of Clones Associated with Serious Invasive Disease," Microbiology, 1998, vol. 144 (Pt 11), pp. 3049-3060.
Enright M.C., et al., "Multilocus Sequence Typing for Characterization of Methicillin-Resistant and Methicillin-Susceptible Clones of *Staphylococcus aureus*," Journal of Clinical Microbiology, 2000, vol. 38 (3), pp. 1008-1015.
Enright M.C., et al., "Multilocus Sequence Typing of *Streptococcus pyogenes* and theRelationships between Emm Type and Clone," Infection and Immunity, 2001, vol. 69 (4), pp. 2416-2427.
Enright M.C., et al., "The Evolutionary Histroy of Methicillin-Resistant *Staphylococcus aureus* (MRSA)," Proceedings of the National Academy of Sciences, 2002, vol. 99 (11), pp. 7687-7692.
Enright M.S., "The Evolution of a Resistant Pathogen—the case of MRSA," Current Opinion in Pharmacology, 2003, vol. 3 (5), pp. 474-479.
Eremeeva M.E., et al., "Evaluation of a PCR Assay for Quantitation of *Rickettsia rickettsii* and Closely Releated Spotted Fever Group *Rickettsiae*," Journal of Clinical Microbiology, 2003, vol. 41 (12), pp. 5466-5472.
Erlich H.A., Ed., PCR Technology: Principles and Applications for DNA Amplification, W.H. Freeman and Company, 1989.
Esmans E.L., et al., "Liquid Chromatography-Mass Spectrometry in Nucleoside, Nucleotide and Modified Nucleotide Characterization," Journal of Chromatography, 1998, vol. 794, pp. 109-127.
Eugene-Ruellan G., et al., "Detection of Respiratory Syncytial Virus A and B and Parainfluenzavirus 3 Sequences in Respiratory Tracts of Infants by a Single PCR with Primers Targeted to the L-Polymerase Gene and Differential Hybridization," Journal of Clinical Microbiology, 1998, vol. 36 (3), pp. 796-801.
Evans P., et al., "Practical Algorithms for Universal DNA Primer Design: An Exercise in Algorithm Engineering," Currents in Computational Molecular Biology, 2001, pp. 25-26.
Ex Parte Re-Examination Certificate for U.S. Appl. No. 90/010,209 mailed Jul. 7, 2009.
Ex Parte Re-Examination Certificate for U.S. Appl. No. 90/010,210, mailed Dec. 28, 2010.
Ex Parte Re-Examination Certificate for U.S. Appl. No. 90/010,447 mailed Feb. 15, 2011.
Examiner Interview Summary Report mailed Oct. 3, 2005 for U.S. Appl. No. 10/326,046, filed Dec. 18, 2002.
Examiner Interview Summary Report mailed Nov. 6, 2008 for U.S. Appl. No. 10/728,486, filed Dec. 5, 2003.
Examiner Interview Summary Report mailed Aug. 10, 2004 for U.S. Appl. No. 09/798,007, filed Mar. 2, 2001.

(56) References Cited

OTHER PUBLICATIONS

Examiner Interview Summary Report mailed Aug. 10, 2004 for U.S. Appl. No. 09/891,793, filed Jun. 26, 2001.
Examiner Interview Summary Report mailed Aug. 10, 2004 for U.S. Appl. No. 10/156,608, filed May 24, 2002.
Examiner Interview Summary Report mailed Aug. 10, 2004 for U.S. Appl. No. 10/326,642, filed Dec. 18, 2002.
Examiner Interview Summary Report mailed May 19, 2003 for U.S. Appl. No. 09/891,793, filed Jun. 26, 2001.
Examiner Interview Summary Report mailed Oct. 24, 2008 for U.S. Appl. No. 11/582,859, filed Oct. 17, 2006.
Examiner Interview Summary Report mailed Feb. 27, 2006 for U.S. Appl. No. 10/326,644, filed Dec. 18, 2002.
Examiner Interview Summary Report mailed Jan. 27, 2006 for U.S. Appl. No. 10/323,211, filed Dec. 18, 2002.
Examiner Interview Summary Report mailed May 28, 2008 for U.S. Appl. No. 10/660,998, filed Sep. 12, 2003.
Examiner Interview Summary Report mailed Oct. 28, 2008 for U.S. Appl. No. 11/331,987, filed Jan. 13, 2006.
Examiner Interview Summary Report mailed Oct. 29, 2008 for U.S. Appl. No. 11/331,978, filed Jan. 13, 2006.
Examiner Interview Summary Report mailed Oct. 29, 2009 for U.S. Appl. No. 10/660,122, filed Sep. 11, 2003.
Examiner Interview Summary Report mailed Jul. 31, 2006 for U.S. Appl. No. 10/326,643, filed Dec. 18, 2002.
Extended European Search Report for Application No. EP10175659.1, mailed on Feb. 21, 2011, 8 pages.
Extended European Search Report for Application No. EP10179789.2, mailed on Mar. 22, 2011, 9 pages.
Extended European Search Report for Application No. EP10179791.8, mailed on Mar. 17, 2011, 7 pages.
Extended European Search Report for Application No. EP10179795.9, mailed on Mar. 22, 2011, 9 pages.
Facklam R., et al., "Emm Typing and Validation of Provisional M Types for Group A Streptococci," Emerging Infectious Diseases, 1999, vol. 5 (2), pp. 247-253.
Fang H., et al., "Rapid Screening and Identification of Methicillin-Resistant *Staphylococcus aureus* from Clinical Samples by Selective-Broth and Real-Time PCR Assay," Journal of Clinical Microbiology, 2003, vol. 41 (7), pp. 2894-2899.
Farlow J., et al., "*Francisella tularensis* Strain Typing Using Multiple-Locus, Variable-Number Tandem Repeat Analysis," Journal of Critical Microbiology, 2001, vol. 39 (9), pp. 3186-3192.
Farrell D.J., "The Reliability of Microscan Conventional and Rapid Panels to Identify *Staphylococcus aureus* and Detect Methicillin Resistance: An Evaluation Using the Tube Coagulase Test and mecA PCR," Pathology, 1997, vol. 29 (4), pp. 406-410.
Fedele C.G., et al., "Multiplex Polymerase Chain Reaction for the Simultaneous Detection and Typing of Polyomavirus JC, BK and SV40 DNA in Clinical Samples," Journal of Virological Methods, 1999, vol. 82 (2), pp. 137-144.
Fedele C.G., et al., "Quantitation of Polyomavirus DNA by a Competitive Nested Polymerase Chain Reaction," Journal of Virological Methods, 2000, vol. 88 (1), pp. 51-61.
Feng P., "Impact of Molecular Biology on the Detection of Food Pathogens," Molecular Biotechnology, 1997, vol. 7 (3), pp. 267-278.
Figueiredo L.M., et al., "Identification of Brazilian *Flavivirus* by a Simplified Reverse Transcription-Polymerase Chain Reaction Method Using Flavivirus Universal Primers," American Journal of Tropical Medicine and Hygiene, 1998, vol. 59 (3), pp. 357-362.
Final Office Action mailed Aug. 6, 2010 for U.S. Appl. No. 11/929,910, filed Oct. 30, 2007.
Final Office Action mailed Jul. 8, 2010 for U.S. Appl. No. 12/326,800, filed Dec. 2, 2008.
Final Office Action mailed May 12, 2010 for U.S. Appl. No. 11/674,538, filed Feb. 13, 2007.
Final Office Action mailed Apr. 14, 2011 for U.S. Appl. No. 12/049,949, filed Mar. 17, 2008.
Final Office Action mailed Oct. 14, 2009 for U.S. Appl. No. 10/943,344, filed Sep. 17, 2004.
Final Office Action mailed Nov. 17, 2009 for U.S. Appl. No. 11/582,875, filed Oct. 17, 2006.
Final Office Action mailed Feb. 18, 2010 for U.S. Appl. No. 10/754,415, filed Jan. 9, 2004.
Final Office Action mailed Nov. 20, 2009 for U.S. Appl. No. 11/331,987, filed Jan. 13, 2006.
Final Office Action mailed Jun. 23, 2010 for U.S. Appl. No. 11/930,017 filed Oct. 30, 2007.
Final Office Action mailed Feb. 26, 2009 for U.S. Appl. No. 11/582,863, filed Oct. 17, 2006.
Final Office Action mailed Jan. 30, 2009 for U.S. Appl. No. 10/844,938, filed May 12, 2004.
Flora J.W., et al, "Dual-Micro-ESI Source for Precise Mass Determination on a Quadrupole Time-of-Flight Mass Spectrometer for Genomic and Proteomic Applications," Analytical and Bioanalytical Chemistry, 2002, vol. 373 (7), pp. 538-546.
Fong W.K., et al., "Rapid Solid-Phase Immunoassay for Detection of Methicillin-Resistant*Staphylococcus aureus* Using Cycling Probe Technology," Journal of Clinical Microbiology, 2000, vol. 38 (7), pp. 2525-2529.
Fox A., et al., "Identification and Detection of Bacteria: Electrospray MS-MS Versus Derivatization/GC-MS," Proceedings of the ERDEC Scientific Conference on Chemical and Biological Defense Research, Aberdeen Proving Ground, MD, Nov. 15-18, 1994, pp. 39-44.
Fox A., et al., "Report of the Bioterrorism Workshop," Journal of Microbiological Methods, 2002, vol. 51 (3), pp. 247-254.
Fox J.P., et al., "The Virus Watch Program: A Continuing Surveillance of Viral Infections in Metropolitan New York Families," American Journal of Epidemiology, 1969, vol. 89 (1), pp. 25-50.
Fox K.F., et al., "Identification of *Brucella* by Ribosomal-Spacer-Region PCR and Differentiation of *Brucell* from Other *Brucella* Spp. Pathogenic for Humans by Carbohydrate Profiles," Journal of Clinical Microbiology, 1998, vol. 36 (11), pp. 3217-3222.
Francois J.C., et al., "Sequence-Specific Recognition and Cleavage of Duplex DNA via Triple-Helix Formation by Oligonucleotides Covalently Linked to a Phenanthroline-Copper Chelate," Proceedings of the National Academy of Sciences, 1989, vol. 86 (24), pp. 9702-9706.
Francois P., et al., "Rapid Detection of Methicillin-Resistant *Staphylococcus aureus* Directly from Sterile or Nonsterile Clinical Samples by a New Molecular Assay," Journal of Clinical Microbiology, 2003, vol. 41 (1), pp. 254-260.
Fraser C.M., et al., "The Mimimal Gene Complement of *Mycoplasma genitalium*," Science, 1995, vol. 270 (5235), pp. 397-403.
Freiberg C., et al., "Genome-Wide mRNA Profiling: Impact on Compound Evaluation and Target Identification in Anti-Bacterial Research," Targets, 2002, vol. 1 (1), pp. 20-29.
Freymuth F., et al., "Comparison of Multiplex PCR Assays and Conventional Techniques for the Diagnostic of Respiratory Virus Infections in Children Admitted to Hospital With an Acute Respiratory Illness," Journal of Medical Virology, 2006, vol. 78 (11), pp. 1498-1504.
Freymuth F., et al., "Detection of Respiratory Syncytial Virus, Parainfluenzavirus 3, Adenovirus Andrhinovirus Sequences in Respiratory Tract of Infants by Polymerase Chain Reaction and Hybridization," Clinical and Diagnostic Virology, 1997, vol. 8 (1), pp. 31-40.
Fuerstenau S.D., et al., "Molecular Weight Determination of Megadalton DNA Electrospray Ions Using Charge Detection Time-of-flight Mass Spectrometry," Rapid Communications in Mass Spectrometry, 1995, vol. 9 (15), pp. 1528-1538.
Fujimoto T., et al., "Single-Tube Multiplex. PCR for Rapid and Sensitive Diagnosis of Subgenus B and Other Subgenera Adenoviruses in Clinical Samples," Microbiology and Immunology, 2000, vol. 44 (10), pp. 821-826.
Fujimura S., et al., "Characterization of the mupA Gene in Strains of Methicillin-Resistant *Staphylococcus aureus* with a Low Level of Resistance to Mupirocin," Antimicrobial Agents and Chemotheraphy, 2001, vol. 45 (2), pp. 641-642.
Fujimura S., et al., "Isoleucyl-tRNA Synthetase Mutations in *Staphylococcus aureus* ClinicalIsolates and In Vitro Selection of

(56) References Cited

OTHER PUBLICATIONS

Low-Level Mupirocin-Resistant Strains," Antimicrobial Agents and Chemotheraphy, 2003, vol. 47 (10), pp. 3373-3374.
Fujioka S., et al., "Analysis of Enterovirus Genotypes using Single-Strand Conformation Polymorphisms of Polymerase Chain Reaction Product," Journal of Virological Methods, 1995, vol. 51 (2-3), pp. 253-258.
Gabriel M.N., et al., "Improved mtDNA Sequence Analysis of Forensic Remains using a "Mini-Primer Set" Amplification Strategy," Journal of Forensic Sciences, 2001, vol. 46 (2), pp. 247-253.
Gall J.G., et al., "Construction and Characterization of Hexon-Chimeric Adenoviruses: Specification of Adenovirus Serotype," Journal of Virology, 1998, vol. 72 (12), pp. 10260-10264.
Gammelin M., et al., "Two Subtypes of Nucleoproteins (NP) of Influenza A Viruses," Virology, 1989, vol. 170 (1), pp. 71-80.
Garcia S., et al., "Quantitative Real-Time PCR Detection of Rift Valley Fever Virus and Its Application to Evaluation of Antiviral Compounds," Journal of Clinical Microbiology, 2001, vol. 39 (12), pp. 4456-4461.
Garcia-Martinez J., et al., "Use of the 16s-23s Ribosomal Genes Spacer Region in Studies of Prokaryotic Diversity," Journal of Microbiological Methods, 1999, vol. 36 (1-2), pp. 55-64.
Gattermann N., et al., "Heteroplasmic Point Mutations of Mitochondrial DNA Affecting Subunit I of Cytochrome c Oxidise in Two Patients with Acquired Idiopathic Siderblastic Anemia," Blood, 1997, vol. 90 (12), pp. 4961-4972.
Gaydos C.A., et al., "Adenovirus Vaccines in the U.S. Military," Military Medicine, 1995, vol. 160 (6), pp. 300-304.
Geha D.J., et al., "Multiplex PCR for Identification of Methicillin-Resistant Staphylococci in the Clinical Laboratory," Journal of Clinical Microbiology, 1994, vol. 32 (7), pp. 1768-1772.
Genbank, "*Acinetobacter* Genomosp. 10 Strain CIP 70.12 RNA Polymerase Subunit B (rpoB) Gene, Complete Cds," Accession No. 78099429, Mar. 11, 2006.
Genbank, "Bovine Parainfluenza Virus 3 Strain Shipping Fever, Complete Genome," Accesion.No. AF178655, Sep. 19, 2000.
Genbank, "*Clostridium tetani* E88, Complete Genome," Accession No. AE015927.1, Feb. 4, 2003.
Genbank, "{Deletion 6} [Human, Muscle, Mitochondrial Mutant, 22 nt, Segment 2 of 2]," Accession No. S90302.1, Jun. 10, 1992.
Genbank, "*E. coli* Operon rpoBC Coding for the Beta- and Beta"-Subunits of RNA Polymerase (Genes rpoC and rpoB), and Genes rplL, rlpJ, rplA, and rplK Coding for 50S Ribosomal Subunit Proteins L7/L12, L10, L1, and L11, Respectively. (Map position 89-90 min.), Accession No. 42813, Feb. 28, 1992.
Genbank, "*E. coli* 16S Ribosomal RNA," Accession No. 174375, Aug. 11, 1995.
Genbank, "*E. coli* Open Reading Frame Upstream of Leu Operon," Accession No. M21150, Sep. 15, 1990.
Genbank, "*E. coli* rRNA Operon (rrnB) Coding for Glu-tRNA-2, 5S, 16S and 23S rRNA," Accession No. 147581, Sep. 14, 1992.
Genbank, "*Enterococcus malodoratus* Strain ATCC43197 Elongation Factor Tu (tufA) Gene, Partial Cds," Accession No. AF274728, Dec. 11, 2000.
Genbank "*Escherichia coli* str. K-12 substr. MG1655, Complete Genome," Accession No. NC000913, Oct. 15, 2001.
Genbank, "*Homo sapiens* Haplotype V Mitochondrion, Complete Genome", Accession No. AF381990.1, Dec. 28, 2001.
Genbank, "Human Adenovirus Type 4 Hexon Gene," for Accession No. X84646, Jun. 30, 1995.
Genbank, "Human *Coronavirus* 229E, Complete Genome," Accession No. AF304460, Jul. 11, 2001.
Genbank, "Human Isolate L34 Mitochondrion D-loop Region", Accession No. U08081.1, Aug. 16, 1994.
GenBank, "il11b08.y1 Human insulinoma *Homo sapiens* cDNA clone Image:6029534 5- similar to SW:COX3_HUMAN P00414 Cytochrome C Oxidase Polypeptide III ;, mRNA sequence", Accession No. BQ581956.1, Jun. 20, 2002.

Genbank, "Influenza B Virus B/Panama/45/90 Polymerase (PB2) mRNA, Complete Cds", Accession No. AF005737, Oct. 4, 1997, pp. 1-3.
Genbank, "Mastadenovirus h7 Hexon Gene," Accession No. Z48571, Apr. 18, 2005.
GenBank, "or72a01.s1 NCI_CGAP_Lu5 *Homo sapiens* cDNA Clone Image:1601352 3- similar to SW:COX1_HUMAN P00395 Cytochrome C Oxidase Polypeptide I ;, mRNA sequence", Accession No. AI002209.1, Jun. 10, 1998.
Genbank "*Staphylococcus aureus* RN4220 ErmC Gene, Partial Cds," Accession No. 18542231, Sep. 16, 2003.
Genbank "*Staphylococcus aureus* Strain MSSA476, Complete Genome," Accession No. BX571857.1, Jun. 24, 2004.
Genbank, "*Staphylococcus aureus* Subsp. Aureus Mu50, Complete Genome," Accession No. 15922990, Oct. 4, 2001.
Genbank "*Staphylococcus aureus* Subsp. Aureus MW2, Complete Genome," Accession No. G121281729, May 31, 2002.
Genbank, "*Staphylococcus epidermidis* ATCC 12228, Complete Genome," Accession No. AE015929.1, Jan. 2, 2003.
Genbank "*Streptococcus agalactiae* 2603V/R, Complete Genome," Accession No. AE009948.1, Aug. 28, 2002.
Genbank, "*Streptococcus anginosus* Elongation Factor Tu (tuf) Gene, Partial cds," Accession No. AF276257.1, Jul. 1, 2001.
Genbank, "*Streptococcus pneumoniae* Isolate 95.1In00S DNA Gyrase Subunit B (gyrB) Gene, Complete Cds," Accession No. 73916349, Sep. 30, 2005.
Genbank, "*Streptococcus pyogenes* Strain MGAS8232, Complete Genome," Accession No. AE009949.1, Apr. 3, 2002.
Genbank, "Venezuelan Equine Encephalitis Virus Nonstructural Polyprotein and Structural Polyprotein Genes, Complete Cds," Accession No. AF375051.1, Jun. 26, 2001.
Gendel S.M., "Computational Analysis of the Specificity of 16S rRNA-Derived Signature Sequencesfor Identifying Food-Related Microbes," Food Microbiology, 1996, vol. 13, pp. 1-15.
Gibb T.R., et al., "Development and Evaluation of a 5" Fluorogenic Nuclease Assay to Detect and Differentiate Between Ebola Virus Subtypes Zaire and Sudan," Journal of Clinical Microbiology, 2001, vol. 39 (11), pp. 4125-4130.
Gilbert N., et al., "Comparison of Commercial Assays for the Quantitation of HBV DNA Load in Healthcare Workers :Calibration Differences," Journal of Virological Methods, 2002, vol. 100 (1-2), pp. 37-47.
Giles R.E., et al., "Maternal Inheritance of Human Mitochondrial DNA," Proceedings of the National Academy of Sciences, 1980, vol. 77 (11), pp. 6715-6719.
Gill S.R., et al., "Insights on Evolution of Virulence and Resistance from the Complete Genome Analysis of an Early Methicillin-Resistant *Staphylococcus aureus* Strain and a Biofilm-Producing Methicilin-Resistant *Staphylococcus epidemidis* Strain," Journal of Bacteriology, 2005, vol. 187 (7), pp. 2426-2438.
Gilliland G., et al., "Analysis of Cytokine mRNA and DNA: Detection and Quantitation by Competitive Chain Reaction," Proceedings of the National Academy of Sciences, 1990, vol. 87 (7), pp. 2725-2729.
Ginther C., et al., "Identifying Individuals by Sequencing Mitochondrial DNA from Teeth," Nature Genetics, 1992, vol. 2 (2), pp. 135-138.
Gjoen K.V., et al., "Specific Detection of Coxsackie Viruses A by the Polymerase Chain Reaction," Clinical and Diagnostic Virology, 1997, vol. 8 (3), pp. 183-188.
Golden M.R., et al., "Pilot Study of COBAS PCR and Ligase Chain Reaction for Detection of Rectal Infections Due to Chlamydia Trachomatis," Journal of Clinical Microbiology, 2003, vol. 41 (5), pp. 2174-2175.
Goto K., et al., "Applications of the Partial 16S rDNA Sequence as an Index for Rapid Identification of Species in the Genus *Bacillus*," Journal of General and Applied Microbiology, 2000, vol. 46 (1), pp. 1-8.
Gravet A., et al., "Characterization of a Novel Structural Member, LukE-LukD, of the Bi-Component Staphylococcal Leucotoxins Family," FEBS Letters, 1998, vol. 436 (2), pp. 202-208.

(56) References Cited

OTHER PUBLICATIONS

Gray G.C., et al., "Adult Adenovirus Infections: Loss of Orphaned Vaccines Precipitates Military Respiratory Disease Epidemics," Clinical Infectious Diseases, 2000, vol. 31, pp. 663- 670.

Greenberg B.D., et al., "Intraspecific Nucleotide Sequence Variability Surrounding the Origin of Replicationin Human Mitochondrial DNA," Gene, 1983, vol. 21, pp. 33-49.

Griffey, et al., "Detection of Base Pair Mismatches in Duplex DNA and RNA Oligonucleotides Using Electrospray Mass Spectrometry," SPIE, 1997, vol. 2985, pp. 82-86.

Griffin T.J., et al., "Direct Genetic Analysis by Matrix-Assisted Laseer Desorption/Ionization Mass Spectrometry," Proceedings of the National Academy of Sciences, 1999, vol. 96 (11), pp. 6301-6306.

Griffin T.J., et al., "Single-Nucleotide Polymorphism Analysis by Maldi-TOF Mass Spectrometry," Trends in Biotechnology, 2000, vol. 18 (2), pp. 77-84.

Grondahl B., et al., "Rapid Identification of Nine Microorganisms Causing Acute Respiratory TractInfections by Single-Tube Multiplex Reverse Transcription-PCR: Feasibility Study," Journal of Clinical Microbiology, 1999, vol. 37 (1), pp. 1-7.

Grundmann H., et al., "Emergence and Resurgence of Meticillin-Resistant *Staphylococcus aureus* as a Public-Health Threat," Lancet, 2006, vol. 368 (9538), pp. 874-885.

Grzybowski T., et al., "Extremely High Levels of Human Mitochondrial DNA Heteroplasmy in Single Hair Roots," Electrophoresis, 2000, vol. 21 (3), pp. 548-553.

Gu Z., et al., "Multiplexed, Real-Time PCR for Quantitative Detection of Human Adenovirus," Journal of Clinical Microbiology, 2003, vol. 41 (10), pp. 4636-4641.

Guatelli J.C., et al., "Nucleic Acid Amplification In Vitro: Detection of Sequences with Low Copy Numbers and Application to Diagnosis of Human Immunodeficiency Virus Type 1 Infection," Clinical Microbiology Reviews, 1989, vol. 2 (2), pp. 217-226.

Haff L.A., et al., "Multiplex Genotyping of PCR Products with Mass Tag-Labeled Primers," Nucleic Acids Research, 1997, vol. 25 (18), pp. 3749-3750.

Hahner S., et al., "Analysis of Short Tandem Repeat Polymorphisms by Electrospray Ion Trap Mass Spectrometry," Nucleic Acids Research, 2000, vol. 28 (18), pp. E82.1-E82.8.

Haines J.D., et al., "Medical Response to Bioterrorism: Are We Prepared," Journal of Oklahoma State Medical Association, 2000, vol. 93, pp. 187-196.

Hall T.A., et al., "Base Composition Analysis of Human Mitochondrial DNA Using Electrospray Ionization Mass Spectrometry: A Novel Tool for the Identification and Differentiation of Humans," Analytical Biochemistry, 2005, vol. 344 (1), pp. 53-69.

Hamdad F., et al., "Detection of Methicillin/Oxacillin Resistance and Typing in Aminoglycoside-Susceptible Methicillin-Resistant and Kanamycin-Tobramycin-Resistant Methicillin-Susceptible," Microbial Drug Resistance, 2006, 12 (3), 177-185.

Hamel S., et al., "Consensus PCR and Microarray for Diagnosis of the Genus Species, and Methicillin Resistance," Biotechniques, 2001, vol. 31 (6), pp. 1364-1372.

Hammerle T., et al., "A Sensitive PCR Assay Systems for the Quantitation of Viral Genome Equivalents:Hepatitis C Virus (HCV)," Archives of Virology, 1996, vol. 141 (11), pp. 2103-2114.

Hannis J.C., et al., "Accurate Characterization of the Tyrosine Hydroxylase Forensic Allele 9.3 through Development of Electrospray Ionization Fourier Transform Ion Cyclotron Resonance Mass Spectrometry," Rapid Communications in Mass Spectrometry, 1999, vol. 13 (10), pp. 954-962.

Hannis J.C., et al., "Detection of Double-Stranded PCR Amplicons at the Attomole Level Electrosprayed from Low Nanomolar Solutions using FT-ICR Mass Spectrometry," Fresenius Journal of Analytical Chemistry, 2001, vol. 369 (3-4), pp. 246-251.

Hannis J.C., et al., "Genotyping Complex Short Tandem Repeats Using Electrospray Ionzation Fourier Transform Ion Cyclotron Resonance Multi-Stage Mass Spectrometry," Proceedings of SPIE, 2000, vol. 3926, pp. 36-47.

Hannis J.C., et al., "Genotyping Short Tandem Repeats Using Flow Injection and Electrospray Ionization, Fourier Transform Ion Cyclotron Resonance Mass Spectrometry," Rapid Communications in Mass Spectrometry, 2001, vol. 15 (5), pp. 348-350.

Hannis J.C., et al., "Nanoelectrospray Mass Spectrometry Using Non-Metalized, Tapered (50 .mu.m) Fused-silica Capillaries," Rapid Communication in Mass spectrometry, 1998, vol. 12, pp. 443-448.

Hanssen A.M., et al., "Sccmecin Staphylococci: Genes on the Move," FEMS Immuol Medical Microbiol, 2006, vol. 46, pp. 8-20.

Hasebe F. et al., "Combined Detection and Genotyping of Chikungunya Virus by a Specific Reverse Transcription-Polymerase Chain Reaction," Journal of Medical Virology, 2002, vol. 67 (3), (3), pp. 370-374.

Hassan A.A., et al., "Inter- and Intraspecies Variations of the 16S-23S rDNA Intergenic Spacer Region of Various Streptococcal Species," Systematic and Applied Microbiology, 2003, vol. 26 (1), pp. 97-103.

Haugland R.A., et al., "Identification of Putative Sequence Specific PCR Primers for Detection of the Toxygenic Fungal Species Stachybotrys Chartarum," Molecular and Cellular Probes, 1998, vol. 12 (6), pp. 387-396.

Hayashi H., et al., "Phylogenetic Analysis of the Human Gut Microbiota Using 16S rDNA Clone Libraries and Strictly Anaerobic Culture-based Methods," Journal of Microbiology, Immunology, 2002, vol. 46 (8), pp. 535-548.

He L., et al, "Development of a Capillary High-performance Liquid Chromatography Tandem Mass Spectrometry System Using SWIFT Technology in an Ion Trap/Refelction Time-of-flight Mass Spetrometer," Biochemical and Biophysical Research Communications, 1997, vol. 11, pp. 1739-1748.

Heim A., et al., "Rapid and Quantitative Detection of Human Adenovirus DNA by Real-Time PCR," Journal of Medical Virology, 2003, vol. 70, pp. 228-239.

Henchal E.A., et al., "Sensitivity and Specificity of a Universal Primer Set for the Rapid Diagnosis of Dengue Virus Infections by Polymerase Chain Reaction and Nucleic Acid Hybridization," American Journal of Tropical Medicine and Hygiene, 1991, vol. 45 (4), pp. 418-428.

Herrmann B., et al., "Differentiation of *Chiamydia* spp. by Sequence Determination and Restriction Endonuclease Cleavage of RNase P RNA Genes," Journal of Clinical Microbiology, 1996, vol. 34 (8), pp. 1897-1902.

Higgins G.S., et al., "Competitive Oligonucleotide Single-base Extension Combined with Mass Spectrometric Detection for Mutation Screening," Biotechniques, 1997, vol. 23 (4), pp. 710-714.

Higgins J.A., et al., "Sensitive and Rapid Identification of Biological Threat Agents," Annals of the New York Academy of Sciences, 1999, vol. 894, pp. 130-148.

Hill F., et al., "Polymerase Recognition of Synthetic Oligodeoxyribonucleotides Incorporating Degenerate Pyrimidine and Purine Bases," Proceedings of the National Academy of Sciences, 1998, vol. 95, pp. 4258-4263.

Hiramatsu K., et al., "The Emergence and Evolution of Methicillin-Resistant *Staphylococcusaureus*," Trends Microbiology, 2001, vol. 9 (10), pp. 486-493.

Hodgson J.E., et al., "Molecular Characterization of the Gene Encoding High-Level Mupirocin Resistancein *Staphylococcus aureus* J2870," Antimicrobial Agents and Chemotherapy, 1994, vol. 38 (5), pp. 1205-1208.

Hoffman E., et al., "Rescue of Influenza B Virus from Eight Plasmids," Proceedings of the National Academy of Sciences, 2002, vol. 99 (17), pp. 11411-11416.

Hoffmann E., et al., "Universal Primer Set for the Full-Length Amplification of all Influenza A Viruses," Archives of Virology, 2001, vol. 146 (12), pp. 2275-2289.

Hofstadler S.A., et al., "TIGER: Thre Universal Biosensor," International Journal of Mass Spectrometry, 2005, vol. 242, pp. 23-41.

Holden M.T., et al., "Complete Genomes of Two Clinical *Staphylocuccus aureus* Strain: Evidence for the Rapid Evolution of Virulence and Drug Resistance," Proceedings of the National Academy of Sciences, 2004, vol. 101 (26), pp. 9786-9791.

(56) References Cited

OTHER PUBLICATIONS

Holland M.M., et al., "Mitochondrial DNA Sequence Analsysis—Validation and Use for Forensic Casework," Forensic Science Review, 1999, vol. 11 (1), pp. 22-50.
Holland M.M., et al., "Mitochondrial DNA Sequence Analysis of Human Skeletal Remains: Identification of Remains from the Vietnam War," Journal of Forensic Sciences, 1993, vol. 38 (3), pp. 542-553.
Holm L., et al., "Removing Near-Neighbour Redundancy from Large Protein Sequence Collections," Bioinformatics, 1998, vol. 14 (5), pp. 423-429.
Holmes E.C., et al., "Whole-Genome Analysis of Human Influenza A Virus Reveals Multiple Persistent Lineages and Reassortment among Recent H3N2 Viruses," Public Library of Science Biology, 2005, vol. 3 (9), pp. 1579-1589.
Honda K., et al., "Universal Method of Hypersensitive Nested PCR Toward Forensic DNA typing," International Congress Series, 1998, vol. 7, pp. 28-30.
Hongoh Y., et al., "Evaluation of Primers and PCR Conditions for the Analysis of 16s rRNA Genes froma Naturalenvironment," FEMS Microbiology Letters, 2003, vol. 221 (2), pp. 299-304.
Hood E., et al., "Chemical and Biological Weapons: New Questions, New Answers," Environmental Health Perspectives, 1999, vol. 107 (12), pp. 931-932.
Houng H.S., et al., "Rapid Type-Specific Diagnosis of Adenovirus Type 4 Infection Using a Hexon-Based Quantitative Fluorogenic PCR," Diagnostic Microbiology and Infectious Disease, 2002, vol. 42 (4), pp. 227-236.
Howell N., et al., "Persistent Heteroplasmy of a Mutation in the Human mtDNA Control Region: Hypermutation as an Apparent Consequence of Simple-Repeat Expansion/Contraction," American Journal of Human Genetics, 2000, vol. 66 (5), pp. 1589-1598.
Huber C.G., et al., "On-Line Cation Exchange for Suppression of Adduct Formation in Negative-Ion Electrospray Mass Spectrometry of Nucleic Acids," Analytical Chemistry, 1998, vol. 70 (24), pp. 5288-5295.
Huletsky A., et al., "New Real-Time PCR Assay for Rapid Detection of Methicillin-Resistant*staphylococcus aureus* Directly from Specimens Containing a Mixture of Staphylococci," Journal of Clinical Microbiology, 2004, vol. 42 (5), pp. 1875-1884.
Hunag C., et al., "Detection of Arboviral RNA Directly from Mosquito Homogenates by Reverse Transcription-Polymerase Chain Reaction," Journal of Virological Methods, 2001, vol. 94 (1-2), pp. 121-128.
Hung E.C., et al., "Detection of SARS Coronavirus RNA in the Cerebrospinal Fluid of a Patient with Severe Acute Respiratory Syndrome," Clinical Chemistry, 2003, vol. 49 (12), pp. 2108- 2109.
Hurdle J.G., et al., "Analysis of Mupirocin Resistance and Fitness in *Staphylococcus aureus* by Molecular Genetic and Structural Modeling Techniques," Antimicrobial Agents and Chemotherapy, 2004, vol. 48 (11), pp. 4366-4376.
Hurst G.B., et al., "Detection of Bacterial DNA Polymerase Chain Reaction Products by Matrix-Assisted Laser Desorptionfionization Mass Spectrometry," Rapid Communications in Mass Spectrometry, 1996, vol. 10 (3), pp. 377-382.
Hurst G.B., et al., "MALDI-TOF Analysis of Polymerase Chain Reaction Products from Methanotrophic Bacteria," Analytical Chemistry, 1998, vol. 70 (13), pp. 2693-2698.
Hutchison C.A., et al., "Maternal Inheritance of Mammalian Mitochondrial DNA," Nature, 1974, vol. 251 (5475), pp. 536-538.
Hyde-Deruyscher R., et al., "Polyomavirus Early-Late Switch is not Regulated at the Level of Transcription Initiation and is associated with changes in RNA Processing," Proceedings of the National Academy of Sciences, 1988, vol. 85, pp. 8993-8997.
Ieven M., et al., "Rapid Detection of Methicillin Resistance in Coagulase-Negative Staphylococci by Commercially Available Fluorescence Test," Journal of Clinical Microbiology, 1995, vol. 33 (8), pp. 2183-2185.
Ihle O., et al., "Efficient Purification of DNA Fragments using a Protein Binding Membrane," Nucleic Acids Research, 2000, vol. 28 (16), pp. e76.
Inglis T.J., et al., "Rapid Genotypic Confirmation of Methicillin Resistance," Pathology, 1996, vol. 28 (3), pp. 259-261.
Ingman M., et al., "Mitochondrial Genome Variation and the Origin of Modern Humans," Nature, 2000, vol. 408 (6813), pp. 708-713.
International Preliminary Examination Report for Application No. PCT/US2002/06763, mailed on Jun. 11, 2003, 6 pages.
International Preliminary Examination Report for Application No. PCT/US2002/20336, mailed on Apr. 26, 2004, 8 pages.
International Preliminary Examination Report for Application No. PCT/US2003/09802, mailed on Apr. 8, 2005, 7 ppages.
International Preliminary Examination Report for Application No. PCT/US2003/22835, mailed on Mar. 5, 2005, 4 pages.
International Preliminary Examination Report for Application No. PCT/US2003/38505, mailed on Mar. 3, 2006, 5 pages.
International Preliminary Examination Report for Application No. PCT/US2003/38757, mailed on Feb. 2, 2007, 5 pages.
International Preliminary Examination Report for Application No. PCT/US2003/38761, mailed on Jun. 27, 2006, 6 pages.
International Preliminary Report on Patentability and Written Opinion for Application No. PCT/US2005/00386, mailed on Jul. 10, 2006, 6 pages.
International Preliminary Report on Patentability and Written Opinion for Application No. PCT/US2005/030058, mailed on Sep. 25, 2007, 6 pages.
International Preliminary Report on Patentability and Written Opinion for Application No. PCT/US2005/033707, mailed on Mar. 20, 2007, 6 pages.
International Preliminary Report on Patentability for Application No. PCT/US2004/033742, mailed on Jun. 20, 2006, 1 page.
International Preliminary Report on Patentability for Application No. PCT/US2006/028397, mailed on Jan. 22, 2008, 1 page.
International Preliminary Report on Patentability for Application No. PCT/US2008/054926, mailed on Aug. 26, 2009, 1 page.
International Preliminary Report on Patentability for Application No. PCT/US2009/057201, mailed on Mar. 22, 2011, 1 page.
International Preliminary Report on Patentability, Written Opinion and International Search Report for Application No. PCT/US2004/015123, mailed on Oct. 3, 2005, 8 pages.
International Search Report and Written Opinion for Application No. PCT/US2005/018031, mailed on Jun. 28, 2006, 14 pages.
International Search Report and Written Opinion for Application No. PCT/US2006/007747, mailed on Sep. 5, 2006, 13 pages.
International Search Report and Written Opinion for Application No. PCT/US2006/028397, mailed on Mar. 5, 2007, 14 pages.
International Search Report and Written Opinion for Application No. PCT/US2006/040747, mailed on Mar. 17, 2009, 19 pages.
International Search Report and Written Opinion for Application No. PCT/US2006/061307, mailed on Jan. 9, 2008, 21 pages.
International Search Report and Written Opinion for Application No. PCT/US2007/020045 mailed on Jan. 8, 2009, 17 pages.
International Search Report and Written Opinion for Application No. PCT/US2008/054926, mailed on Jan. 26, 2009, 15 pages.
International Search Report and Written Opinion for Application No. PCT/US2008/057901, mailed on Aug. 28, 2008, 14 pages.
International Search Report and Written Opinion for Application No. PCT/US2008/064891, mailed on Jun. 29, 2009, 15 pages.
International Search Report and Written Opinion for Application No. PCT/US2009/057201, mailed on Jul. 9, 2010, 13 pages.
International Search Report for Application No. PCT/US04/007236, mailed on Feb. 24, 2006, 2 pages.
International Search Report for Application No. PCT/US2002/06763, mailed on Oct. 23, 2002, 2 pages.
International Search Report for Application No. PCT/US2002/20336, mailed on Feb. 3, 2003, 4 pages.
International Search Report for Application No. PCT/US2003/009802, mailed on 3, 2004, 2 pages.
International Search Report for Application No. PCT/US2003/038505, mailed on Apr. 12, 2005, 2 pages.
International Search Report for Application No. PCT/US2003/038830, mailed on Aug. 25, 2004, 4 pages.

(56) References Cited

OTHER PUBLICATIONS

International Search Report for Application No. PCT/US2003/22835, mailed on Dec. 12, 2003, 1 page.
International Search Report for Application No. PCT/US2003/38757, mailed on Jun. 24, 2004, 2 pages.
International Search Report for Application No. PCT/US2003/38761, mailed on Dec. 30, 2005, 5 pages.
International Search Report for Application No. PCT/US2003/38795, mailed on Apr. 19, 2004, 3 pages.
International Search Report for Application No. PCT/US2004/012671, mailed on Sep. 28, 2007, 2 pages.
International Search Report for Application No. PCT/US2004/015196, mailed on Jul. 1, 2005, 3 pages.
International Search Report for Application No. PCT/US2004/028869, mailed on Jul. 17, 2006, 4 pages.
International Search Report for Application No. PCT/US2004/033742, mailed on May 15, 2006, 2 pages.
International Search Report for Application No. PCT/US2005/000386, mailed on May 9, 2006, 3 pages.
International Search Report for Application No. PCT/US2005/005356, mailed on Aug. 7, 2007, 4 pages.
International Search Report for Application No. PCT/US2005/006133, mailed on Jul. 26, 2007, 4 pages.
International Search Report for Application No. PCT/US2005/009557, mailed on Sep. 19, 2005, 1 page.
International Search Report for Application No. PCT/US2005/018337, mailed on Oct. 10, 2006, 2 pages.
International Search Report for Application No. PCT/US2005/024799, mailed on Dec. 28, 2006, 4 pages.
International Search Report for Application No. PCT/US2005/030058, mailed on Aug. 20, 2007, 1 page.
International Search Report for Application No. PCT/US2005/033707, mailed on 06 Feb.2006, 3 pp.
International Search Report for Application No. PCT/US2007/066194, mailed on Jan. 15, 2008, 4 pages.
International Search Report for Application No. PCT/US2008/057901, mailed on Jun. 29, 2009, 15 pages.
International Search Report for Application No. PCT/US2008/065332, mailed on Nov. 28, 2008, 4 pages.
International Search Report for Appliaction No. PCT/US2009/045635, mailed on Oct. 7, 2009, 9 pages.
Inyaku K., et al., "Rapid Detection and Identification of Mycobacteria in Sputum Samples by NestedPolymerase Chain Reaction and Restriction Fragment Length Polymorphisms of dnaJ Heat Shock Protein Gene," Journal of Medical Sciences, 1993, vol. 42 (1), pp. 21-31.
Iqbal S.S., et al., "A Review of Molecular Recognition Technologies for Detection of Biological Threat Agents," Biosensors & Bioelectronics, 2000, vol. 15 (11-12), pp. 549-578.
Isola N.R., et al., "MALDI-TOF Mass Spectrometric Method for Detection of Hybridized DNA Oligomers," Analytical Chemistry, 2001, vol. 73 (9), pp. 2126-2131.
Iteman I., et al., "Comparison of Conserved Structural and Regulatory Domains within Divergent 16S rRNA-23S rRNA Spacer Sequences of Cyanobacteria," Microbiology, 2000, vol. 146 (Pt 6), pp. 1275-1286.
Ito T., et al., "Insights on Antibiotic Resistance of *Staphylococcus aureus* from its Whole Genome: Genomic Island Scc," Drug Resistance Updates, 2003, vol. 6 (1), pp. 41-52.
Ito T., et al., "Structural Comparison of Three Types of Staphylococcal Cassette Chromosome mecIntegrated in the Chromosome in Methicillin-Resistant *Staphylococcus aureus*," Antimicrobial Agents and Chemotherapy, 2001, vol. 45 (5), pp. 1323-1336.
Jackson P.E., et al., "Mass Spectrometry for Genotyping: an Emerging Tool for Molecular Medicine," Molecular Medicine Today, 2000, vol. 6 (7), pp. 271-276.
James A.M., et al., "Borelia Lonestari Infection after a Bite by an Amblyomma Americanum Tick," The Journal of Infectious Diseases, 2001, vol. 183 (12), pp. 1810-1814.
Jankowski K., et al., "Mass Spectrometry of DNA. Part 2 Quantitative Estimation of Base Composition," European Journal of Mass Spectrometry, 1980, vol. 1 (1), pp. 45-52.
Jansen R.C., et al., "Genotype-by-environment Interaction in Genetic Mapping of Multiple Quantitative Trait Loci," Theoretical and Applied Genetics, 1995, vol. 91, pp. 33-37.
Jaulhac B., et al., "Specific Detection of the Toxic Shock Syndrome Toxin-1 Gene Using the Polymerase Chain Reaction," Molecular and Cellular Probes, 1991, vol. 5, pp. 281-284.
Jaulhac B., et al., "Synthetic DNA Probes for Detection of Genes for Enterotoxins A, B, C, D,.E and for TSST-1 in Staphylococcal Strains," Journal of Applied Bacterial, 1992, vol. 72 (5), pp. 386-392.
Jensen M.A., et al., "Rapid Identification of Bacteria on the Basis of Polymcrase Chain Reaction-Amplified Ribosomal DNA Spacer Polymorphisms," Applied and Environmental Microbiology, 1993, vol. 59 (4), pp. 945-952.
Jeong J., et al., "Early Screening of Oxacillin-*Staphylococcus aureus Staphylococcus epidermidis* from Blood Culture," Journal of Korean Medical Science, 2002, vol. 17, pp. 168-172.
Jiang C., et al., "Multiple Trait Analysis of Genetic Mapping for Quantitative Trait Loci Genetics," Genetics, 1995, vol. 140 (3), pp. 1111-1127.
Jiang Y., et al., "A Highly Efficient and Automated Method for Purifying and Desalting PCR Products for Analysis by Electrospray Ionization Mass Spectrometry," Analytical Biochemistry, 2003, vol. 316 (1), pp. 50-57.
Johansson A., et al., "Evaluation of Pcr-based Methods for Discrimination of Francisella species and Subspecies and Development of a Specific PCR that Distinguishes the Two Major Subspecies *Francisella tularensis*," Journal of Clinical Microbiology, 2000, vol. 38 (11), pp. 4180-4185.
Johnson W.M., et al., "Detection of Genes for Enterotoxins, Exfoliative Toxins, and Toxic Shock Syndrome Toxin 1 in *Staphylococcus aureus* by the Polymerase Chain Reaction," Journal of Clinical Microbiology, 1991, vol. 29 (3), pp. 426-430.
Johnson Y.A., et al., "Precise Molecular Weight Determination of PCR Products of the rRNA of *B. subtilis* and *B. atrophaeus*, Closely Related Species of *Bacilli*," Journal of Microbiological Methods, 2000, vol. 40 (3), pp. 241-254.
Jonas D., et al., "Rapid Pcr-Based Identification of Methicillin-Resistant *Staphylococcus aureus*from Screening Swabs," Journal of Clinical Microbiology, 2002, vol. 40 (5), pp. 1821-1823.
Jurinke C., et al., "Application of Nested PCR and Mass Specctrometry for DNA Based Virus Detection: HBV-DNA Detected in the Majority of Isolated Anti-Hbc Positive Sera," Genetic Analysis: Biomolecular Engineering, 1998, vol. 14 (3), pp. 97-102.
Jurinke C., et al., "Detection of Hepatitis B: Virus DNA in Serum Samples Via Nested PCR and MALDI-TOF Mass Spectrometry," Genetic Analysis: Biomolecular Engineering, 1996, vol. 13 (3), pp. 67-71.
Jurinke C., et al., "MALDI-TOF Mass Spectrometry. A Versatile Tool for High-Performance DNA Analysis," Molecular Biotechnology, 2004, vol. 26 (2), pp. 147-163.
Kacian D.L., et al., "A Replicating RNA Molecule Suitable for a Detailed Analysis of Extracellular Evolution and Replication," Proceeding of the National Academy of Sciences, 1972, vol. 69 (10), pp. 3038-3042.
Kageyama A., et al. "Rapid Detection of Human Fecal Eubacterium Species and Related Genera by Tested PCR Method," Journal of Microbiology, Immunology, 2001, vol. 45 (4), pp. 315-318.
Kajon A.E., et al., "Genome Type Analysis of Brazilian Adenovirus Strains of Serotypes 1, 2, 3, 5,and 7 Collected Between 1976 and 1995," Journal of Medical, 1999, vol. 58 (4), pp. 408-412.
Kasai H., et al., "Construction of the gyrB Database for the Identification and Classification of Bacteria," Genome Informatics. Workshop on Genome Informatics, 1998, pp. 13-21.
Katano H., et al., "Identification of Adeno-Associated Virus Contamination in Cell and Virus Stocks by PCR," Biotechniques, 2004, vol. 36 (4), pp. 676-680.
Katayama Y., et al., "Genetic Organization of the Chromosome Region Surrounding mecA inClinical Staphylococcal Strains: Role of IS431 -Mediated mecl Deletion in Expression of Resistance

(56) References Cited

OTHER PUBLICATIONS inmed-Canying, Low-Level Methicillin-Resistant *Staphylococcus haemolyticus*," Antimicrobial Agents and Chemotherapy, 2001, vol. 45 (7), pp. 1955-1963.
Ke D., et al., "Development of a PCR Assay for Rapid Detection of Enterococci," Journal of Clinical Microbiology, 1999, vol. 37 (11), pp. 3497-3503.
Kearns A.M., et al., "Rapid Detection of Methicillin-Resistant Staphylococci by Multiplex PCR," The Journal of Hospital Inspection, 1999, vol. 43 (1), pp. 33-37.
Keller A., et al., "Empirical Statistical Model to Estimate the Accuracy of Peptide Identifications Made by MS/MS and Database Search," Analytical Chemistry, 2002, vol. 74 (20), pp. 5383-5392.
Khan A.S., et al., "An Outbreak of Crimean-Congo Haemorrhagic Fever in the United Arab Emirates, 1994-1995," The American Journal of Tropical Medicine and Hygiene, 1997, vol. 57 (5), pp. 519-525.
Khan S.A., et al., "Simultaneous Detection of Erythromycin-Resistant Methylase Genes ermA and ermC from *Staphylococcus* Spp. By Multiplex-PCR," Molecular and Cellular Probes, 1999, vol. 13 (5), pp. 381-387.
Kidd A.H., et al., "Rapid Subgenus Identification of Human Isolates by A General PCR," Journal of Clinical Microbiology, 1996, vol. 34 (3), pp. 622-627.
Kidd-Ljunggren K., et al., "The Hepatitis B Virus X Gene: Analysis of Functional Domain Variation and Gene Phylogeny using Multiple Sequences," Journal of General Virology, 1995, vol. 76 (pt 9), pp. 2119-2130.
Kikuchi K., et al., "Restriction Fragment Length Polymorphism Analysis of Clinical Isolates of *Mycobacterium haemophilum*," Journal of Clinical Microbiology, 1994, vol. 32 (7), pp. 1763-1767.
Kilbourne E.D., "Influenza Pandemics: Can We Prepare for the Unpredictable," Immunology, 2004, vol. 17 (3), pp. 350-357.
Kilbourne E.D., "Influenza Pandemics of the 20th Century," Emerging Infectious Diseases Journal, 2006, vol. 12 (1), pp. 9-14.
Kilpatrick D.R., et al., "Group-Specific Identification of Polioviruses by PCR Using Primer Containing Mixed- Base or Deoxyinosine Residues at Positions of Coden Degeneracy," Journal of Clinical Microbiology, 1996, vol. 34 (12), pp. 2990-2996.
Kim B.J., et al., "Identification of Mycobacterial Species by Comparative Sequence Analysis of the RNA Polymerase Gene (rpoB)," Journal of Clinical Microbiology, 1999, vol. 37 (6), pp. 1714-1720.
Kinney R.M., et al., "Nucleotide Sequences of the 26S mRNAs of the Viruses Defining the Venezuelan Equine Encephalitis Antigenic Complex," The American Journal of Tropical Medicine and Hygiene, 1998, vol. 59 (6), pp. 952-964.
Kirpekar F., et al., "Matrix Assisted Laser Desorption/Ionization Mass Spectrometry of Enzymatically Synthesized RNA up to 150 kDa," Nucleic Acids Research, 1994, vol. 22 (19), pp. 3866-3870.
Kitagawa Y., et al., "Rapid Diagnosis of Methicillin-Resistant *Staphylococcus aureus* Bacteremia by Nested Polymerase Chain Reaction," Annals of Surgery, 1996, vol. 224 (5), pp. 665-671.
Knoth K., et al., "Highly Degenerate, Inosine-Containing Primers Specifically Amplify Rare cDNA using the Polymerase Chain Reaction," Nucleic Acids Research, 1988, vol. 16 (22), pp. 10932.
Kolbert C.P., et al., "Branched-DNA Assay for Detection of the mecA Gene in Oxacillin-Resistant and Oxacillin-Sensitive Staphylococci," Journal of Clinical Microbiology, 1998, vol. 36 (9), pp. 2640-2644.
Kowalak J.A., et al., "A Novel Method for the Determination of Post-Transcriptional Modification in RNA by Mass Spetrometry," Nucleic Acids Research, 1993, vol. 21 (19), pp. 4577-4585.
Krafft A.E., et al., "Evaluation of PCR Testing of Ethanol-Fixed Nasal Swab Specimens as an Augmented Surveillance Strategy for Influenza Virus and Adenovirus Identification," Journal of Clincal Microbiology, 2005, vol. 43 (4), pp. 1768-1775.
Krahmer M.T., et al., "Electrospray Quadrupole Mass Spectrometry Analysis of Model Oligonucleotides and Polymerase Chain Reaction Products: Determination of Base Substitutions, Nucleotide Additions/Deletions, and Chemical Modifications," Analytical Chemistry, 1999, vol. 71 (14), pp. 2893-2900.

Krahmer M.T., et al, "MS for Identification of Single Nucleotide Polymorphisms and MS/MS for Discrimination of Isomeric PCR Products," Analytical Chemistry, 2000, vol. 72 (17), pp. 4033-4040.
Kramer L.D., et al., "Dection of St. Louis Encephalitis Viruses in Mosquitoes (Diptera: Culicidea) and Avian Tissues," Journal of Medcal Entomology, 2002, vol. 39 (2), pp. 312-323.
Kramer L.D., et al., "Detection of St. Louis Encephalitis and Western Equine Encephalomyelitis RNA in Mosquitoes Tested Without Maintainance of a Cold Chain," Journal of the American Control Control Association, 2001, vol. 17 (4), pp. 213-215.
Kresken M., et al., "Prevalence of Mupirocin Resistance in Clinical Isolates of Isolates of *Staphylococcus aureus* and *Staphylococcus epidermidis*: Results of the Antimicrobial Resistance Surveillance Study of the Paul-Ehrlich-Society for Chemotherapy, 2001," International Journal of Antimicrobial Agents, 2004, vol. 23 (6), pp. 577-581.
Krishnan P.U., et al., "Detection of Methicillin and Mupirocin Resistance in *Staphylococcus aureus* isolates Using Conventional and Molecular Methods: A Descriptive Study from a Burns Unite with High prevalence of MRSA," Journal of Clinical Pathology, 2002, vol. 55 (10), pp. 745-748.
Kroes I., et al., "Bacterial Diversity Within the Human Subgingval Crevice," Proceeding of the National Academy of Sciences, 1999, vol. 96 (25), pp. 14547-14552.
Krossoy B., et al., "The Putative Polymerase Sequence of Infectious Salmon Anemia Virus Suggests a New Genus with the Orthomyxoviridae," Journal of Virology, 1999, vol. 73 (3), pp. 2136-2142.
Ksiazek T.G., et al., "A Novel Coronavirus Associated with Severe Acute Respiratory Syndrome," The New England Journal of Medicine, 2003, vol. 348 (20), pp. 1953-1966.
Kupke T., et al., "Molecular Characterization of Lantibiotic-Synthesizing Enzyme EpiD Reveals a Function for Bacterial Dfp Proteins in Coenzyme a Biosynthesis," Journal of Biological Chemistry, 2000, vol. 275 (41), pp. 31838-31846.
Kuroda M., et al., "Whole Genome Sequencing of Meticillin-Resistant *Staphylococcus*," The Lancet, 2001, vol. 357 (9264), pp. 1225-1240.
Kwok S., et al., "Avoiding False Positives with PCR," Nature, 1989, vol. 339 (6221), pp. 237-238.
Labandeira-Rey, M. et al., "*Staphylococcus aureus* Panton Valentine Leukocidin Causes Necrotizing Pneumonia," ScienceExpress, 2007, 8 pages.
Lacroix J.M., et al, "PCR-Based Technique for the Detection of Bacteria in Semen and Urine," Journal of Microbiological Methods, 1996, vol. 26, pp. 61-71.
Lacroix L., et al., "Triplex Formation by Oligonucleotides Containing 5-(1-Propynyl)-2- deoxyuridine: Decreased Magnesium Dependence and Improved Intracellular Gene Targeting," Biochemistry, 1999, vol. 38 (6), pp. 1893-1901.
Laken S.J., et al., "Genotyping by Mass Spectrometric Analysis of Short DNA Fragments," Nature Biotechnology, 1998, vol. 16 (13), pp. 1352-1356.
Lamb R.A., et al., "Sequence of Interrupted and Uninterrupted mRNAs and Cloned DNA Coding for the Two Overlapping Nonstructural Proteins of Influenza Virus," Cell, 1980, vol. 21 (2), pp. 475-485.
Lambert A.J., et al., "Detection of North American Eastern and Western Equine Encephalitis Viruses by Nucleic Acid Amplification Assays," Journal of Clinical Microbiology, 2003, vol. 41 (1), pp. 379-385.
Lau L.T., et al, "A Real-Time PCR for SARS-Coronavirus Incorporating Target Gene Pre-Amplification," Biochemical and Biophysical Research Communications, 2003, vol. 312 (4), pp. 1290-1296.
Lau L.T., et al., "Nucleic Acid Sequence-Based Amplification Methods to Detect Avian Influenza Virus," Biochemical and Biophysical Research Communications, 2004, vol. 313 (2), pp. 336-342.
Le Cann P., et al., "Quantification of Human Astroviruses in Sewage Using Real-Time RT-PCR," Research in Microbiology, 2004, vol. 155 (1), pp. 11-15.
Lebedev Y., et al., "Oligonucleotides Containing 2-Aminoadenine and 5-Methycytosine are More Effective as Primers for PCR Ampli-

(56) References Cited

OTHER PUBLICATIONS fication than their Nonmodified Counterparts," Genetic Analysis: Biomolecular Engineering, 1996, vol. 13 (1), pp. 15-21.

Lednicky J.A., et al., "Polyomaviruses and Human Tumors: A Brief Review of Current Concenpts and Interpretations," Frontiers Bioscience, 1999, vol. 4, pp. D153-D164.

Lee J.A., et al., "Rapid Identification of Human Adenovirus Types 3 and 7 from Respiratory Specimens via Multiplex Type-Specific PCR," Journal of Clinical Microbiology, 2005, vol. 43 (11), pp. 5509-5514.

Lee J.H., et al., "Simultaneous Detection of Three Mosquito-Borne Encephalitis Viruses (Eastern equine, La Crosse, and St. Louis) with a Single-Tube Multiplex Reverse Transcriptase Polymerase Chaine Reaction Assay," Journal of the American Mosquito Control Association, 2002, vol. 18 (1), pp. 26-31.

Leif H., et al., "Isolation and Characterization of the Proton-Translocating NADH: Ubiqu None Oxidoreductase from *Escherichia coli*," European Journal of Biochemistry, 1995, vol. 230 (2), pp. 538-548.

Lengyel A., et al., "Characterization of the Main Protein Components of Adenovirus Virion and its Possible Use in Laboratory Diagnostics," Acta Microbiologica Immunologica Hungarica, 1998, vol. 43 (3-4), pp. 281-283.

Leroy E.M., et al., "Diagnosis of Ebola Haemorrhagic Fever by RT-PCR in an Epidemic Setting," Journal of Medicinal Virology, 2000, vol. 60 (4), pp. 463-467.

Levi K., et al., "Evaluation of an Isothermal Signal Amplification Method for Rapid Detection of Methicillin-Resistant *Staphylococcus aureus* from Patient-Screening Swabs," Journal of Clinical Microbiology, 2003, vol. 41 (7), pp. 3187-3191.

Levine S.M., et al., "PCR-Based Detection of *Bacillus anthracis* in Formalin-Fixed Tissue from a Patient Receiving Ciprofloxacin," Journal of Clinical Microbiology, 2002, vol. 40 (11), pp. 4360-4362.

Levison P.R., et al., "Recent Developments of Magnetic Beads for Use in Nucleic Acid Purification," Journal of Chromatography, 1998, A816, 107-111.

Lewers K.S., et al., "Detection of Linked QTL for Soybean Brown Stem Rot Resistance in "BSR 101" as Expressed in a Growth Chamber Environment," Molecular Breeding, 1999, vol. 5, pp. 33-42.

Li C., et al., "Evolution of H9N2 Influenza Viruses from Domestic Poultry in Mainland China," Virology, 2005, vol. 340 (1), pp. 70-83.

Li J., et al., "Single Nucleotide Polymorphism Determination Using Primer Extension and Time-of-Flight Mass Spectrometry," Electrophoresis, 1999, vol. 20 (6), pp. 1258-1265.

Li Q., et al., "Screening of the High Yield Influenza B Virus on MDCK c14d Cloning of its Whole Genome," International Congress Series, 2004, vol. 1263, pp. 610-614.

Li Q., et al., "Genetic Variability of Hexon Loops 1 and 2 between Seven Genome Types of Adenovirus Serotype 7," Archives of Virology, 1999, vol. 144 (9), pp. 1739-1749.

Li Q.G., et al., "Analysis of 15 Different Genome Types of Adenovirus Type 7 Isolated on Five Continents," Journal of Virology, 1986, vol. 60 (1), pp. 331-335.

Li Q.G., et al., "Comparison of 17 Genome Types of Adenovirus Type 3 Identified among Strains Recovered from Six Continents," Journal of Clinical Microbiology, 1988, vol. 26 (5), pp. 1009-1015.

Liebermann H., et al., "Mapping of Linear Epitopes on Fibre Knob of Human Adenovirus Serotypes 8 and 15," Intervirology, 2002, vol. 45 (1), pp. 59-66.

Liebermann H., et al., "Mapping of Linear Epitopes on Fibre Knob of Human Adenovirus Serotype 5," Virus Research, 2001, vol. 73 (2), pp. 145-151.

Lim L.P., et al., "The MicroRNAs of *Caenorhabditis elegans*," Genes and Development, 2003, vol. 17 (8), pp. 991-1008.

Limbach P.A., et al., "Enzymatic Sequncing of Oligonucleotides with Electrospray Mass Spectrometry," 42nd ASMS Conference on Mass Spectrometry, 1994.

Limoncu M.H., et al., "Emergence of Phenotypic Resistance to Ciprofloxacin and Levofloxacin In methicillin-Resistant and Methicillin-Sensitive *Staphylococcus aureus* Strains," International Journal of Antimicrobial Agents, 2003, vol. 21 (5), pp. 420-424.

Lin B., et al., "Use of Oligonucleotide Microarrays for Rapid Detection and Serotyping of Acute Respiratory Disease-Associated Adenoviruses," Journal of Clinical Micrbiology, 2004, vol. 42 (7), pp. 3232-3239.

Lin P.H., et al., "Oxidative Damage to Mitochondrial DNA in Atrial Muscle of Patients with Atrial Fibrillation," Free Radical Biology and Medicine, 2003, vol. 35 (10), pp. 1310-1318.

Lina G., et al., "Bacterial Competition for Human Nasal Cavity Colonization: Role of Staphylococcal agr Alleles," Applied and Environmental Microbiology, 2003, vol. 69 (1), pp. 18-23.

Lina G., et al., "Involvement of Panton-Valentine Leukocidin-*Staphylococcus aureus* in Primary Skin Infections and Pneumonia," Clinical Infectious Diseases, 1999, vol. 29 (5), pp. 1128-1132.

Linssen B., et al., "Development of Reverse Transcription-PCR Assays Specific for Detection of Equine Encephalitis Viruses," Journal of Clinical Microbiology, 2000, vol. 38 (4), pp. 1527-1535.

Little D.P., et al., "MALDI on a Chip: Analysis of Arrays of Low-Femtomole to Subfemtomole Quantities of Synthetic Oligonucleotides and DNA Diagnostic Products Dispensed by a Piezoelctric Pipet," Analytical Chemistry, 1997, vol. 69, pp. 4540-4546.

Little D.P., et al, "Rapid Sequencing of Oligonucleotides by High-Resolution Mass Spectrometry," Journal of the American Chemical Society, 1994, vol. 116 (11), pp. 4893-4897.

Liu C., et al., "Improving the Microdialysis Procedure for Electrospray Ionization Mass Spectrometry of Biological Samples," Journal of Mass Spectrometry, 1997, vol. 32 (4), pp. 425-431.

Liu J.H., et al., "Interregional Transmission of the Internal Protein Genes of H2 Influenza Virus in Migratory Ducks from North America to Eurasia," Virus Genes, 2004, vol. 29 (1), pp. 81-86.

Liu Y., et al., "An Unusual Gene Arrangement for the Putative Chromosome Replication Origin and Circadian expression of dnaN in *Synechococcus* sp. Strain PCC 7942," Gene, 1996, vol.172 (1), pp. 105-109.

Livermore D.M., "The Threat from the Pink Corner," Annals of Medicine, 2003, vol. 35 (4), pp. 226-234.

Loakes D., et al., "Nitroindoles as Universal Bases," Nucleosides and Nucleotides, 1995, vol. 14 (3-5), pp. 1001-1003.

Loo J.A., et al., "Applying Charge Discrimination with Electrospray Ionization-Mass Spectrometry to Protein Analysis," Journal of American Society for Mass Spectrometry, 1995, vol. 6, pp. 1098-1104.

Lott T.J., et al., "Nucleotide Sequence Analysis of the 5-8s rDNA and Adjacent ITS2 Region of *Candida albicans* and Related Species," Yeast, 1993, vol. 9, pp. 1199-1206.

Louie L., et al., "Evaluation of Three Rapid Methods for Detection of Methicillin Resistance in *Staphylococcus* " Journal of Clinical Microbiology, 2000, vol. 38 (6), pp. 2170-2173.

Love B.C., et al., "Cloning and Sequence of the GroESL Heat-Shock Operon of Pasteurella Multocida," Gene, 1995, vol. 166 (1), pp. 179-180.

Lovseth A., et al., "Modified Multiplex Pcr Method for Detection of Pyrogenic Exotoxin Genes in Staphylococcal Isolates," Journal of Clinical Microbiology, 2004, vol. 42 (8), pp. 3869-3872.

Lowe T., et al., "A Computer Program for Selection of Oligonucleotide Primers for Polymerase Chain Reactions," Nucleic Acids Research, 1990, 18 (7), 1757-1761.

Lu X., et al., "Molecular Typing of Human Adenoviruses by PCR and Sequencing of a Partial Region of the Hexon Gene," Archives of Virology, 2006, vol. 151 (8), pp. 1587-1602.

Lubman D.M., Application for Continuation Grant by David Mitchell Lubman dated Jun. 4, 1996 and Jun. 14, 1996.

Lubman D.M., Application for Continuation Grant by David Mitchell Lubman dated Jun. 10, 1994 and Jun. 24, 1994.

Lubman D.M., Application for Grant by David Mitchell Lubman dated Sep. 1, 1994 and Sep. 27, 1994.

Lubman D.M., Application for Grant by David Mitchell Lubman dated Oct. 25, 1992 and Oct. 29, 1992.

Ludwig S.L., et al., "Prevalence of Antibodies to Adenovirus Serotypes 4 and 7 among Unimmunized US Army Trainees: Results

(56) References Cited

OTHER PUBLICATIONS of a Retrospective Nationwide Seroprevalence Survey," the Journal of Infectious Diseases, 1998, vol. 178 (6), pp. 1776-1778.
Ludwig W., et al., "Bacterial Phylogeny Based on 16S and 23S rRNA Sequence Analysis," FEMS Microbiolofy Reviews, 1994, vol. 15 (2-3), pp. 155-173.
Lukashov V.V., et al., "Evolutionary Relationships among Parvoviruses: Virus-Host Coevolution among Autonomous Primate Parvoviruses and Links between Adeno-Associated and Avian Parvoviruses," Journal of Virology, 2001, vol. 75 (6), pp. 2729-2740.
Ma X.X., et al., "Novel Type of Staphylococcal Cassette Chromosome Mec Identified in Community-Acquired Methicillin-*Staphylococcus* Strains," Antimicrobial Agents and Chemotherapy, 2002, vol. 46 (4), pp. 1147-1152.
Mack D.H., et al., "A Sensitive Method for the Identification of Uncharacterized Viruses Related to known Virus Groups: Hepadnavirus Model System," Proceedings of the National Academy of Sciences, 1988, vol. 85 (18), pp. 6977-6981.
Magnuson V.L., et al., "Substrate Nucleotide-Determined Non-Templated Addition of Adenine by Taq DNA Polymerase: Implications for PCR-Based Genotyping and Cloning," BioTechniques, 1996, vol. 21 (4), pp. 700-709.
Maiwald M., et al., "Characterization of Contaminating DNA in Taq Polymerase which Occurs During Amplification with a Primer Set for Legionella 5S Ribosomal RNA," Molecular and Cellular Probes, 1994, vol. 8 (1), pp. 11-14.
Malasig M.D., et al., "Simplified Microneutralization Test for Serotyping Adenovirus Isolates," Journal of Clinical Microbiology, 2001, vol. 39 (8), pp. 2984-2986.
Mangrum J.D., et al., "Solution Composition and Thermal Denaturation for the Production of Single-Stranded PCR Amplicons: Piperodine-Induced Destabilization of the DNA Duplex," Journal of the American Society for Mass Spectrometry, 2002, vol. 13 (3), pp. 232-240.
Manian F.A., "Asymptomatic Nasal Carriage of Mupirocin-Resistant, Methicillin-Resistant *Staphylococcus aureus* (MRSA) in a Pet Dog Associated with MRSA Infection in Household Contacts," Clinical Infectious Diseases, 2003, vol. 36 (2), pp. e26-e28.
Marks F., et al., "Genotyping of Plasmodium Falciparum Pyrimethamine Resistance by Matrix-Assisted Laser Desportion-Ionization Time-of-Flight Mass Spectrometry," Antimicrobial Agents and Chemotherapy, 2004, vol. 48 (2), pp. 466-472.
Marmur J., et al., "Strand Separation and Specific Recombination in Deoxyribonucleic Acids: Biological Studies," Proceedings of the National Academy of Sciences, 1960, vol. 46(4), pp. 453-461.
Martemyanov K.A., et al., "Extremely Thermostable Elongation Factor (3 from Aquifer aeolicus: Cloning, Expression, Purification, and Characterization in a Heterologous Translation System," Protein Expression and Purification, 2000, vol. 18 (3), pp. 257-261.
Martineau F., et al., "Development of PCR Assay for Identifucation of Staphylococci at Genus and Species Levels," Journal of Clinical Microbiology, 2001, vol. 39 (7), pp. 2541-2547.
Martineau F., et al., "Species-Specific and Ubiquitous-DNA-Based Assays for Rapid Identification of *Staphylococcus aureus*," Journal of Clinical Microbiology, 1998, vol. 36 (3), pp. 618-623.
Martin-Lopez J.V., et al., "Simultaneous PCR Detection of ICA Cluster and Methicillin and Mupirocinresistance Genes in Catheter-Isolated *Staphylococcus*," International Microbiology, 2004, vol. 7 (1), pp. 63-66.
Mason V.P., et al., "Diversity and linkage of Replication and Mobilisation Genes in *Bacillus* Rolling Irclereplicating Plasmids from Diverse Geographical Origins," FEMS Microbiology Ecology, 2002, vol. 42 (2), pp. 235-241.
Matray T.J., et al., "Synthesis and Properties of RNA Analogs-Oligoribonucleotide N3—>p5 Phosphoramidates," Nucleic Acids Research, 1999, vol. 27 (20), pp. 3976-3985.
Matsuoka M., et al., "Characteristic Expression of Three Genes, msr(a), mph(C) and erm(Y), Thatconfer Resistance to Macrolide Antibiotics on Staphylococcus Aureus," FEMS Microbiology Letters, 2003, vol. 220 (2), pp. 287-293.

May A.C., "Percent Sequence Identity: The Need to be Explicit," Structure, 2004, vol. 12 (5), pp. 737-738.
McCabe K.M., et al., "Bacterial Species Identification After DNA Amplification with a Universal Primer Pair," Molecular Genetics and Metabolism, 1999, vol. 66 (3), pp. 205-211.
McLafferty F.W., et al., "Comparison of Algorithms and Databases for Matching Unknown Mass Spectra," Journal of the American Society for Mass Spectrometry, 1998, vol. 9 (1), pp. 92-95.
Mcluckey S.A., et al., "Ion Trap Tandem Mass Spectrometry Applied to Small Multiply Charged Oligonucleotides with a Modified Base," Journal of the American Society for Mass Spectrometry, 1994, vol. 5, pp. 740-747.
Mehrotra M., et al., "Multiplex PCR for Detection of Genes for *Staphylococcus aureus* Enterotoxins, Exfoliative Toxins, Toxic Shock Syndrome Toxin 1, and Methicillin Resistance," Journal of Clinical Microbiology, 2000, vol. 38 (3), pp. 1032-1035.
Meiyu F., et al., "Detection of Flaviviruses by Reverse Transcriptase-Polymerase Chain Reaction with the Universal Primer Set," Microbiology and Immunology, 1997, vol. 41 (3), pp. 209-213.
Mellor J., et al., "Genotype Dependence of Hepatitis C Virus Load Measurement in Commercially Available Quantitative Assays," Journal of Clinical Microbiology, 1999, vol. 37 (8), pp. 2525-2532.
Merlino J., et al., "New Chromogenic Identification and Detection *Staphylococcus aureus* and Methicillin-Resistanct *S. aureus*," Journal of Clinical Microbiology, 2000, vol. 38 (6), pp. 2378-2380.
Merlino J., et al., "Rapid Detection of Non-Multidrug-Resistant and Multidrug-Resistant Methicillin-Resistant *Staphylococcus aureus* Using Cycling Probe Technology for the mecA Gene," European Journal of Clinical Microbiology and Infectious Diseases, 2003, vol. 22 (5), pp. 322-323.
Messmer T.O., et al., "Discrimination *Streptococcus pneumoniae* from Other Upper respiratory tract Streptococci by Arbitrary Primed PCR," Clinical Biochemistry, 1995, vol. 28 (6), pp. 567-572.
Metzgar D., et al., "PCR Analysis of Egyptian Respiratory Adenovirus Isolates, Including Identification of Species, Serotypes and Coinfections," Journal of Clinical Microbiology, 2005, vol. 43 (11), pp. 5743-5752.
Miller K.W., et al., "A Compendium of Human Mitochondria! DNA Control Region: Development of an International Standard Forensic Database," Croatian Medical Journal, 2001, vol. 42 (3), pp. 315-327.
Miragaia M., et al., "Genetic Diversity among Methicillin-Resistant *Staphylococcus epidermidis*(MRSE)," Microbial Drug Resistance, 2005, vol. 11 (2), pp. 83-93.
Miura-Ochiai R., et al., "Quantitative Detection and Rapid Identification of Human Adenoviruses," Journal of Clinical Microbiology, 2007, vol. 45 (3), pp. 958-967.
Mollet C., et al., "RpoB Sequence Analysis as a Novel Basis for Bacterial Identification," Molecular Microbiology, 1997, vol. 26 (5), pp. 1005-1011.
Monroy a.M., et al., "Exvaluation of Reverse Transcriptase Polymerase Chain Reaction for the Detection of Easter Equine Encephalumyelitis Virus during Vector Surveillance," Journal of Medical Entomology, 1996, vol. 33 (3), pp. 449-457.
Moore C., et al., "Development and Evaluation of a Real-Time Nucleic Acid Sequence Based Amplification Assay for Rapid Detection of Influenza A," Journal of Medical Virology, 2004, vol. 74 (4), pp. 619-628.
Moricca S., et al., "Detection of *Fusarium oxysporum* f.sp. Vasinfectum in Cotton Tissue by Polymerase Chain Reaction," Plant Pathology, 1998, vol. 47 (4), pp. 486-494.
Morinaga N., et al., "Purification, Cloning and Charactarizarion of Variant LukE-LukD with Strong Leukocidal Activity of Staphylococcal Bi-Component Leukotoxin Family," Microbioly and Immunology, 2003, vol. 47 (1), pp. 81-90.
Morse R., et al., "Nucleotide Sequence of Part of the ropC Gene Encoding the B Subunit of DNA Dependent RNA Polymerase from some Gram-Positive Bacteria and Comparative Amino Acid Sequence Analysis," Systematic and Applied Microbiology, 1996, vol. 19, pp. 150-157.
Muddiman D.C., et al., "Application of Secondary Ion and Matrix-Assisted Laser Desorption-Ionization Time-of-Flight Mass Spectrometry for the Quantitative Analysis of Biological Milecules," Mass Spetrometry Reviews, 1995, vol. 14 (6), pp. 383-429.

(56) References Cited

OTHER PUBLICATIONS

Muddiman D.C., et al., "Characterization of PCR Products from Bacilli Using Electrospray Ionization FTICR Mass Spectrometry," Analytical Chemistry, 1996, vol. 68 (21), pp. 3705-3712.

Muddiman D.C., et al., "Sequencing and Characterization of Larger Oligonucleotides by Electrospray Ionization Fourier Transform Ion Cyclotron Resoncance Mass Spetrometry," Reviews in Analytical Chemistry, 1998, vol. 17 (1), pp. 1-68.

Muddiman D.C., et al., "Important Aspects Concerning the Quantification of Biomolecules by Time-of-Flight Secondaryion Mass Spectrometry," Applied Spetrometry, 1996, vol. 50 (2), pp. 161-166.

Muddiman D.C., et al., "Length and Base Composition of Pcr-Amplified Nucleic Acids Using Mass Measurements from Electrospray Ionization Mass Spectrometry," Analytical Chemistry, 1997, vol. 69 (8), pp. 1543-1549.

Muddiman D.C., et al., "Precise Mass Measurement of a Double-Stranded 500 Base-Pair (309 kDA) Polymerase Chain Reaction Product by Negative Ion Electrospray Ionization Fourier Transform Ion Cyclotron Resonance Mass Spectrometry," Rapid Communications in Mass Spectrometry, 1999, vol. 13 (2), pp. 1201-1204.

Muhammed W.T., et al., "Electrospray Ionization Quadrupole Time-of-Flight Mass Spectrometry and Guadrupole Mass Spectrometry for Genotyping Single Nucleotide Substitutions in Intact Polymerase Chain Products in K-Ras and p53," Rapid Communications in Mass Spectrometry, 2002, vol. 16 (24), pp. 2278-2285.

Murakami K., et al., "Identification of Methicillin-Resistant Strains of Staphylococci by Polymerase Chain Reaction," Journal of Clinical Microbiology, 1991, vol. 29 (10), pp. 2240-2244.

Mushegian A.R., et al., "A Minimal Gene Set for Cellular Life Derived by Comparison of Complete Bacterial Genomes," Proceedings of the National Academy of Science, 1996, vol. 93 (19), pp. 10268-10273.

Na B.K., et al., "Detection and Typing of Respiratory Adenoviruses in a Single-Tube Multiplex Polymerase Chain Reaction," Journal of Medical Virology, 2002, vol. 66 (44), pp. 512-517.

Nagpal M.L., et al., "Utility of 16S-23S rRNA Spacer Region Methodology: How Similar are Interspace Regions within a Genome and Between Strains for Closely Related Organisms", Journal of Microbiological Methods, 1998, vol. 33, pp. 211-219.

Nagy M., et al., "Sequence Analysis of Porcine Adenovirus Serotype 5 Fibre Gene: Evidence for Recombination," Virus Genes, 2002, vol. 24 (2), pp. 181-185.

Naito Y., et al., "Molecular Mass Measurement of Polymerase Chain Reaction Products Amplified from Human Blood DNA by Electrospray Ionization Mass Spectrometry," Rapid Communications in Mass Spectrometry, 1995, vol. 9 (15), pp. 1484-1486.

Nakagawa S., et al., "Gene Sequences and Specific Detection for Panton-Valentine Leukocidin," Biochemical and Biophysical Research Communications, 2005, vol. 328 (4), pp. 995-1002.

Nakao H., et al., "Development of a Direct PCR Assay for Detection of the Diphtheria Toxin Gene," Journal of Clinical Microbiology, 1997, vol. 35 (7), pp. 1651-1655.

Narita S., et al., "Phage Conversion of Panton-Valentine Leukocidin in *Staphylococcus aureus*: Molecular Analysis of a PVL-Converting Phage, cpSLT," Gene, 2001, vol. 268 (1-2), pp. 195-206.

Naumov G.I., et al., "Discrimination Between the Soil Yeast Species Williopsis Saturnus and Williopsis Suaveolens by the Polymerase Chain Reaction with the Universal Primer N21," Microbiology, 2000, vol. 69 (2), pp. 229-233.

NEB Catalog, 1998/1999, pp. 1, 79, 121 and 284.

Neumann G., et al., "Host Range Restriction and Pathogenicity in the Context of Influenza Pandemic," Emerging Infectious Diseases, 2006, vol. 12 (6), pp. 881-886.

Newcombe J., et al., "PCR of Peripheral Blood for Diagnosis of Meningococcal Disease," Journal of Clinical Microbiology, 1996, vol. 34 (7), pp. 1637-1640.

Ng E.K., et al., "Serial Analysis of the Plasma Concentration of SARS Coronavirus RNA in Pediatric Patients with Severe Acute Respiratory Syndrome," Clinical Chemistry, 2003, vol. 49 (12), pp. 2085-2088.

Ng E.K., et al., "Quantitative Analysis an Prognostic Implication of SARS Coronavirus RNA in the Plasma and Serum of Patients with Severe Acute Respiratory Syndrome," Clinical Chemistry, 2003, vol. 49 (12), pp. 1976-1980.

Ni J., et al., "Interpretation of Oligonucleotide Mass Spectra for Determinationof Sequence Using Electrospray Ionization and Tandem Mass Spectrometry," Analytical Chemistry, 1996, vol. 68 (13), pp. 1989-1999.

Nilsson M., et al., "Evaluation of Mitochondrial DNA Coding Region Assays for Increased Discrimination in Forensic Analysis," Forensic Science International: Genetics, 2008, vol. 2 (1), Pp. 1-8.

Nishikawa T., et al., "Reconstitution of Active Recombinant Ship Toxin (Stc)1 from Recombinant Stx1 -A and Sbtl -B Subunits Independently Produced by *E. coli Clones*," FEMS Microbiol Letters, 1999, vol. 178 (1), pp. 13-18.

Non-Final Office Action mailed Feb. 2, 2007 for U.S. Appl. No. 10/844,938, filed May 12, 2004.

Non-Final Office Action mailed Oct. 2, 2009 for U.S. Appl. No. 11/929,707, filed 30, 2007.

Non-Final Office Action mailed Aug. 4, 2010 for U.S. Appl. No. 12/049,949, filed Mar. 17, 2008.

Non-Final Office Action mailed Apr. 6, 2009 for U.S. Appl. No. 11/331,987, filed Jan. 13, 2006.

Non-Final Office Action mailed Apr. 7, 2006 for U.S. Appl. No. 10/964,571, filed Oct. 12, 2004.

Non-Final Office Action mailed Aug. 7, 2007 for U.S. Appl. No. 10/844,938, filed May 12, 2004.

Non-Final Office Action mailed Jun. 10, 2009 for U.S. Appl. No. 10/844,938, filed May 12, 2004.

Non-Final Office Action mailed Jan. 12, 2010 for U.S. Appl. No. 11/491,376, filed Jul. 21, 2006.

Non-Final Office Action mailed Dec. 13, 2011 for U.S. Appl. No. 13/221,608, filed Aug. 30, 2011.

Non-Final Office Action mailed Dec. 13, 2012 for U.S. Appl. No. 13/595,189, filed Aug. 27, 2012.

Non-Final Office Action mailed Oct. 13, 2010 for U.S. Appl. No. 10/754,415, filed Jan. 9, 2004.

Non-Final Office Action mailed Sep. 16, 2009 for U.S. Appl. No. 11/233,630, filed Sep. 21, 2005.

Non-Final Office Action mailed Apr. 17, 2009 for U.S. Appl. No. 12/211,641, filed Sep. 16, 2008.

Non-Final Office Action mailed Nov. 19, 2003 for U.S. Appl. No. 09/798,007, filed Mar. 2, 2001.

Non-Final Office Action mailed Aug. 20, 2007 for U.S. Appl. No. 11/582,863, filed Oct. 17, 2006.

Non-Final Office Action mailed May 20, 2008 for U.S. Appl. No. 10/844,938, filed May 12, 2004.

Non-Final Office Action mailed Oct. 20, 2004 for U.S. Appl. No. 09/891,793, filed Jun. 26, 2001.

Non-Final Office Action mailed Feb. 23, 2009 for U.S. Appl. No. 10/660,122, filed Sep. 11, 2003.

Non-Final Office Action mailed May 26, 2010 for U.S. Appl. No. 11/869,449, filed Oct. 9, 2007.

Non-Final Office Action mailed Jul. 27, 2006 for U.S. Appl. No. 11/209,439, filed Aug. 8, 2005.

Non-Final Office Action mailed Jun. 28, 2010 for U.S. Appl. No. 11/930,002, filed Oct. 30, 2007.

Non-Final Office Action mailed Sep. 28, 2009 for U.S. Appl. No. 11/930,017, filed Oct. 30, 2007.

Non-Final Office Action mailed Dec. 29, 2010 for U.S. Appl. No. 12/616,422, filed Nov. 11, 2009.

Non-Final Office Action mailed Apr. 30, 2010 for U.S. Appl. No. 11/930,108, filed Oct. 31, 2007.

Norder H., et al., "Typing of Hepatitis B Virus Genomes by a Simplified Polymerase Chain Reaction," Journal of Medical Virology, 1990, vol. 31 (3), pp. 215-221.

Nordhoff E., et al., "Matrix Assisted Laser Desorption/Ionization Mass Spectrometry of Nucleic Acids with Wavelengths in the Ultraviolet and Infrared," Rapid Communications in Mass Spectrometry, 1992, vol. 6 (12), pp. 771-776.

Notice of Allowance mailed Apr. 1, 2011 for U.S. Appl. No. 11/233,630, filed Sep. 21, 2005.

(56) References Cited

OTHER PUBLICATIONS

Notice of Allowance mailed Jun. 3, 2009 for U.S. Appl. No. 11/331,978, filed Jan. 13, 2006.
Notice of Allowance mailed Aug. 5, 2010 for U.S. Appl. No. 11/233,630, filed Sep. 21, 2005.
Notice of Allowance mailed Jul. 5, 2013 for U.S. Appl. No. 13/595,189, filed Aug. 27, 2012.
Notice of Allowance mailed Aug. 6, 2009 for U.S. Appl. No. 10/728,486, filed Dec. 5, 2003.
Notice of Allowance mailed Dec. 10, 2010 for U.S. Appl. No. 11/233,630, filed Sep. 21, 2005.
Notice of Allowance mailed Dec. 10, 2010 for U.S. Appl. No. 11/491,376, filed 21, 2006.
Notice of Allowance mailed Jul. 10, 2012 for U.S. Appl. No. 13/221,608, filed Aug. 30, 2011.
Notice of Allowance mailed Nov. 12, 2009 for U.S. Appl. No. 10/728,486, filed Dec. 5, 2003.
Notice of Allowance mailed Dec. 15, 2008 for U.S. Appl. No. 11/331,978, filed Jan. 13, 2006.
Notice of Allowance mailed Jul. 17, 2013 for U.S. Appl. No. 13/595,189, filed Aug. 27, 2012.
Notice of Allowance mailed Sep. 18, 2009 for U.S. Appl. No. 10/660,998, filed Sep. 12, 2003.
Notice of Allowance mailed Nov. 24, 2009 for U.S. Appl. No. 11/331,978, filed 13, 2006.
Notice of Allowance mailed Oct. 24, 2013 for U.S. Appl. No. 13/595,189, filed Aug. 27, 2012.
Notice of Allowance mailed May 26, 2011 for U.S. Appl. No. 12/561,175, filed Sep. 16, 2009.
Notice of Allowance mailed Apr. 29, 2011 for U.S. Appl. No. 12/561,175, filed Sep. 16, 2009.
Notice of Allowance mailed Oct. 29, 2009 for U.S. Appl. No. 10/660,122, filed Sep. 11, 2003.
Notice of Allowance mailed May 31, 2012 for U.S. Appl. No. 13/221,608, filed Aug. 30, 2011.
Nubel U., et al., "PCR Primers to Amplify 16S rRNA Genes from Cyanobacteria," Applied and Environmental Microbiology, 1997, vol. 63 (8), pp. 3327-3332.
Null Allison P., et al., "Enzymatic Strategies for the Characterization of Nucleic Acids by Electrospray Ionization Mass Spectrometry," Rapid Communications in Mass Spectrometry, 2003, vol. 17 (24), pp. 2699-2706.
Null A.P., et al., "Determination of a Correction to Improve Mass Measurement Accuracy of Isotopically Unresolved Polymerase Chain Reaction Amplicons by Electrospray Ionization Fourier Transform Ion Cyclotron Resonance Mass Spectrometry," Rapid Communications in Mass Spectrometry, 2003, vol. 17 (15), pp. 1714-1722.
Null A.P., et al., "Evaluation of Sample Preparation Techniques for Mass Measurements of PCR Products Using ESFIT—ICR Mass Spectrometry," The American Society for Mass Spectrometry, 2002, vol. 13 (4), pp. 338-344.
Null A.P., et al., "Genotyping of Simple and Compound Short Tandem Repeat Loci Using Electrospray Ionization Fourier Transform Ion Cyclotron Resonance Mass Spectrometry," Analytical Chemistry, 2001, vol. 73 (18), pp. 4514-4521.
Null A.P., et al., "Implications of Hydrophobicity and Free Energy of Solvation for Characterization of Nucleic Acids by Electrospray Ionization Mass Spectrometry," Analytical Chemistry, 2003, vol. 75 (6), pp. 1331-1339.
Null A.P., et al., "Perspectives on the Use of Electrospray Ionization Fourier Transform Ion Cyclotron Resonance Mass Spectrometry for Short Tandem Repeat Genotyping in the Post Genome Era," Journal of Mass Spectrometry, 2001, vol. 36 (6), pp. 589-606.
Null A.P., et al., "Preparation of Single-Stranded PCR Products for Electrospray Ionization Mass Spectrometry Using the DNA Repair Enzyme Lambda Exonuclease," Analyst, 2000, vol. 125 (4), pp. 619-626.

Nunes E.L., et al., "Detection of IIeS-2 Gene Encoding Mupirocin Resistance in Methicillin-Resistant *Staphylococcus aureus* by Multiplex PCR," Diagnostic Microbiology and Infectious Disease, 1999, vol. 34 (2), pp. 77-81.
Nygren M., et al., "Quantification of HIV-1 Using Multiple Quantitative Polymerase Chain Reaction Standards and Bioluminometric Detection," Analytical Biochemistry, 2001, vol. 288 (1), pp. 28-38.
Oberacher H., et al., "Analysis of Polymerase Chain Reaction Products by On-Line Liquid Chromatography Mass Spectrometry for Genotyping of Polymeric Short tandem Repeat Loci," Analytical Chemistry, 2001, vol. 73 (21), pp. 5109-5115.
Oberacher H., et al., "Increased Foresnic Efficiency of DNA Fingerprints Through Simultaneous Resolution of Length and Nucleotide Variability by High-Performance Mass Spectrometry," Human Mutation, 2008, vol. 29 (3), pp. 427-432.
Oberste M.S., et al., "Improved Molecular Identification of Enteroviruses by RT-PCR and Amplicon Sequencing," Journal of Clinical Virology, 2003, vol. 26 (3), pp. 375-377.
Oberste M.S., et al., "Molecular Epidemiology and Type-Specific Detection of Echovirus 11 Isolates from the Americas, Europe, Africa, Australia, Southern Asia and the Middle East," Virus Research, 2003, vol. 91 (2), pp. 241-248.
Oberste M.S., et al., "Molecular Phylogeny and Proposed Classification of the Simian Picornaviruses," Journal of Virology, 2002, vol. 76 (3), pp. 1244-1251.
Office Action mailed Apr. 1, 2004 for U.S. Appl. No. 10/156,608, filed May 24, 2002.
Office Action mailed May 1, 2006 for U.S. Appl. No. 10/660,998, filed Sep. 12, 2003.
Office Action mailed Feb. 2, 2011 for U.S. Appl. No. 11/869,449, filed Oct. 9, 2007.
Office Action mailed Jan. 2, 2009 for U.S. Appl. No. 11/060,135, filed Feb. 17, 2005.
Office Action mailed Jun. 2, 2006 for U.S. Appl. No. 10/933,928, filed Sep. 3, 2004.
Office Action mailed Jun. 2, 2008 for U.S. Appl. No. 11/331,978, filed Jan. 13, 2006.
Office Action mailed Oct. 2, 2008 for U.S. Appl. No. 11/233,630, filed Sep. 21, 2005.
Office Action mailed Oct. 2, 2009 for Japanese Application No. 2005508560 filed Dec. 5, 2003.
Office Action mailed Aug. 3, 2006 for U.S. Appl. No. 10/660,998, filed Sep. 12, 2003.
Office Action mailed Aug. 3, 2009 for U.S. Appl. No. 11/754,174, filed May 25, 2007.
Office Action mailed Dec. 3, 2003 for U.S. Appl. No. 10/325,527, filed Dec. 18, 2002.
Office Action mailed Feb. 3, 2011 for U.S. Appl. No. 12/326,800, filed Dec. 2, 2008.
Office Action mailed Nov. 3, 2008 for U.S. Appl. No. 10/728,486, filed Dec. 5, 2003.
Office Action mailed Apr. 4, 2008 for U.S. Appl. No. 10/829,826, filed Apr. 22, 2004.
Office Action mailed Dec. 4, 2006 for Indian Application No. 1136KOLNP2003 filed Mar. 4, 2002.
Office Action mailed Feb. 4, 2009 for U.S. Appl. No. 11/404,561, filed Apr. 12, 2006.
Office Action mailed Jun. 4, 2009 for U.S. Appl. No. 10/754,415 filed Jan. 9, 2004.
Office Action mailed May 4, 2010 for U.S. Appl. No. 90/010,447, filed Apr. 9, 2009.
Office Action mailed May 4, 2010 for U.S. Appl. No. 90/010,448, filed Apr. 9, 2009.
Office Action mailed Nov. 4, 2009 for European Application No. 02709785.6 filed Mar. 4, 2002.
Office Action mailed Sep. 4, 2008 for Australian Application No. 2003297687 filed Dec. 5, 2003.
Office Action mailed Aug. 5, 2010 for European Application No. 02709785.6 filed Mar. 4, 2002.
Office Action mailed Sep. 5, 2006 for U.S. Appl. No. 10/660,996, filed Sep. 12, 2003.
Office Action mailed Jan. 6, 2011 for Israel Application No. 157661 filed Mar. 4, 2002.

(56) References Cited

OTHER PUBLICATIONS

Office Action mailed Jul. 6, 2006 for U.S. Appl. No. 10/660,122, filed Sep. 11, 2003.
Office Action mailed Jul. 6, 2007 for U.S. Appl. No. 10/829,826, filed Apr. 22, 2004.
Office Action mailed Mar. 6, 2009 for U.S. Appl. No. 11/233,630, filed 21, 2005.
Office Action mailed Nov. 6, 2002 for U.S. Appl. No. 09/798,007, filed Mar. 2, 2001.
Office Action mailed Apr. 7, 2009 for Canadian Application No. 2525498 filed May 13, 2004.
Office Action mailed Apr. 7, 2009 for European Application No. 07760292.8 filed Apr. 6, 2007.
Office Action mailed Apr. 7, 2009 for U.S. Appl. No. 10/660,998, filed Sep. 12, 2003.
Office Action mailed Aug. 7, 2007 for U.S. Appl. No. 10/660,998, filed Sep. 12, 2003.
Office Action mailed Feb. 7, 2008 for European Application No. 03796752.8 filed Dec. 5, 2003.
Office Action mailed Jun. 7, 2010 for European Application No. 06800205.4 filed Jul. 21, 2006.
Office Action mailed Jan. 8, 2003 for U.S. Appl. No. 09/798,007, filed Mar. 2, 2001.
Office Action mailed Jan. 8, 2007 for U.S. Appl. No. 09/891,793, filed Jun. 26, 2001.
Office Action mailed Mar. 8, 2005 for U.S. Appl. No. 09/891,793, filed Jun. 26, 2001.
Office Action mailed Mar. 8, 2007 for U.S. Appl. No. 11/060,135, filed Feb. 17, 2005.
Office Action mailed Sep. 8, 2006 for Chinese Application No. 02809122.1 filed Mar. 4, 2002.
Office Action mailed Dec. 9, 2004 for U.S. Appl. No. 10/156,608, filed May 24, 2002.
Office Action mailed Dec. 9, 2009 for U.S. Appl. No. 90/010,210, filed Jun. 27, 2008.
Office Action mailed Dec. 9, 2009 for U.S. Appl. No. 90/010,447, filed Apr. 9, 2009.
Office Action mailed Dec. 9, 2009 for U.S. Appl. No. 90/010,448, filed Apr. 9, 2009.
Office Action mailed Feb. 9, 2007 for Chinese Application No. 02809122.1 filed Mar. 4, 2002.
Office Action mailed Jan. 9, 2008 for Japanese Application No. 2002570692 filed Mar. 4, 2002.
Office Action mailed Jul. 9, 2008 for U.S. Appl. No. 10/660,122, filed Sep. 11, 2003.
Office Action mailed Jul. 9, 2008 for U.S. Appl. No. 11/331,987, filed Jan. 13, 2006.
Office Action mailed Mar. 9, 2004 for U.S. Appl. No. 09/891,793, filed Jun. 26, 2001.
Office Action mailed Nov. 9, 2010 for U.S. Appl. No. 11/331,987, filed Jan. 13, 2006.
Office Action mailed Dec. 10, 2008 for U.S. Appl. No. 10/829,826, filed Apr. 22, 2004.
Office Action mailed Dec. 10, 2009 for U.S. Appl. No. 11/929,910, filed Oct. 30, 2007.
Office Action mailed Feb. 10, 2005 for U.S. Appl. No. 09/798,007, filed Mar. 2, 2001.
Office Action mailed Feb. 10, 2006 for Australian Application No. 2002244250 filed Mar. 4, 2002.
Office Action mailed 10, 2009 for U.S. Appl. No. 90/010,210, filed 27, 2008.
Office Action mailed Jun. 10, 2010 for U.S. Appl. No. 90/010,447, filed Apr. 9, 2009.
Office Action mailed Jun. 10, 2010 for U.S. Appl. No. 90/010,448, filed Apr. 9, 2009.
Office Action mailed Oct. 10, 2007 for U.S. Appl. No. 10/754,415, filed Jan. 9, 2004.
Office Action mailed Sep. 10, 2008 for Australian Application No. 2003302236 filed Dec. 5, 2003.
Office Action mailed 11, 2005 for U.S. Appl. No. 09/891,793, filed 26, 2001.
Office Action mailed Aug. 11, 2010 for U.S. Appl. No. 90/010,447, filed Apr. 9, 2009.
Office Action mailed Aug. 11, 2010 for U.S. Appl. No. 90/010,448, filed Apr. 9, 2009.
Office Action mailed Dec. 11, 2007 for U.S. Appl. No. 10/660,998, filed Sep. 12, 2003.
Office Action mailed Jul. 11, 2003 for U.S. Appl. No. 09/798,007, filed Mar. 2, 2001.
Office Action mailed Jun. 11, 2010 for U.S. Appl. No. 90/010,210, filed Jun. 27, 2008.
Office Action mailed Mar. 11, 2005 for U.S. Appl. No. 10/325,527, filed Dec. 18, 2002.
Office Action mailed May 11, 2007 for U.S. Appl. No. 10/728,486, filed Dec. 5, 2003.
Office Action mailed Jul. 12, 2006 for U.S. Appl. No. 09/891,793, filed Jun. 26, 2001.
Office Action mailed Jul. 12, 2006 for U.S. Appl. No. 10/660,996, filed Sep. 12, 2003.
Office Action mailed Jun. 12, 2008 for U.S. Appl. No. 10/754,415, filed Jan. 9, 2004.
Office Action mailed May 12, 2002 for U.S. Appl. No. 09/798,007, filed Mar. 2, 2001.
Office Action mailed Aug. 13, 2009 for U.S. Appl. No. 11/674,538, filed Feb. 13, 2007.
Office Action mailed Jul. 13, 2004 for U.S. Appl. No. 09/891,793, filed Jun. 26, 2001.
Office Action mailed Jul. 13, 2007 for U.S. Appl. No. 11/233,630, filed Sep. 21, 2005.
Office Action mailed Jul. 13, 2010 for U.S. Appl. No. 11/929,930, filed Oct. 30, 2007.
Office Action mailed Mar. 13, 2006 for U.S. Appl. No. 10/754,415, filed Jan. 9, 2004.
Office Action mailed Nov. 13, 2003 for U.S. Appl. No. 09/891,793, filed Jun. 26, 2001.
Office Action mailed Sep. 13, 2006 for U.S. Appl. No. 09/891,793, filed Jun. 26, 2001.
Office Action mailed Jul. 14, 2004 for U.S. Appl. No. 10/326,642, filed Dec. 18, 2002.
Office Action mailed Jun. 14, 2004 for U.S. Appl. No. 09/891,793, filed Jun. 26, 2001.
Office Action mailed Mar. 14, 2011 for U.S. Appl. No. 11/930,002, filed Oct. 30, 2007.
Office Action mailed Aug. 15, 2008 for U.S. Appl. No. 11/331,978, filed Jan. 13, 2006.
Office Action mailed Aug. 15, 2013 for European Application No. 09792626.5 filed Sep. 16, 2009.
Office Action mailed Dec. 15, 2008 for Israel Application No. 157661 filed Mar. 4, 2002.
Office action mailed Dec. 15, 2010 for Canadian Application No. 2508726 filed Dec. 5, 2003.
Office Action mailed Jan. 15, 2008 for Israel Application No. 157661 filed Mar. 4, 2002.
Office Action mailed Jul. 15, 2009 for U.S. Appl. No. 11/060,135, filed Feb. 17, 2005.
Office Action mailed Mar. 15, 2010 for European Application No. 08730682.5 filed Feb. 25, 2008.
Office Action mailed Nov. 15, 2007 for U.S. Appl. No. 11/331,978, filed Jan. 13, 2006.
Office Action mailed Sep. 15, 2005 for U.S. Appl. No. 10/156,608, filed May 24, 2002.
Office Action mailed Apr. 16, 2002 for U.S. Appl. No. 09/798,007, filed Mar. 2, 2001.
Office Action mailed Apr. 16, 2008 for U.S. Appl. No. 11/233,630, filed Sep. 21, 2005.
Office Action mailed Apr. 16, 2009 for U.S. Appl. No. 90/010,210, filed Jun. 27, 2008.
Office Action mailed Aug. 16, 2004 for U.S. Appl. No. 10/325,527, filed Dec. 18, 2002.
Office Action mailed Aug. 16, 2010 for U.S. Appl. No. 11/929,707, filed Oct. 30, 2007.

(56) References Cited

OTHER PUBLICATIONS

Office Action mailed Feb. 16, 2011 for U.S. Appl. No. 11/929,910, filed Oct. 30, 2007.
Office Action mailed Jul. 16, 2007 for U.S. Appl. No. 11/331,987, filed Jan. 13, 2006.
Office Action mailed Mar. 16, 2006 for U.S. Appl. No. 09/891,793, filed Jun. 26, 2001.
Office Action mailed Mar. 16, 2010 for Canadian Application No. 2616281 filed Jul. 21, 2006.
Office Action mailed May 16, 2008 for U.S. Appl. No. 11/404,561, filed Apr. 12, 2006.
Office Action mailed Nov. 16, 2009 for Japanese Application No. 2005508488 filed Dec. 5, 2003.
Office Action mailed Jun. 17, 2008 for U.S. Appl. No. 11/582,863, filed Oct. 17, 2006.
Office Action mailed Mar. 17, 2006 for U.S. Appl. No. 10/660,122, filed Sep. 11, 2003.
Office Action mailed Nov. 17, 2006 for U.S. Appl. No. 10/754,415, filed Jan. 9, 2004.
Office Action mailed Oct. 17, 2007 for U.S. Appl. No. 10/728,486, filed Dec. 5, 2003.
Office Action mailed Oct. 17, 2008 for U.S. Appl. No. 11/331,978, filed Jan. 13, 2006.
Office Action mailed Sep. 17, 2008 for European Application No. 03796752.8 filed Dec. 5, 2003.
Office Action mailed Sep. 17, 2008 for U.S. Appl. No. 10/660,122, filed Sep. 11, 2003.
Office Action mailed Aug. 18, 2010 for U.S. Appl. No. 12/561,175, filed Sep. 16, 2009.
Office Action mailed Feb. 18, 2010 for European Application No. 03814656.9 filed Dec. 5, 2003.
Office Action mailed Jan. 18, 2011 for U.S. Appl. No. 11/930,108 filed Oct. 31, 2007.
Office Action mailed May 18, 2005 for New Zealand Application No. 527857 filed Mar. 4, 2002.
Office Action mailed Sep. 18, 2006 for U.S. Appl. No. 10/660,997, filed Sep. 12, 2003.
Office Action mailed Sep. 18, 2008 for Australian Application No. 2003298030 filed Dec. 5, 2003.
Office Action mailed Sep. 18, 2008 for U.S. Appl. No. 10/660,998, filed Sep. 12, 2003.
Office Action mailed Jan. 19, 2007 for U.S. Appl. No. 11/059,776, filed Feb. 17, 2005.
Office Action mailed May 19, 2005 for U.S. Appl. No. 09/891,793, filed Jun. 26, 2001.
Office Action mailed Nov. 19, 2004 for U.S. Appl. No. 10/156,608, filed May 24, 2002.
Office Action mailed Oct. 19, 2007 for U.S. Appl. No. 11/210,516, filed Aug. 24, 2005.
Office Action mailed Sep. 19, 2006 for U.S. Appl. No. 10/660,122, filed Sep. 11, 2003.
Office Action mailed Sep. 19, 2007 for U.S. Appl. No. 10/660,122, filed Sep. 11, 2003.
Office Action mailed Apr. 20, 2007 for U.S. Appl. No. 10/660,122, filed Sep. 11, 2003.
Office Action mailed Apr. 20, 2009 for U.S. Appl. No. 10/891,337, filed Jul. 14, 2004.
Office Action mailed Dec. 20, 2006 for U.S. Appl. No. 10/728,486, filed Dec. 5, 2003.
Office Action mailed Jul. 20, 2005 for U.S. Appl. No. 10/156,608, filed May 24, 2002.
Office Action mailed Jun. 20, 2002 for U.S. Appl. No. 09/798,007, filed Mar. 2, 2001.
Office Action mailed Nov. 20, 2003 for U.S. Appl. No. 10/323,438, filed Dec. 18, 2002.
Office Action mailed Nov. 20, 2006 for U.S. Appl. No. 09/891,793, filed Jun. 26, 2001.
Office Action mailed Nov. 20, 2006 for European Application No. 02709785.6 filed Mar. 4, 2002.
Office Action mailed Sep. 20, 2010 for U.S. Appl. No. 90/010,447, filed Apr. 9, 2009.
Office Action mailed Sep. 20, 2010 for U.S. Appl. No. 90/010,448, filed Apr. 9, 2009.
Office Action mailed Apr. 21, 2009 for U.S. Appl. No. 90/010,209, filed Jun. 27, 2008.
Office Action mailed Mar. 21, 2008 for U.S. Appl. No. 10/660,122, filed Sep. 11, 2003.
Office Action mailed May 21, 2008 for U.S. Appl. No. 10/943,344, filed Sep. 17, 2004.
Office Action mailed Nov. 21, 2003 for U.S. Appl. No. 10/326,642, filed Dec. 18, 2002.
Office Action mailed Nov. 21, 2006 for U.S. Appl. No. 10/660,997, filed Sep. 12, 2003.
Office Action mailed Oct. 21, 2005 for U.S. Appl. No. 10/326,641, filed Dec. 18, 2002.
Office Action mailed Oct. 21, 2009 for U.S. Appl. No. 12/326,800, filed Dec. 2, 2008.
Office Action mailed Apr. 22, 2009 for U.S. Appl. No. 11/491,376, filed Jul. 21, 2006.
Office Action mailed Jul. 22, 2008 for U.S. Appl. No. 90/010,209, filed Jun. 27, 2008.
Office Action mailed Jul. 22, 2008 for U.S. Appl. No. 90/010,210, filed Jun. 27, 2008.
Office Action mailed Nov. 22, 2006 for U.S. Appl. No. 10/660,996, filed Sep. 12, 2003.
Office Action mailed Oct. 22, 2007 for U.S. Appl. No. 11/331,987, filed Jan. 13, 2006.
Office Action mailed Sep. 22, 2003 for U.S. Appl. No. 09/798,007, filed Mar. 2, 2001.
Office Action mailed Sep. 22, 2010 for Canadian Application No. 2510007 filed Dec. 5, 2003.
Office Action mailed Apr. 23, 2010 for U.S. Appl. No. 90/010,210, filed Jun. 27, 2008.
Office Action mailed Feb. 23, 2009 for U.S. Appl. No. 10/943,344, filed Sep. 17, 2004.
Office Action mailed Jan. 23, 2008 for U.S. Appl. No. 10/728,486, filed Dec. 5, 2003.
Office Action mailed Jan. 23, 2008 for U.S. Appl. No. 11/059,776, filed Feb. 17, 2005.
Office Action mailed May 23, 2003 for U.S. Appl. No. 09/891,793, filed Jun. 26, 2001.
Office Action mailed May 23, 2005 for U.S. Appl. No. 10/156,608, filed May 24, 2002.
Office Action mailed Oct. 23, 2003 for New Zealand Application No. 527857 filed Mar. 4, 2002.
Office Action mailed Apr. 24, 2009 for U.S. Appl. No. 90/010,447, filed Apr. 9, 2009.
Office Action mailed Apr. 24, 2009 for U.S. Appl. No. 90/010,448, filed Apr. 9, 2009.
Office Action mailed Aug. 24, 2010 for U.S. Appl. No. 90/010,210, filed Jun. 27, 2008.
Office Action mailed Dec. 24, 2004 for New Zealand Application No. 527857 filed Mar. 4, 2002.
Office Action mailed Feb. 24, 2004 for U.S. Appl. No. 10/326,642, filed Dec. 18, 2002.
Office Action mailed Jan. 24, 2005 for U.S. Appl. No. 10/326,642, filed Dec. 18, 2002.
Office Action mailed Jan. 24, 2007 for U.S. Appl. No. 10/660,998, filed Sep. 12, 2003.
Office Action mailed Jul. 24, 2007 for Mexican Application No. PAA2003007927 filed Sep. 2, 2003.
Office Action mailed Jul. 24, 2007 for U.S. Appl. No. 11/060,135, filed Feb. 17, 2005.
Office Action mailed Jul. 24, 2009 for U.S. Appl. No. 11/754,182, filed May 25, 2007.
Office Action mailed Jun. 24, 2008 for European Application No. 06800205.4 filed Jul. 21, 2006.
Office Action mailed Mar. 24, 2011 for U.S. Appl. No. 11/929,930, filed Oct. 30, 2007.
Office Action mailed Nov. 24, 2009 for U.S. Appl. No. 90/010,210, filed Jun. 27, 2008.

(56) References Cited

OTHER PUBLICATIONS

Office Action mailed Sep. 24, 2009 for U.S. Appl. No. 90/010,210, filed Jun. 27, 2008.
Office Action mailed Aug. 25, 2009 for U.S. Appl. No. 11/754,169, filed May 25, 2007.
Office Action mailed Jun. 25, 2009 for U.S. Appl. No. 11/869,449, filed Oct. 9, 2007.
Office Action mailed Jun. 25, 2009 for U.S. Appl. No. 90/010,210, filed Jun. 27, 2008.
Office Action mailed Mar. 25, 2008 for U.S. Appl. No. 11/060,135, filed Feb. 17, 2005.
Office Action mailed Aug. 26, 2003 for U.S. Appl. No. 09/891,793, filed Jun. 26, 2001.
Office Action mailed Aug. 26, 2010 for Canadian Application No. 2508584 filed Dec. 5, 2003.
Office Action mailed Jul. 26, 2004 for U.S. Appl. No. 10/323,438, filed Dec. 18, 2002.
Office Action mailed May 26, 2005 for U.S. Appl. No. 10/156,608, filed May 24, 2002.
Office Action mailed May 26, 2006 for U.S. Appl. No. 10/660,997, filed Sep. 12, 2003.
Office Action mailed Feb. 27, 2003 for U.S. Appl. No. 09/798,007, filed Mar. 2, 2001.
Office Action mailed Feb. 27, 2007 for U.S. Appl. No. 10/754,415, filed Jan. 9, 2004.
Office Action mailed Feb. 27, 2007 for U.S. Appl. No. 10/943,344, filed Sep. 17, 2004.
Office Action mailed Jul. 27, 2006 for U.S. Appl. No. 10/728,486, filed Dec. 5, 2003.
Office Action mailed Jul. 27, 2009 for Canadian Application No. 2439655 filed Mar. 4, 2002.
Office Action mailed Aug. 28, 2006 for U.S. Appl. No. 10/754,415, filed Jan. 9, 2004.
Office Action mailed Feb. 28, 2006 for U.S. Appl. No. 10/660,996, filed Sep. 12, 2003.
Office Action mailed Jul. 28, 2009 for U.S. Appl. No. 11/754,163, filed May 25, 2007.
Office Action mailed Jul. 28, 2010 for U.S. Appl. No. 90/010,210, filed Jun. 27, 2008.
Office Action mailed May 28, 2003 for U.S. Appl. No. 09/798,007, filed Mar. 2, 2001.
Office Action mailed Mar. 29, 2010 for Australian Application No. 2006272776 filed Jul. 21, 2006.
Office Action mailed May 29, 2007 for U.S. Appl. No. 11/059,776, filed Feb. 17, 2005.
Office Action mailed Oct. 29, 2009 for U.S. Appl. No. 90/010,447, filed Apr. 9, 2009.
Office Action mailed Oct. 29, 2009 for U.S. Appl. No. 90/010,448, filed Apr. 9, 2009.
Office Action mailed Aug. 30, 2007 for U.S. Appl. No. 10/754,415, filed Jan. 9, 2004.
Office Action mailed Jul. 30, 2008 for Australian Application No. 2004248107 filed Apr. 23, 2004.
Office Action mailed Jul. 30, 2009 for Japanese Application No. 2002570692 filed Mar. 4, 2002.
Office Action mailed Jun. 30, 2004 for U.S. Appl. No. 09/798,007, filed Mar. 2, 2001.
Office Action mailed Jun. 30, 2010 for U.S. Appl. No. 90/010,210, filed Jun. 27, 2008.
Office Action mailed Jun. 30, 2010 for U.S. Appl. No. 90/010,447, filed Apr. 9, 2009.
Office Action mailed Jun. 30, 2010 for U.S. Appl. No. 90/010,448, filed Apr. 9, 2009.
Office Action mailed May 30, 2006 for U.S. Appl. No. 10/660,996, filed Sep. 12, 2003.
Office Action mailed Nov. 30, 2009 for U.S. Appl. No. 10/660,122, filed Sep. 11, 2003.
Office Action mailed Sep. 30, 2005 for Chinese Application No. 02809122.1 filed Mar. 4, 2002.
Office Action mailed Jan. 31, 2003 for U.S. Appl. No. 09/798,007, filed Mar. 2, 2001.
Office Action mailed Jan. 31, 2007 for Philippines Application No. PH12003500824 filed Mar. 4, 2002.
O"Guinn M.L., et al., "Field Detection of Eastern Equine Encephalitis Virus in the Amazon Basin Region of Peru Using Reverse Transcription-Polymerase Chain Reaction Adapted for Fieldldentification of Arthropod-Borne Pathogens," American Journal of Tropical Medicine and Hygiene, 2004, vol. 70 (2), pp. 164-171.
Oizumi N., et al., "Relationship Between Mutations in the DNA Gyrase and Topoisomerase IV Genes and Nadifloxacin Resistance in Clinically Isolated Quinolone-Resistant *Staphylococcus aureus*," Journal of Infection and Chemotherapy, 2001, vol. 7 (3), pp. 191-194.
Okada M., et al., "Detection and Sequence-Based Typing of Human Adenoviruses Using Sensitiveuniversal Primer Sets for the Hexon Gene," Archives of Virology, 2007, vol. 152 (1), pp. 1-9.
Okuma K., et al., "Dissemination of New Methicillin-Resistant *Staphylococcus aureus* Clones in the Community," Journal of Clinical Microbiology, 2002, vol. 40 (11), pp. 4289-4294.
Oliveira D.C., et al., "Genetic Organization of the Downstream Region of the mecA Element inMethicillin-Resistant *Staphylococcus aureus* Isolates Carrying Different Polymorphisms of This Region," Antimicrobial Agents and Chemotherapy, 2000, vol. 44 (7), pp. 1906-1910.
Oliveira D.C., et al., "Multiplex PCR Strategy for Rapid Identification of Structural Types and Variants of the mec Element in Methicillin-Resistant *Staphylococcus aureus*," Antimicrobial Agents and Chemotherapy, 2002, vol. 46 (7), pp. 2155-2161.
Olsen B., et al., "Transhemispheric Exchange of Lyme Disease Spyrochetes by Seabirds," Journal of Clinical Microbiology, 1995, vol. 33 (12), pp. 3270-3274.
Osiowy C., et al., "Direct Detection of Respiratory Syncytial Virus, Parainfluenza Virus, and Adenovirus in Clinical Respiratory Specimens by a Multiplex Reverse Transcription-PCR Assay," Journal of Clinical Microbiology, 1998, vol. 36 (11), pp. 3149-3154.
Ostrander E.A., et al., "Identification and Characterization of Dinucleotide Repeat (CA)n Markers for Genetic Mapping in Dog," Genomics, 1993, vol. 16 (1), pp. 207-213.
Ounissi H., et al., "Gene Homogeneity for Aminoglycoside-Modifying Enzymes in Gram-PositiveCocci," Antimicrobial Agents and Chemotherapy, 1990, 34 (11), 2164-2168.
Palys T., et al., "Discovery and Classification of Ecological Diversity in the Bacterial World: the Role of DNA Sequence Data," International Journal of Systematic Bacteriology, 1997, vol. 47 (4), pp. 1145-1156.
Pan Z.Q., et al., "Oligonucleotide-Targeted Degradation of U1 and U2 snRNAs Reveals Differential Interactions of Simian Virus 40 pre-mRNAs with snRNPs," Nucleic Acids Research, 1989, vol. 17 (16), pp. 6553-6568.
Pannetier C., et al., "Quantitative Titration of Nucleic Acids by Enzymatic Amplification Reactions Run to Saturation," Nucleic Acids Research, 1993, vol. 21 (3), pp. 577-583.
Parson W., et al., "Population Data for 101 Austrian Caucasian Mitochondrial DNA d-Loop Sequences: Application of mtDNA Sequence Analysis to a Forensic Case," International Journal of Legal Medicine, 1998, vol. 111 (3), pp. 124-132.
Partial European Search Report for Application No. EP01106974, mailed on Dec. 16, 2002, 2 pages.
Pastorino B., et al., "Development of a TagMan PCR Assay Without RNA Extraction Step for the Detection and Quantification of African Chikungunya Viruses," Journal of Virological Methods, 2005, vol. 124 (1-2), pp. 65-71.
Paterson A.H., et al., "Fine Mapping of Quantitative Trait Loci Using Selected Overlapping Recombinant Chromosomes, in an Interspecies Cross of Tomato," Genetics, 1990, vol. 124 (3), pp. 735-742.
Pawa A., et al., "Co-Transfer of Plasmids in Association with Conjugative Transfer of Mupirocin or Mupirocin and Penicillin Resistance in Methicillin-Resistant *Staphylococcus aureus*," Journal of Medicinal Microbiology, 2000, vol. 49 (12), pp. 1103-1107.
Payne D., et al., "Antimicrobials: The Challenge of Antibiotic Resistant Bacterial Pathogens: The Medical Need, the Market and Prospects for New Antimicrobial Agents," Current Opinion in Microbiology, 2004, vol. 7, pp. 435-438.

(56) References Cited

OTHER PUBLICATIONS

Peng X., et al., "Rapid Detection of Shigella Species in Environmental Sewage by an Immunocapture PCR with Universal Primers," Applied and Environmental Microbiology, 2002, vol. 68 (5), pp. 2580-2583.
Perez-Roth E., et al., "Multiplex PCR for Simultaneous Identification of *Staphylococcus aureus* and Detection of Methicillin and Mupirocin Resistance," Journal of Clinical Microbiology, 2001, vol. 39 (11), pp. 4037-4041.
Peters S.E., et al., "Quantification of the Detection of *Pneumocystis carinii* by DNA Amplification," Molecular and Cellur Probes, 1992, vol. 6 (2), pp. 115-117.
Pfeffer M., et al., "Genus-Specific Detection of Alphaviruses by a Semi-Nested ReverseTranscription-Polymerase Chain Reaction," American Journal of Tropical Medicine and Hygiene, 1997, vol. 57 (6), pp. 709-718.
Pfeffer M., et al., "Specific Detection of Chikungunya Virus Using a RT-PCR/Nested PCR Combination," Journal of Veterinary Medicine B, 2002, vol. 49 (1), pp. 49-54.
Pieles U., et al., "Matrix-Assisted Laser Desorption Ionization Time-of-Flight Spectrometry: APowerfl Tool for the Mass and Sequence Analysis of Natural and Modified Oligonucleotides," Nucleic Acids Research, 1993, vol. 21 (14), pp. 3191-3196.
Pillai S.D., et al., "Rapid Molecular Detection of Microbial Pathogens: Breakthroughs and Challenges," Archives of Virology, 1997, vol. 13, pp. 67-82.
Piper J., et al., "Commercially Available Technique for Rapid Laboratory Detection of MethicillinResistance Among *Staphylococcus aureus*," Diagnostic Microbiology and Infectious Disease, 1988, vol. 11 (3), pp. 177-180.
Poddar S.K. et al., "Detection of Adenovirus usig PCR and Molecular Beacon," Journal of Virological Methods, 1999, vol. 82 (1), pp. 19-26.
Pomerantz S.C., et al., "Determination of Oligonucleotide Composition from Mass Spectrometrically Measured Molecular Weight," Journal of the American Society for Mass Spectrometry, 1993, vol. 4 (3), pp. 204-209.
Pring-Akerblom P., et al., "Multiplex Polymerase Chain Reaction for Subgenus-Specific Detection of Human Adenoviruses in Clinical Samples," Journal of Medical Virology, 1999, vol. 58 (1), pp. 87-92.
Pring-Akerblom P., et al., "PCR-Based Detection and Typing of Human Adenoviruses in Clinical Samples," Research in Virology, 1997, vol. 148 (3), pp. 225-231.
Promega. T4 Polynucleotide Kinase, Technical Bulletin No. 519, 2002.
Puthavathana P., et al., "Molecular Characterization of the Complete Genome of Human Influenza H5N1 Virus Isolates from Thailand," Journal of General Virology, 2005, vol. 86 (2), pp. 423-433.
Qadri S.M., et al., "Rapid Detection of Methicillin-Resistant *Staphylococcus aureus* by CrystalMRSA ID System," Journal of Clinical Microbiology, 1994, vol. 32 (7), pp. 1830-1832.
Raaum R.L., et al., "Catarrhine Primate Divergence Dates Estimated from Complete Mitochondria Genomes: Concordance with Fossil and Nuclear DNA Evidence," Journal of Human Evolution, 2005, vol. 48 (3), pp. 237-257.
Ramisse V., et al., "Identification and Characterization of *Bacillus* Anthracis by Multiplex PCR Analysis of Sequences on Plasmids pX01 and pX02 and Chromosomal DNA," Fems Microbiology Letters, 1996, vol. 145 (1), pp. 9-16.
Reid S.M., et al., "Primary Diagnosis of Foot-and-Mouth Disease by Reverse Transcription Polymerase Chain Reaction," Journal of Virological Methods, 2000, vol. 89 (1-2), pp. 167-176.
Reilly K., et al., "Design and Use of 16s Ribosomal DNA-Directed Primers in Competitive PCRs to Enumerate Proteolytic Bacteria in the Rumen," Microbial Ecology, 2002, vol. 43 (2), pp. 259-270.
Reischl U., "Application of Molecular Biology-Based Methods to theDiagnosis of Infectious Diseases 1, e72-e77.," Frontiers in Bioscience, 1996, vol. 1 (1), pp. e72-e77.
Reischl U., et al., "Rapid Identification of Methicillin-Resistant *Staphylococcus aureus* and Simultaneous Species Confirmation Using Real-Time Fluorescence PCR" Journal of Clinical Microbiology, 2000, vol. 38 (6), pp. 2429-2433.
Response to Amendment under Rule 312 mailed Nov. 5, 2013 for U.S. Appl. No. 13/595,189, filed Aug. 27, 2012.
Roberts M.M., et al., "Three-Dimensional Structure of the Adenovirus Major Coat Protein Hexon," Science, 1986, vol. 232 (4754), pp. 1148-1151.
Roberts M.S., et al., "Recombination and Migration Rates in Natural Populations of *Bacillus subtilis* and *Bacillus mojavensis*," Evolution, 1995, vol. 49 (6), pp. 1081-1094.
Robinson D.A., et al., "Multilocus Sequence Typing and the Evolution of Methicillin-Resistant *Staphylococcus aureus*," Clinical Microbiology and Infection, 2004, vol. 10, pp. 92-97.
Rong S., et al., "Design and Application of 60mer Oligonucleotide Microarray in SARS Coronavirus Detection," Chinese Science Bulletin, 2003, vol. 48 (12), pp. 1165-1169.
Ross P., et al., "High Level Multiplex Genotyping by MALDI-TOF Mass Spectrometry," Nature Biotechnology, 1998, vol. 16 (13), pp. 1347-1351.
Ross P.L., et al., "Analysis of DNA Fragments from Conventional and Microfabricated PCR Devices Using Delayed Extraction MALDI-TOF Mass Spectrometry," Analytical Chemistry, 1998, vol. 70 (10), pp. 2067-2073.
Ross P.L., et al., "Discrimination of Single-Nucleotide Polymorphisms in Human DNA Using Peptide Nucleic Acid Probes Detected by MALDI-TOF Mass Spectrometry," Analytical Chemistry, 1997, vol. 69 (20), pp. 4197-4202.
Rota P.A., et al., "Sequencing of a cDNA Clone of the Nucleprotein Gene of Influenza B/Ann Arbor/1,/86," Nucleic Acids Research, 1989, vol. 17 (9), p. 3595.
Ruan Y., et al., "Comparative Full-Length Genome Sequence Analysis of 14 SARS Coronavirus Isolates and Common Mutatons Associated with the Putative Origins of Infection," The Lancet, 2003, vol. 361, pp. 1779-1785, 1832.
Ruest A., et al., "Comparison of the Directigen Flu A+B test, the QuickVue Influenza Test, and Clinical Case Definition to Viral Culture and Reverse Transcription-PCR for Rapid Diagnosis of Influenza Virus Infection," Journal of Clinical Microbiology, 2003, vol. 41 (8), pp. 3487-3493.
Rupf S., et al., "Quantitative Determination of *Streptococcus* Mutans by using Competitive Polymerasechain Reaction," European Journal of Oral Sciences, 1999, vol. 107 (2), pp. 75-81.
Russell K.L., et al., "Transmission Dynamics and Prospective Environmental Sampling of Adenovirus in a Military Recruit Setting," Journal of Infectious Diseases, 2006, vol. 194 (7), pp. 877-885.
Sabat A., et al., "Comparison of PCR-Based Methods for Typing *Staphylococcus aureus* Isolates," Journal of Clinical Microbiology, 2006, vol. 44 (10), pp. 3804-3807.
Sackesen C., et al., "Use of Polymerase Chain Reaction for Detection of Adenovirus in Children Withor Without Wheezing," Turkish Journal of Pediatrics, 2005, vol. 47 (3), pp. 227-231.
Sakai H., et al., "Simultaneous Detection of *Staphylococcus aureus* and Coagulase-Negative Staphylococci in Positive Blood Cultures by Real-Time PCR with two Fluorescene Resonance Energy Transfer Probe Sets," Journal of Clinical Microbiology, 2004, vol. 42 (12), pp. 5739-5744.
Sala M., et al., "Ambiguous Base Pairing of the Purine Analogue 1-(2-Deoxy-B-D—Ribofuranosyl)-Imidazole-4- Carboxamide During PCR," Nucelic Acids Research, 1996, vol. 24 (17), pp. 3302-3306.
Sambrook J., et al., "Molecular Cloning—A Laboratory Manual," 1989, Cold Spring Harbor Laboratory Press, Table of Contents.
Sampath R., et al., "Global Surveillance of Emerging Influenza Virus Genotypes by Mass Spectrometry," Plos One, 2007, vol. 2 (5), pp. e489.
Sampath R., et al., "Rapid Identification of Emerging Infectious Agents using PCR and Electrospray Ionization Mass Spectrometry," Annals of New York Academy of Science, 2007, vol. 1102, pp. 109-120.
Sampath R., et al., "Rapid Identification of Emerging Pathogens: Coronavirus," Emerging Infectious Diseases, 2005, vol. 11 (3), pp. 373-379.

(56) References Cited

OTHER PUBLICATIONS

Sanchez A., et al., "Detection and Molecular Characterization of Ebola Viruses Causing of Ebola Viruses Causing Disease in Human and Nonhuman Primates," Journal of Infectious Diseases, 1999, vol. 179 (1), pp. S164-S169.

Sanchez J.L., et al., "Epidemic of Adenovirus-Induced Respiratory Illness Among US Military Recruits: Epidemiologic and Immunologic Risk Factors in Healthy, Young adults," Journal of Medical Virology, 2001, vol. 65 (4), pp. 710-718.

Sanchez-Seco M.P., et al., "A Generic Nested-RT-PCR followed by Sequencing for Detection and Identification of Members of the Alphavirus Genus," Journal of Virological Methods, 2001, vol. 95 (1-2), pp. 153-161.

Santos S.R., et al., "Identification and Phylogenetic Sorting of Bacterial Lineages with Universally Conserved Genes and Proteins," Environmental Microbiology, 2004, vol. 6 (7), pp. 754-759.

Sarantis H., et al., "Comprehensive Detection and Serotyping of Human Adenoviruses by PCR and Sequencing," Journal of Clinical Microbiology, 2004, vol. 42 (9), pp. 3963-3969.

Sauer S., et al., "A Novel Procedure for Efficient Genotyping of Single Nucleotide Polymorphisms," Nucleic Acids Research, 2000, vol. 28 (5), pp. E13.1-E13.8.

Scaramozzino N., et al., "Comparison of Flavivirus Universal Primer Pairs and Development of a Rapid, Highly Sensitive Heminested Reverse Transcription-PCR Assay for Detection of Flaviviruses Targeted to a Conserved Region of the NS5 Gene Sequences," Journal of Clinical Microbiology, 2001, vol. 39 (5), pp. 1922-1927.

Schabereiter-Gurtner C., et al., "Application of Broad-Range 16s rRNA PCR Amplification and DGGE Fingerprinting for Detection of Tick-Infecting Bacteria," The Journal of Microbiological Methods, 2003, vol. 52 (2), pp. 251-260.

Scheffner M., et al., "The E6 Oncoprotein Encoded by Human Papillomavirus Types 16 and 18 Promotes the Degradation of p53," Cell, 1990, vol. 63 (6), pp. 1129-1136.

Schena M., et al., "Genome Analysis with Gene Expression Microarrays," Bioessays, 1996, vol. 18 (5), pp. 427-431.

Scheuermann R.H., et al., "Polymerase Chain-Reaction-Based mRNA Quantification Using an Internal Standard: Analysis of Oncogene Expression," Methods in Enzymology, 1993, vol. 218, pp. 446-473.

Schlecht N.F., et al., "Viral Load as a Predictor of the Risk of Cervical Intraepithelial Neoplasia," British Journal of Cancer, 2003, vol. 103 (4), pp. 519-524.

Schmidt T.M., et al., "Analysis of a Marine Pikoplankton Community by 16s rRNA Gene Cloning and Sequencing," Journal of Bacteriology, 1991, vol. 173 (14), pp. 4371-4378.

Schmitz F.J., et al., "Development of a Multiplex-PCR for Direct Detection of the Genes for Enterotoxin B and C, and Toxic Shock Syndrome Toxin-1 in *Staphylococcus aureus* Isolates," Journal of Medical Microbiology, 1998, vol. 47 (4), pp. 335-340.

Schmitz F.J., et al., "Development of Resistance to Ciprofloxacin, Rifampin, and Mupirocin in Methicillin-Susceptible and -Resistant *Staphylococcus aureus* Isolates," Antimicrobial Agents and Chemotherapy, 2000, vol. 44 (11), pp. 3229-3231.

Schmitz F.J., et al., "Specific Information Concerning Taxonomy, Pathogenicity and Methicillin Esistance of Staphylococci Obtained by a Multiplex PCR," Journal of Medical Microbiology, 1997, vol. 46 (9), pp. 773-778.

Schram K.H., et al., "Mass Spectrometry of Nucleic Acid Components," Methods of Biochemical Analysis, 1990, vol. 34, pp. 203-280.

Schultz J.C., et al., "Polymerise Chain Reaction Products Analyzed by Charge Detection Mass Spectrometry," Rapid Communications in Mass Spectrometry, 1999, vol. 13 (1), pp. 15-20.

Schwartz M., et al., "Prenatal Diagnosis of Alpha-1-Antitrypsin Deficiency Using Polymerase Chainreaction (PCR). Comparison of Conventional RFLP Methods with PCR used in Combination with Allelespecific Oligonucleotides or RFLP Analysis," Clinical Genetics, 1989, vol. 36 (6), pp. 419-426.

Schweiger B., et al., "Application of a Fluorogenic PCR Assay for Typing and Subtyping of Influenza Viruses in Respiratory Samples," Journal of Clinical Microbiology, 2000, vol. 38 (4), pp. 1552-1558.

Sciacchitano C.J., "Analysis of Polymerase Chain Reaction-Amplified DNA Fragments of *Clostridium botulinum* Type E Neurotoxin Gene by High Performance Capillary Electrophoresis," Journal of Liquid Chromatography & Related Technologies, 1996, vol. 19 (13), pp. 2165-2178.
Scott-Taylor T.H., et al., "Conserved Sequences of the Adenovirus Genome for Detection of all Human Adenovirus Types by Hybridization," Journal of Clinical Microbiology, 1992, vol. 30 (7), pp. 1703-1710.
Seifarth W., et al., "Rapid Identification of All Known Retroviral Reverse Transcriptase Sequences with a Novel Versatile Detection Assay," AIDS Research and Human Retroviruses, 2000, vol. 16 (8), pp. 721-729.
Sellner L., et al., "A Single-Tube Nested RT-PCR for the Detection of Ross River Virus," Methods in Molecular Biology, 1998, vol. 92, pp. 145-152.
Sellner L.N., et al., "Sensitive Detection of Ross River Virus—A One-Tube Nested RT-PCR" Journal of Virological Methods, 1994, vol. 49 (1), pp. 47-58.
Senko M.W., et al., "Determination of Monoisotopic Masses and Ion Populations for Large Biomoleculesfrom Resolved Isotopic Distributions," Journal of the American Society for Mass Spectrometry, 1995, vol. 6, pp. 229-233.
Seshadri R., et al., "Differential Expression of Translational Elements by Life Cycle Variants of *Coxiella burnetii,*" Infection and Immunity, 1999, vol. 67 (11), pp. 6026-6033.
Shadan F.F., et al., "N-Butyrate, A Cell Cycle Blocker, Inhibits the Replication of Polymaviruses and Papillomaviruses but Not That of Adenoviruses and Herpesviruses," Journal of Virology, 1994, vol. 68 (8), pp. 4785-4796.
Shaver Y.J., et al., "Restriction Fragment Length Polymorphism of rRNA Operons for Discrimination and Intergenic Spacer Sequences for Cataloging of *Bacilus subtilis* Sub-Groups," Journal of Microbiological Methods, 2002, vol. 50 (2), pp. 215-223.
Shaver Y.J., et al., "Variation in 16s-23s rRNA Intergenic Spacer Regions Among *Bacilus subtilis* 168 Isolates," Molecular Microbiology, 2001, vol. 42 (1), pp. 101-109.
Shimaoka M., et al., "Detection of the Gene for Toxic Shock Syndrome Toxin 1 in *Siaphylococcusaureus* by Enzyme-Labelled Oligonucleotideprobes," Journal of Medical Microbiology, 1996, vol. 44 (3), pp. 215-218.
Shimaoka M., et al., "Development of Enzyme-Labeled Oligonucleotide Probe for Detection of MecA Gene in Methicillin-Resistant *Staphylococcus aureus,*" Journal of Clinical Microbiology, 1994, vol. 32 (8), pp. 1866-1869.
Shrestha N.K., et al., "Rapid Identification of *Staphylococcus aureus* and the MecA Gene from BacT/ALERT Blood Culture Bottles by Using the Lightcycler System," Journal of Clinical Microbiology, 2002, vol. 40 (7), pp. 2659-2661.
Simonsen L., et al., "The Impact of Influenza Epidemics on Hospitalizations," Journal of Infectious Diseases, 2000, vol. 181 (3), pp. 831-837.
Skov R.L., et al., "Evaluation of a New 3-h Hybridization Method for Detecting the MecA Gene in *Staphylococcus aureus* and Comparison with Existing Genotypic and Phenotypic Susceptibility Testing Methods," Journal of Antimicrobial Chemotherapy, 1999, vol. 43 (4), pp. 467-475.
Smirnov I.P., et al., "Application of DNA-Binding Polymers for Preparation of DNA for Analysis by Matrix-Assisted Laser Desorption/Ionization Mass Spectrometry," Rapid Communications in Mass Spectrometry, 2001, vol. 15 (16), pp. 1427-1432.
Smith T.F., et al., "Comparison of Biosequences," Advances in Applied Mathematics, 1981, vol. 2, pp. 482-489.
Song F., et al., "Identification of cry11-type Genes from *Bacilus Thuringiensis* Strains and Characterization of a Novel Cry11-Type Gene," Applied and Environmental Microbiology, 2003, vol. 69, pp. 5207-5211.
Spackman E., et al., "Development of a Real-Time Reverse Transcriptase PCR Assay for Type A Influenzavirus and The Avian

(56) References Cited

OTHER PUBLICATIONS

H5 and H7 Hemagglutinin Subtypes," Journal of Clinical Microbiology, 2002, vol. 40 (9), pp. 3256-3260.
Spiess L., et al., "Trehalose is a Potent PCR Enhancer: Lowering of DNA Melting Temperature and Thermal Stabilization of Taq Polymerase by the Disaccharide Trehalose," Clinical Chemistry, 2004, vol. 50 (7), pp. 1256-1259.
Srinivasan J.R., et al., "Matrix-Assisted Laser Desorption/Ionization Time-of-Flight Mass Spectrometry as a Rapid Screening Method to Detect Mutations Causing Tay-Sachs Disease," Rapid Communications in Mass Spectrometry, 1997, vol. 11 (10), pp. 1144-1150.
Steffens D.L., et al., "Sequence Analysis of Mitochondrial DNA Hypervariable Regions Using Infrared Fluorescence Detection," BioTechniques, 1998, vol. 24 (6), pp. 1044-1046.
Stephensen C.B., et al., "Phylogenetic Analysis of a Highly Conserved Region of the Poymerase Gene from 11 Coronaviruses and Development of a Consensus Poymerase Chain Reaction Assay," Virus Research, 1999, vol. 60 (2), pp. 181-189.
Stone B., et al., "Rapid Detection and Simultaneous Subtype Differentiation of Influenza A Viruses by Real Time PCR," Journal of Virological Methods, 2004, vol. 117 (2), pp. 103-112.
Stoneking M., et al., "Population Variation of Human mtDNA Control Region Sequences Detected by Enzymatic Amplification and Sequence-Specific Oligonucleotide Probes," American Journal of Human Genetics, 1991, vol. 48 (2), pp. 370-382.
Stratagene Catalog, Gene Characterization Kits, 1988, pp. 39.
Strommenger B., et al., "Multiplex PCR Assay for Simultaneous Detection of Nine Clinically Relevant Antibiotic Resistance Genes in *Staphylococcus aureus*," Journal of Clinical Microbiology, 2003, vol. 41 (9), pp. 4089-4094.
Studdert M.J., et al., "Polymerase Chain Reaction Tests for the Identification of Ross River, Kunjin and Murray Valley Encephalitis Virus Infections in Horses," Australian Veterinary Journal, 2003, vol. 81 (1-2), pp. 76-80.
Stuhlmeier R., et al., "Fast, Simultaneous, and Sensitive Detection of Staphylococci," Journal of Clinical Pathology, 2003, vol. 56 (10), pp. 782-785.
Sumner J.W., et al., "PCR Amplification and Comparison of Nucleotide Sequences from the groESL Heat Shock Operon of *Ehrlichia* Species," Journal of Critical Microbiology, 1997, vol. 35.(8), pp. 2087-2092.
Sundsfjord A., et al., "Genetic Methods for Detection of Antimicrobial Resistance," APMIS : Acta Pathologica, Microbiologica, et Immunologica Scandinavica, 2004, vol. 112 (11-12), pp. 815-837.
Supplementary European Search Report for Application No. 04775904.8, mailed on Jul. 7, 2008, 8 pages.
Supplementary European Search Report for Application No. EP03796752.8, mailed on Aug. 7, 2007, 3 pages.
Supplementary European Search Report for Application No. EP03810055.8, mailed on Jun. 8, 2007, 4 pages.
Supplementary European Search Report for Application No. EP03814656, mailed on Oct. 16, 2007, 2 pages.
Supplementary European Search Report for Application No. EP04752257.8, mailed on Feb. 15, 2006, 2 pages.
Supplementary European Search Report for Application No. EP05753037, mailed on Aug. 21, 2009, 2 pages.
Supplementary Partial European Search Report for Application No. EP02709785.6, mailed Sep. 1, 2005, 5 pages.
Supplementary Partial European Search Report for Application No. EP05751872.2, mailed on Jan. 28, 2008, 8 pages.
Supplementary Partial European Search Report for Application No. EP05856582.1, mailed on Oct. 27, 2008, 10 pages.
Swaminathan B., et al., "PulseNet: The Molecular Subtyping Network for Foodborne Bacterial Disease Surveillance, United States," Emerging Infectious Diseases, 2001, vol. 7 (3), pp. 382-389.
Swanborg R.H., et al., "Human Herpesvirus 6 and Chlamydia Pneumoniae as Etiologic Agents in Multiplesclerosis—a Critical Review," Microbes and Infection / Institut Pasteur, 2002, vol. 4 (13), pp. 1327-1333.
Swenson J.M., et al., "Performance of Eight Methods, Including Two New Rapid Methods, for Detection of Oxacillin Resistance in a Challenge Set of *Staphylococcus aureus* Organisms," Journal of Clinical Microbiology, 2001, vol. 39 (10), pp. 3785-3788.
Takagaki Y., et al., "Four Factors are Required for 3"-End Cleavage of Pre-mRNAs," Genes and Development, 1989, vol. 3 (11), pp. 1711-1724.
Takahashi H., et al., "Characterization of gryA, gryB, grlA and grlB Mutations in Fluoroquinolone- Resistant Clinical Isolates of *Staphylococcus aureus*," The Journal of Antimicrobial Chemotherapy, 1998, vol. 41 (1), pp. 49-57.
Takahata M., et al., "Mutations in the GyrA and Gr1A Genes of Quinolone-Resistant Clinical Isolates of Methicillin-Resistant Staphylococcus Aureus," The Journal of Antimicrobial Chemotherapy, 1996, vol. 38 (3), pp. 543-546.
Takayama R., et al., "Quantification of Adenovirus Species B and C Viremia by Real-Time PCR in Adults and Children Undergoing Stem Cell Transplantation," Journal of Medical Virology, 2007, vol. 79 (3), pp. 278-284.
Takeuchi S., et al., "Serotyping of Adenoviruses on Conjunctival Scrapings by PCR and Sequence Analysis," Journal of Clinical Microbiology, 1999, vol. 37 (6), pp. 1839-1845.
Talaat A.M., et al., "Genome-Directed Primers for Selective Labeling of Bacterial Transcripts for DNA Microarray Analysis," Nature Biotechnology, 2000, vol. 18 (6), pp. 679-682.
Tan T.Y., "Use of Molecular Techniques for the Detection of Antibiotic Resistance in Bacteria," Expert Review of Molecular Diagnostics, 2003, vol. 3 (1), pp. 93-103.
Tanabe F., et al., "The Properties and Mec A Gene of the Methicillin-Resistant *Staphylococcus aureus* Isolated in Fukushima Medical College Hospital," Fukushima Journal of Medical.Science, 1993, vol. 39 (1), pp. 35-42.
Tang K., et al., "Detection of 500-Nucleotide DNA by Laser Desorption Mass Spectrometry," Rapid Communications in Mass Spectrometry, 1994, vol. 8 (9), pp. 727-730.
Tang K., et al., Double-Stranded DNA Analysis by Matrix Assisted Laser Desorption/Ionization, 42nd ASMS Conference on Mass Spectrometry, 1994.
Tang K., et al., "Matrix-Assisted Laser Desorption/Ionization of Restriction Enzyme-Digested DNA," Rapid Communications in Mass Spectrometry, 1994, vol. 8 (2), pp. 183-186.
Tang K., et al., Matrix-Assisted Laser Desorption/Ionization Mass Spectrometry of Oligonucleotides, Dissertation submitted to the Faculty of Vanderbilt University, 1994.
Tarassishin L., et al., "Adenovirus Core Protein VII Displays a Linear Epitope Conserved in a Linear Epitope Conserved in a Range of Human Adenoviruses," Journal of General Virology, 1999, vol. 80 (Pt 1), pp. 47-50.
Tarassishin L., et al., "An Epitope on the Adenovirus Fibre Tail is Common to all Human Subgroups," Archives of Virology, 2000, vol. 145 (4), pp. 805-811.
Tatuch Y., et al., "Heteroplasmic mtDNA Mutation (T-G) at 8993 Can Cause Leigh Disease When the Percentage of Abnormal mtDNA is High," The American Journal of Human Genetics, 1992, vol. 50 (4), pp. 852-858.
Taubenberger J.K., et al., "Characterization of the 1918 Influenza Virus Polymerase Genes," Nature, 2005, vol. 437 (7060), pp. 889-893.
Taylor L.H., et al., "Risk Factors for Human Disease Emergence," Philosophical Transactions of the Royal Society of London Series B, Biological Sciences, 2001, vol. 356 (1411), pp. 983-989.
Tenover F.C., et al., "Characterization of a Strain of Community-Associated Methicillin-Resistant*Slaphylococcus aureus* Widely Disseminated in the United States," Journal of Clinical Microbiology, 2006, vol. 44 (1), pp. 108-118.
Teramura T., et al., "Quantitative Detection of Serum Adenovirus in a Transplant Recipient," Lancet, 2002, vol. 359 (9321), pp. 1945.
Thiel V., et al., "Infectious RNA Transcribed in Vitro from a cDNA the Human Coronavirus Genome Cloned in Vaccinia Virus," The Journal of General Virology, 2001, vol. 82 (Pt 6), pp. 1273-1281.
Thompson J.D., et al., "Clustal W: Improving the Sensitivity of Progressive Multiple Sequence Alignmen Through Sequence

(56) References Cited

OTHER PUBLICATIONS

Weighting, Position-Specific Gap Penalties and Weight Matrix Choice," Nucleic Acids Research, 1994, vol. 22 (22), pp. 4673-4680.
Thompson W.W., et al., "Influenza-Associated Hospitalizations in the United States," The Journal of the American Medical Association, 2004, vol. 292 (11), pp. 1333-1340.
Tokue Y., et al., "Comparison of a Polymerase Chain Reaction Assay and a Conventional Microbiologic Method for Detection of Methicillin-Resistant *Slaphylococcus aureus*," Antimicrobial Agents and Chemotherapy, 1992, vol. 36 (1), pp. 6-9.
Tong J., et al., "Ligation Reaction Specificities of an NAD+-Dependent DNA Ligase from the Hyperthermophile Aquifex Aeolicus," Nucleic Acids Research, 2000, vol. 28 (6), pp. 1447-1454.
Top F.H Jr., "Control of Adenovirus Acute Respiratory Disease in U.S. Army Trainees," The Yale Journal of Biology and Medicine, 1975, vol. 48 (3), pp. 185-195.
Torroni A., et al., "Classification of European mtDNAs from an Analysis of Three European Populations," Genetics, 1996, vol. 144 (4), pp. 1835-1850.
Towner K.J., et al., "Development and Evaluation of a PCR-Based Immunoassay for the Rapid Detection of Methicillin-Resistant *Staphylococcus aureus*," Journal of Medical Microbiology, 1998, vol. 47 (7), pp. 607-613.
Tsuneyoshi T., et al., "Mass Spectrometric Gene Diagnosis of One-Base Substitution from Polymerase Chain Reaction Amplified Human DNA," Rapid Communications in Mass Spectometry, 1997, vol. 11 (7), pp. 719-722.
Tsunoda T., et al., "Time and Memory Efficient Algorithm for Extracting Palindromic and RepetitiveSubsequences in Nucleic Acid Sequences," Pacific Symposium on Biocomputing, 1999, vol. 4, pp. 202-213.
Udo E.E., et al., "A Chromosomal Location of the MupA Gene in *Staphylococcus aureus* Expressing High-Level Mupirocin Resistance," The Journal of Antimicrobial Chemotherapy, 2003, vol. 51 (5), pp. 1283-1286.
Udo E.E., et al., "Genetic Analysis of Methicillin-Resistant *Staphylococcus aureus* Expressing High-and Low-Level Mupirocin Resistance," Journal of Medical Microbiology, 2001, vol. 50 (10), pp. 909-915.
Udo E.E., et al., "Rapid Detection of Methicillin Resistance in Staphylococci Using a Slide Latex Agglutination Kit," International Journal of Antimicrobial Agents, 2000, vol. 15 (1), pp. 19-24.
Unal S., et al., "Detection of Methicillin-Resistant Staphylococci by Using the Polymerase Chain Reaction," Journal of Clinical Microbiology, 1992, vol. 30 (7), pp. 1685-1691.
Upton A., et al., "Mupirocin and *Staphylococcus aureus*: A Recent Paradigm of Emerging Antobiotic Resistance," The Journal of Antimicrobial Chemotherapy, 2003, vol. 51 (3), pp. 613-617.
Vabret A., et al., "Development of a PCR-and Hybridization-Based Assay (PCR Adenovirus Consensus) for the Detection and the Species Identification of Adenoviruses in Respiratory Specimens," Journal of Clinical Virology, 2004, vol. 31 (2), pp. 116-122.
Van Aerschot A., et al., "In Search of Acyclic Analogues as Universal Nucleosides in Degenerate Probes," Nucleosides and Nucleotides, 1995, vol. 14 (3-5), pp. 1053-1056.
Van Baar B.L., "Characterisation of Bacteria by Matrix-Assisted Laser Desorption/Ionisation and Electrospray Mass Spectrometry," FEMS Microbiology Reviews, 2000, vol. 24 (2), pp. 193-219.
Van Camp G., et al., "Amplification and Sequencing of Variable Regions in Bacterial 23s Ribosomal RNA Genes with Conserved Primer Sequences," Current Microbiology, 1993, vol. 27 (3), pp. 147-151.
Van Der Vossen J.M., et al., "DNA Based Typing Identification and Detection Systems for Food Spoilage Microorganisms: Development and Implementation," International Journal of Food Microbiology, 1996, vol. 33 (1), pp. 35-49.
Van Der Zee H., et al., "Rapid and Alternative Screening Methods for Microbiological Analysis," Journal of AOAC International, 1997, vol. 80 (4), pp. 934-940.
Van Dinten L.C., et al., "Proteolytic Processing of the Open Reading Frame lb-EncodedPart of Arterivirus Replicase Is Mediated by nsp4 Serine Protease and is Essential for Virus Replication," Journal of Virology, 1999, vol. 73 (3), pp. 2027-2037.
Van Elden L.J., et al., "Clinical Diagnosis of Influenza Virus Infection: Evaluation of Diagnostic Tools in General Practice," The British Journal of General Practice, 2001, vol. 51 (469), pp. 630-634.
Van Elden L.J., et al., "Simultaneous Detection of Influenza Viruses A and B Using Real-Time Quantitative PCR," Journal of Clinical Microbiology, 2001, vol. 39 (1), pp. 196-200.
Van Ert M.N., et al., "Mass Spectrometry Provides Accurate Characterization of Two Genetic Marker Types in Bacillus Anthracis," Bio Techniques, 2004, vol. 37 (4), pp. 642-651.
Van Leeuwen W.B., et al., "Multilocus Sequence Typing of *Staphylococcus aureus* with DNA Array Technology," Journal of Clinical Microbiology, 2003, vol. 41 (7), pp. 3323-3326.
Van Leeuwen W.B., et al., "Rapid Detection of Methicillin-Resistance in *Staphylococcus aureus* Isolates by the MRSA-Screen Latex Agglutination Test," Journal of Clinical Microbiology, 1999, vol. 37 (9), pp. 3029-3030.
Vanchiere J.A., et al., "Detection of BK Virus and Simian Virus 40 in the Urine of Healthy Children," Journal of Medical Virology, 2005, vol. 75 (3), pp. 447-454.
Vanderhallen H., et al., "Identification of Encephalomyocarditis Virus in Clinical Samples by ReverseTranscription-PCR Followed by Genetic Typing Using Sequence Analysis," Journal of Clinical Microbiology, 1998, vol. 36 (12), pp. 3463-3467.
Vannuffel P., et al., "Specific Detection of Methicillin-Resistant *Staphylococcus* Species by Multiplex PCR," Journal of Clinical Microbiology, 1995, vol. 33 (11), pp. 2864-2867.
Vannuffel P., et al., "Rapid and Specific Molecular Identification of Methicillin-Resistant *Staphylococcus aureus* in Endotracheal Aspirates from Mechanically Ventilated Patients," Journal of Clinical Microbiology, 1998, vol. 36 (8), pp. 2366-2368.
Verma S., et al., "Modified Oligonucleotides: Synthesis and Strategy for Users," Annual Review of Biochemistry, 1998, vol. 67, pp. 99-134.
Videla C., et al., "Genomic Analysis of Adenovirus Isolated from Argentinian Children with Acute Lower Respiratory Infections," Journal of Clinical Virology, 1999, vol. 14 (1), pp. 67-71.
Vilchez R.A. et al., "Detection of Polyomavirus Simian Virus 40 Tumor Antigen DNA in AIDS-Related Systemic Non-Hodgkin Lymphoma," Journal of Acquired Immune Deficiency Syndromes, 2002, vol. 29 (2), pp. 109-116.
Voelter C., et al., "Screening Human Tumor Samples with a Broad-Spectrum Polymerase Chain Reaction Method for the Detection of Polyomaviruses," Virology, 1997, vol. 237 (2), pp. 389-396.
Volokhov D., et al., "Microarray Analysis of Erythromycin Resistance Determinants," Journal of Applied Microbiology, 2003, vol. 95 (4), pp. 787-798.
Von Eiff C., et al., "Pathogenesis of Infections Due to Coagulase-Negative Staphylococci," The Lancet Infectious Diseases, 2002, vol. 2 (11), pp. 677-685.
Von Wintzingerode F., et al., "Base-Specific Fragmentation of Amplified 16S rRNA Genes Analyzed by Mass Spectrometry: A Tool for Rapid Bacterial Identification," Proceedings of the National Academy of Sciences, 2002, vol. 99 (10), pp. 7039-7044.
Walker E.S., et al., "A Decline in Mupirocin Resistance in Methicillin-Resistant *Staphylococcus aureus* Accompanied Administrative Control of Prescriptions," Journal of Clinical Microbiology, 2004, vol. 42 (6), pp. 2792-2795.
Wallace S.S., et al., "The Enigma of Endonuclease VIII," DNA Repair, 2003, vol. 2 (5), pp. 441-453.
Wallet F., et al., "Choice of a Routine Method for Detecting Methicillin-Resistance in Staphylococci," The Journal of Antimicrobial Chemotherapy, 1996, vol. 37 (5), pp. 901-909.
Walters J.J., et al., "Genotyping Single Nucleotide Polymorphisms Using Intact Polymerase Chain Reaction Products by Electrospray Quadrupole Mass Spectrometry," Rapid Communications in Mass Spectrometry, 2001, vol. 15 (18), pp. 1752-1759.
Wang G., et al., "Targeted Mutagenesis in Mammalian Cells Mediated by Intracellular Triple Helix Formation," Molecular and Cellular Biology, 1995, vol. 15 (3), pp. 1759-1768.

(56) References Cited

OTHER PUBLICATIONS

Ward C.L., et al., "Design and Performance Testing of Quantitative Real Time PCR Assays for Influenza A and B Viral Load Measurement," Journal of Clinical Virology, 2004, vol. 29 (3), pp. 179-188.
Watanabe K., et al., "ICB Database: The gyrB Database for Identification and Classification of Bacteria," Nucleic Acids Research, 2001, vol. 29 (1), pp. 344-345.
Weissenbacher M., et al., "Etiologic and Clinical Evaluation of Acute Lower Respiratory TractInfections in Young Argentinean Children: An Overview," Reviews of Infectious Diseases, 1990, vol. 12 (Suppl 8), pp. S889-S898.
Welham K.J., et al., "The Characterization of Micro-Organisms by Matrix-Assisted Laser Desorption/Lonization Time-of-Flight Mass Spectrometry," Rapid Communications in Mass Spectrometry, 1998, vol. 12 (4), pp. 176-180.
Wertheim H.F., et al., "Effect of Mupirocin Treatment on Nasal, Pharyngeal, and Perineal Carriage of *Staphylococcus aureus* in Healthy Adults," Antimicrobial Agents and Chemotherapy, 2005, vol. 49 (4), pp. 1465-1467.
Westermann P., et al., "Inhibition of Expression of SV40 Virus Large T-Antigen by Antisense Oligodeoxyribonucleotides," Biomedica Biochimica Acta, 1989, vol. 1, pp. 85-93.
Whiley D.M., et al., "Simultaneous Detection and Differentiation of Human Polyomaviruses JC and BK by a Rapid and Sensitive PCR-ELAHA Assay and a Survey of the JCV Subtypes within an Australian Population," Journal of Medical Virology, 2004, vol. 72 (3), pp. 467-472.
Wichelhaus T.A., et al., "Rapid Detection of Epidemic Strains of Methicillin-Resistant*Staphylococcus aureus*," Journal of Clinical Microbiology, 1999, vol. 37 (3), pp. 690-693.
Wickham T.J., "Targeting Adenovirus," Gene Therapy, 2000, vol. 7 (2), pp. 110-114.
Widjojoatmodjo M.N., et al., "Rapid Identification of Bacterial by PCR-Single-Strand Conformation Polymorphism," Journal of Clinical Microbiology, 1994, vol. 32 (12), pp. 3002-3007.
Widjojoatmodjo M.N., et al., "The Magnetic Immuno Polymerase Chain Reaction Assay for Direct Detection of *Salmonellae* in Fecal Samples," Journal of Clinical Microbiology, 1992, vol. 30 (12), pp. 3195-3199.
Winger B.E., et al., "High Resolution Accurate Mass Measurements of Biomolecules using a new Electrospray Ionization Ion Cyclotron Resonance Mass Spectrometer," Journal American Society for Mass Spectrometry, 1993, vol. 4 (7), pp. 566-577.
Wolter A., et al., "Negative Ion FAB Mass Spectrometric Analysis of Non-Charged Key Intermediates in Oligonucleotide Synthesis: Rapid Identification of Partially Protected Dinucleoside Monophosphates," Biomedical and Environmental Mass Spectrometry, 1987, vol. 14, pp. 111-116.
Woo T.H., et al., "Identification of Leptospira Inadai by Continuous Monitoring of Fluorescence during Rapid Cycle PCR," Systematic and Applied Microbiology, 1998, vol. 21 (1), pp. 89-96.
Wood S.R., et al., "Rapid Detection and Seotyping of Adenovirus by Direct Immunofluorescence," Journal of Medical Virology, 1997, vol. 51 (3), pp. 198-201.
Wright K.E., et al., "Typing and Subtyping of Influenza Viruses in Clinical Samples by PCR," Journal of Clinical Microbiology, 1995, vol. 33 (5), pp. 1180-1184.
Written Opinion for Application No. PCT/US2004/33742, mailed on May 15, 2006, 5 pages.
Wu S., et al., "Genetic Organization of the mecA Region in Methicillin-Susceptible and Methicillin-Resistant Strains *Staphylococcus sciuri*," The Journal of Bacteriology, 1998, vol. 180 (2), pp. 236-242.
Wu X., et al., "Establishment of a Fluorescent Polymerase Chain Reaction Method for the Detection of SARS-Associated Coronavhus and its Clinical Application," Chinese Medical Journal, 2003, vol. 116 (7), pp. 988-990.
Wunschel D., et al., "Discrimination Among the *B. cereus* Group, in Comparison to *B. subtilis*, by Structural Carbohydrate Profiles and Ribosomal RNA Spacer Region PCR," Systematic and Applied Microbiology, 1994, vol. 17, pp. 625-635.
Wunschel D.S., et al., "Analysis of Double-Stranded Polymerase Chain Reaction Products from the *Bacilus cereus* Group by Electrospray Lonization Fourier Transform Lon Cyclotron Resonance Mass Spectrometry," Rapid Communications in Mass Spectrometry, 1996, vol. 10 (1), pp. 29-35.
Wunschel D.S., et al., "Heterogeneity in *Bacillus cereus* PCR Products Detected by ESI-FTICR Mass Spectrometry," Analytical Chemistry, 1998, vol. 70 (6), pp. 1203-1207.
Wunschel D.S., et al., "Mass spectrometric characterization of DNA for molecular biological applications: advances using MALDI and ESI," Advances in Mass Spectrometry, 1998, vol. 14, Elsevier, pp. 377-406.
Xu L., et al., "Electrophore Mass Tag Dideoxy DNA Sequencing," Analytical Chemistry, 1997, vol. 69 (17), pp. 3595-3602.
Xu W., et al., "Species-Specific Identification of Human Adenoviruses by a Multiplex PCR Assay," Journal of Clinical Microbiology, 2000, vol. 38 (11), pp. 4114-4120.
Xu W., et al., "Type-Specific Identification of Human Adenovirus, 3, 7, and 21 by a Multiplex PCR Assay," Journal of Medical Virology, 2001, vol. 64 (4), pp. 537-542.
Xu X., et al., "Intercontinental Circulation of Human Influenza A(H1N2) Reassortant Viruses During the 2001-2002 Influenza Season," The Journal of Infectious Diseases, 2002, vol. 186 (10), pp. 1490-1493.
Yao Z.P., et al., "Mass Spectrometry Based Proteolytic Mapping for Rapid Virus Identification," Analytical Chemistry, 2002, vol. 74 (11), pp. 2529-2534.
Yasui T., et al., "A Specific Oligonucleotide Primer for the Rapid Detection of *Lactobacillus* Lindneri by Polymerase Chain Reaction," Canadian Journal of Microbiology, 1997, vol. 43 (2), pp. 157-163.
Ye K., et al., "Three Distinct Promoters Direct Transcription of Different 5" Untranslated Regions of the Human Interleukin 1 Type 1 Receptor. A Possible Mechanism for Control of Translation," Cytokine, 1996, vol. 8 (6), pp. 421-429.
Yun H.J., et al., "Increased Antibacterial Activity of OW286, a Novel Fluoronaphthyridone Antibiotic, Against *Staphylococcus aureus* Strains with Defined Mutations in DNA Gyrase and Toposiomerase IV," International Journal of Antimicrobial Agents, 2005, vol. 25 (4), pp. 334-337.
Zeng Z.B., "Precision Mapping of Quantitative Trait Loci," Genetics, 1994, vol. 136 (4), pp. 1457-1468.
Zhang J., et al., "PowerBLAST: A New Network BLAST Application for Interactive or Automated Sequence Analysis and Annotation," Genome Research, 1997, vol. 7 (6), pp. 649-656.
Zhang K., et al., "New Quadriplex PCR Assay for Detection of Methicillin and Mupirocin Resistance and Simultaneous Discrimination of *Staphylococcus* from Coagulase-Negative Staphylococci," Journal of Clinical Microbiology, 2004, vol. 42 (11), pp. 4947-4955.
Zhang W.D., et al., "Detection and Identification of Human Influenza Viruses by the Polymerase Chain Reaction," Journal of Virological Methods, 1991, vol. 33 (1-2), pp. 165-189.
Zhang Y.Q., et al., "Genome-Based Analysis of Virulence Genes in a Non-Biofilm-Forming *Staphylococcus epidemidis* Strain (ATCC 12228)," Molecular Microbiology, 2003, vol. 49 (6), pp. 1577-1593.

US 9,023,655 B2

SAMPLE PROCESSING UNITS, SYSTEMS, AND RELATED METHODS

The present application is a continuation of U.S. patent application Ser. No. 13/595,189 filed Aug. 27, 2012, now U.S. Pat. No. 8,609,430, issued Dec. 17, 2013, which is a continuation of U.S. patent application Ser. No. 13/221,608 filed Aug. 30, 2011, now U.S. Pat. No. 8,252,599, issued Aug. 28, 2012, which is a continuation of U.S. patent application Ser. No. 12/561,175 filed Sep. 16, 2009, now U.S. Pat. No. 8,148,163, issued Apr. 3, 2012, which claims priority to U.S. Provisional Application Ser. No. 61/097,525 filed Sep. 16, 2008, each of which is herein incorporated by reference in its entirety.

FIELD OF THE INVENTION

The invention relates generally to sample purification, and provides sample processing units, systems, and methods useful for this purpose.

BACKGROUND OF THE INVENTION

Nucleic acid amplification techniques, such as the polymerase chain reaction (PCR) have widespread applications in many scientific disciplines, including microbiology, medical research, forensic analysis, and clinical diagnostics. In some of these applications, PCR products are "sized" using traditional biochemical techniques such as standard gel electrophoresis involving either intercalating dyes or fluorescently labeled primers. Other applications, such as 5'-nuclease or TaqMan® probe-based assays, which are widely used in a number of PCR-related diagnostic kits, confirm the presence (or absence) of a specific PCR product, but provide no direct information on the size of the particular amplicon. These methods typically have limited utility for relatively small amplicons (less than 150 base pairs), owing to the proportionately high fluorescence background, and do not provide any information with respect to amplicon heterogeneity or exact length.

Electrospray ionization mass spectrometry (ESI-MS) has become an important technique for the analysis of biopolymers, including nucleic acids. Compared to the more traditional nucleic acid analysis methods mentioned above, ESI-MS as a platform on which to characterize PCR products typically provides improved speed, sensitivity, and mass accuracy, among other attributes. Further, since the exact mass of each nucleotide or nucleobase is known with great accuracy, a high-precision mass measurement obtained via mass spectrometry can be used to derive a base composition within the experimentally obtained mass measurement uncertainty. In certain applications, the base compositions of PCR products are used to identify unknown bioagents, genotype nucleic acids, and provide drug resistance profiles as well as other information about the corresponding template nucleic acids or source organisms.

In the electrospray ionization process, large charged droplets are produced in the process of "pneumatic nebulization" where the analyte solution is forced through a needle at the end of which is applied a potential sufficient to disperse the emerging solution into a very fine spray of charged droplets all of which have the same polarity. The solvent evaporates, shrinking the droplet size and increasing the charge concentration at the droplet's surface. Eventually, at the Rayleigh limit, Coulombic repulsion overcomes the droplet's surface tension and the droplet explodes. This "Coulombic explosion" forms a series of smaller, lower charged droplets. The process of shrinking followed by explosion is repeated until individually charged analyte ions are formed. The charges are statistically distributed amongst the analyte's available charge sites, leading to the possible formation of multiply charged ions. Increasing the rate of solvent evaporation, by introducing a drying gas flow counter current to the sprayed ions, increases the extent of multiple-charging. Decreasing the capillary diameter and lowering the analyte solution flow rate, e.g., in nanospray ionization, typically creates ions with higher mass-to-charge (m/z) ratios (i.e., it is a softer ionization technique) than those produced by "conventional" ESI and are commonly used in the field of bioanalysis.

ESI generally requires relatively clean samples and is intolerable of cationic salts, detergents, and many buffering agents commonly used in biochemical laboratories. Buffer systems commonly employed in polymerase chain reactions, for example, typically include electrospray incompatible reagents such as KCl, $MgCl_2$, Tris-HCl, and each of the four deoxynucleotide triphosphates (dNTPs). Even the presence of relatively low concentrations of metal cations (e.g., less than 100 µM) can reduce MS sensitivity for oligonucleotides as the signal for each molecular ion is spread out over multiple salt adducts. Thus, in addition to removing detergents and dNTPs, effective ESI-MS of PCR products typically requires that the salt concentration be reduced by more than a factor of 1000 prior to analysis.

Ethanol precipitation has been used to desalt PCR products for subsequent MS analysis as short oligonucleotides and salts are removed while the sample is concentrated. In some of these methods, the PCR product can be precipitated from concentrated ammonium acetate solutions, either overnight at 5° C. or over the course of 10-15 minutes with cold (−20° C.) ethanol. Unfortunately, a precipitation step alone is generally insufficient to obtain PCR products which are adequately desalted to obtain high-quality ESI spectra; consequently, precipitation is generally followed by a dialysis step to further desalt the sample. While several approaches have successfully employed these methods to characterize a number of PCR products, there remains a need to apply these and related methods in a robust and fully automated high-throughput manner.

SUMMARY OF THE INVENTION

The present invention provides sample processing units that are useful in various purification processes. In certain embodiments, for example, the sample processing units are used to perform solution capture methods of purifying nucleic acids, which are subsequently analyzed using any suitable approach, including electrospray mass spectrometric-based analysis. Some of these embodiments include adding an anion exchange resin to the solution and mixing these materials in a sample processing unit to yield a suspension of the anion exchange resin in the solution in which the nucleic acids bind to the anion exchange resin. Additional processing steps performed using the sample processing units described herein typically include isolating the anion exchange resin from the solution, washing the anion exchange resin to remove one or more contaminants with one or more wash buffers while retaining the nucleic acids bound to the resin, and eluting the nucleic acids from the anion exchange resin with an elution buffer, thereby yielding purified nucleic acids that are suitable for further analysis. In addition to sample processing units and stations, the invention also provides related systems and methods.

In one aspect, the invention provides a sample processing unit that includes at least one container (e.g., a cuvette or the like) configured to contain at least one sample comprising at least one magnetically responsive particle (e.g., a magnetically responsive bead coated with a selected capture reagent, etc.), and at least one magnet (e.g., a permanent magnet, an electromagnet, etc.) that generates, or is configured to generate, at least one magnetic field, which magnet is in a substantially fixed position relative to the container. The sample processing unit also includes at least one conveyance mechanism configured to convey the container between at least first and second positions in which at least the first position is within magnetic communication with the magnet when the magnet generates the magnetic field, and at least one rotational mechanism operably connected to the container, which rotational mechanism is configured to rotate the container when the container is in at least the second position. Typically, the sample processing unit includes at least one mounting bracket that is operably connected to one or more of: the container, the magnet, the conveyance mechanism, or the rotational mechanism. In some embodiments, a sample processing station includes the sample processing unit. In certain embodiments, a carrier mechanism includes the sample processing unit. In some of these embodiments, a system includes the carrier mechanism.

In some embodiments, the conveyance mechanism comprises at least one motor. The conveyance mechanism is configured to rotate the container between the first and second positions in certain embodiments. In other exemplary embodiments, the conveyance mechanism is configured to slide the container between the first and second positions. To further illustrate, in some embodiments, the conveyance mechanism comprises at least one support member operably connected to the container and/or to the rotational mechanism. In some of these embodiments, the support member is configured to slide between the first and second positions, whereas in other exemplary embodiments, the support member is configured to rotate between the first and second positions.

In certain embodiments, the rotational mechanism is configured to rotate the container in at least one pulsed mode, during which a substantial portion of the time of rotation, a rate of rotation of the container exceeds a rate of rotation of the sample when the container contains the sample such that the sample is sheared away from a surface of the container. In some embodiments, the rotational mechanism is configured to rotate the container in at least one oscillating motion.

In another aspect, the invention provides a sample processing unit that includes at least one cuvette configured to contain at least one sample comprising at least one magnetically responsive particle, and at least one magnet (e.g., a permanent magnet, an electromagnet, etc.) that generates, or is configured to generate, at least one magnetic field, which magnet is in a substantially fixed position. In some embodiments, two or more magnets are disposed proximal to a receiving space in which the cuvette is located at least partially within the receiving space when the cuvette is in the first position. The sample processing unit also includes at least a first motor operably connected to the cuvette. The first motor is configured to rotate the cuvette around a central longitudinal axis of the cuvette. In addition, the sample processing unit also includes at least one support member (e.g., a swing arm or the like) operably connected to the first motor, and at least a second motor operably connected to the support member. The second motor is configured to rotate the cuvette between at least first and second positions in which at least the first position is within magnetic communication with the magnet when the magnet generates the magnetic field. In certain embodiments, a sample processing station includes the sample processing unit. Optionally, a carrier mechanism (e.g., a carousel, a conveyor track, etc.) includes the sample processing unit. In some of these embodiments, a system includes the carrier mechanism.

In some embodiments, the first motor (e.g., a stepper motor, a servo motor, etc.) is configured to rotate the cuvette in at least one pulsed mode, during which a substantial portion of the time of rotation, a rate of rotation of the cuvette exceeds a rate of rotation of the sample when the cuvette contains the sample such that the sample is sheared away from a surface of the cuvette, e.g., to effect thorough mixing of the sample and other materials that may be present in the cuvette. To further illustrate, the first motor is optionally configured to rotate the cuvette in at least one oscillating motion. In certain embodiments, the second motor comprises a brushless direct current motor or the like. The sample processing unit generally includes circuitry configured to control the first and second motors.

In certain embodiments, the support member comprises a first end and a second end in which the cuvette is retained at or proximal to the first end of the support member, and in which the second motor is operably connected to the support member at or proximal to the second end of the support member. In some of these embodiments, the support member is configured to rotate at least partially around a rotational axis extending through the second end of the support member. As a further illustrate, in some embodiments, a pin is fixedly coupled to the second end of the support member and aligned with the rotational axis in which the pin is operably coupled to the second motor.

In some embodiments, the sample processing unit includes a mounting bracket in which the support member is operably connected to the mounting bracket. In certain of these embodiments, the magnet is operably connected to the mounting bracket.

In another aspect, the invention provides a sample processing system. The system includes at least one sample processing unit that comprises: at least one cuvette configured to contain at least one sample comprising at least one magnetically responsive particle; at least one magnet that generates, or is configured to generate, at least one magnetic field, which magnet is in a substantially fixed position; at least a first motor operably connected to the cuvette, which first motor is configured to rotate the cuvette around a central longitudinal axis of the cuvette; at least one support member operably connected to the first motor; and at least a second motor operably connected to the support member, which second motor is configured to rotate the cuvette between at least first and second positions in which at least the first position is within magnetic communication with the magnet when the magnet generates the magnetic field. The system also includes at least one carrier mechanism operably connected to the sample processing unit. The carrier mechanism is configured to move the sample processing unit to one or more locations. The system further includes at least one material transfer component configured to transfer material to and/or from the cuvette, and at least one controller operably connected to the sample processing unit, the carrier mechanism, and/or the material transfer component. The controller is configured to effect one or more of: the magnet to generate the magnetic field, the first motor to rotate the cuvette, the second motor to rotate the cuvette between the first and second positions, the carrier mechanism to move the sample processing unit to the one or more locations, or the material transfer component to transfer the material to and/or from the cuvette.

The carrier mechanism includes various embodiments. In one embodiment, for example, the carrier mechanism comprises a carousel that is configured to rotate the sample processing unit to the one or more locations. In another exemplary embodiment, the carrier mechanism comprises a conveyor track that is configured to convey the sample processing unit to the one or more locations. Typically, the carrier mechanism comprises a plurality of sample processing units. In some of these embodiments, the material transfer component comprises a manifold that is configured to transfer material to and/or from the cuvettes of at least two sample processing units substantially simultaneously.

In some embodiments, the material transfer component comprises one or more of: a sample input gantry head, a sample wash station, a sample output gantry head, or a cuvette wash station. Typically, the material transfer component is configured to transfer fluidic material. In certain embodiments, the material transfer component comprises one or more needles.

In certain embodiments, the controller is configured to effect the first motor to rotate the cuvette in one or more selectable modes. In some embodiments, for example, the controller is configured to effect the first motor to rotate the cuvette in at least one pulsed mode, during which a substantial portion of the time of rotation, a rate of rotation of the cuvette exceeds a rate of rotation of the sample when the cuvette contains the sample such that the sample is sheared away from a surface of the cuvette. In other exemplary embodiment, the controller is configured to effect the first motor to rotate the cuvette in at least one oscillating motion.

In some embodiments, the sample processing system includes at least one detector configured to detect one or more detectable signals of or from one or more sample components. In certain embodiments, the detector is within sensory communication with the cuvette when the carrier mechanism moves the sample processing unit to at least one of the locations. Optionally, the material transfer component is configured to transfer the material from the cuvette to the detector. In some embodiments, the controller is operably connected to the detector. In these embodiments, the controller is configured to effect the detector to detect the detectable signals of or from the sample components. To further illustrate, in certain embodiments, the detector comprises a mass spectrometer. In some of these embodiments, the mass spectrometer comprises an electrospray ionization time-of-flight mass spectrometer.

In another aspect, the invention relates to a method of processing a sample. The method includes (a) providing at least one sample processing unit that comprises: at least one cuvette that contains at least one sample comprising at least one magnetically responsive particle comprising at least one captured first component (e.g., a biopolymer, such as a polynucleotide, a polypeptide, or the like); at least one magnet that is in a substantially fixed position; at least a first motor operably connected to the cuvette, which first motor is configured to rotate the cuvette around a central longitudinal axis of the cuvette; at least one support member operably connected to the first motor; and at least a second motor operably connected to the support member, which second motor is configured to rotate the cuvette between at least first and second positions in which the magnet is capable of magnetically communicating with the cuvette when the cuvette is at least in the first position. The method also includes (b) moving the cuvette into the first position using the second motor such that a magnetic field generated by the magnet causes the magnetically responsive particle to move and/or be retained proximal to a surface of the cuvette. In addition, the method also includes (c) removing at least a second component from the cuvette to thereby process the sample. In some embodiments, the method includes adding the sample and/or the magnetically responsive particle to the cuvette prior to (a) when the cuvette is in the second position. Optionally, the method includes adding at least one wash reagent to the cuvette. In certain embodiments, the magnet comprises a permanent magnet. In other exemplary embodiments, the magnet comprises an electromagnet. In these embodiments, the method typically comprises generating the magnetic field prior to or during (b). Typically, a carrier mechanism comprises the sample processing unit and the method comprises moving the sample processing unit to one or more locations.

The magnetically responsive particle includes various embodiments. In some embodiments, for example, the magnetically responsive particle comprises an anion exchange resin. Typically, the magnetically responsive particle comprises at least one biopolymer capture reagent. In certain embodiments, the biopolymer capture reagent comprises at least one anion exchange functional group. The anion exchange functional group typically comprises a pKa value of 9.0 or greater. To further illustrate, exemplary anion exchange functional groups are selected from, e.g., a primary amine, a second amine, a tertiary amine, a quaternary amine, a polyethyleneimine, a charged aromatic amine, a diethylaminomethyl, a diethylaminoethyl.

The method typically includes rotating the cuvette using the first motor such that sample components mix with one another. In some embodiments, the method includes rotating the cuvette when the cuvette is in the second position. In certain embodiments, the method includes rotating the cuvette in at least one pulsed mode, during which a substantial portion of the time of rotation, a rate of rotation of the cuvette exceeds a rate of rotation of the sample such that the sample is sheared away from a surface of the cuvette. Optionally, the method includes rotating the cuvette in at least one oscillating motion.

In certain embodiments, the method includes detecting at least one detectable signal of or from the sample. For example, the method optionally includes detecting a molecular mass of the first component. In these embodiments, the molecular mass is generally detected using a mass spectrometer. In some of these embodiments, the first component comprises a nucleic acid and the method comprises correlating the molecular mass of the nucleic acid with a base composition and/or an identity of the nucleic acid.

BRIEF DESCRIPTION OF THE DRAWINGS

The description provided herein is better understood when read in conjunction with the accompanying drawings which are included by way of example and not by way of limitation. It will be understood that like reference numerals identify like components throughout the drawings, unless the context indicates otherwise. It will also be understood that some or all of the figures may be schematic representations for purposes of illustration and do not necessarily depict the actual relative sizes or locations of the elements shown.

DETAILED DESCRIPTION

A. Definitions

Figure 1A:
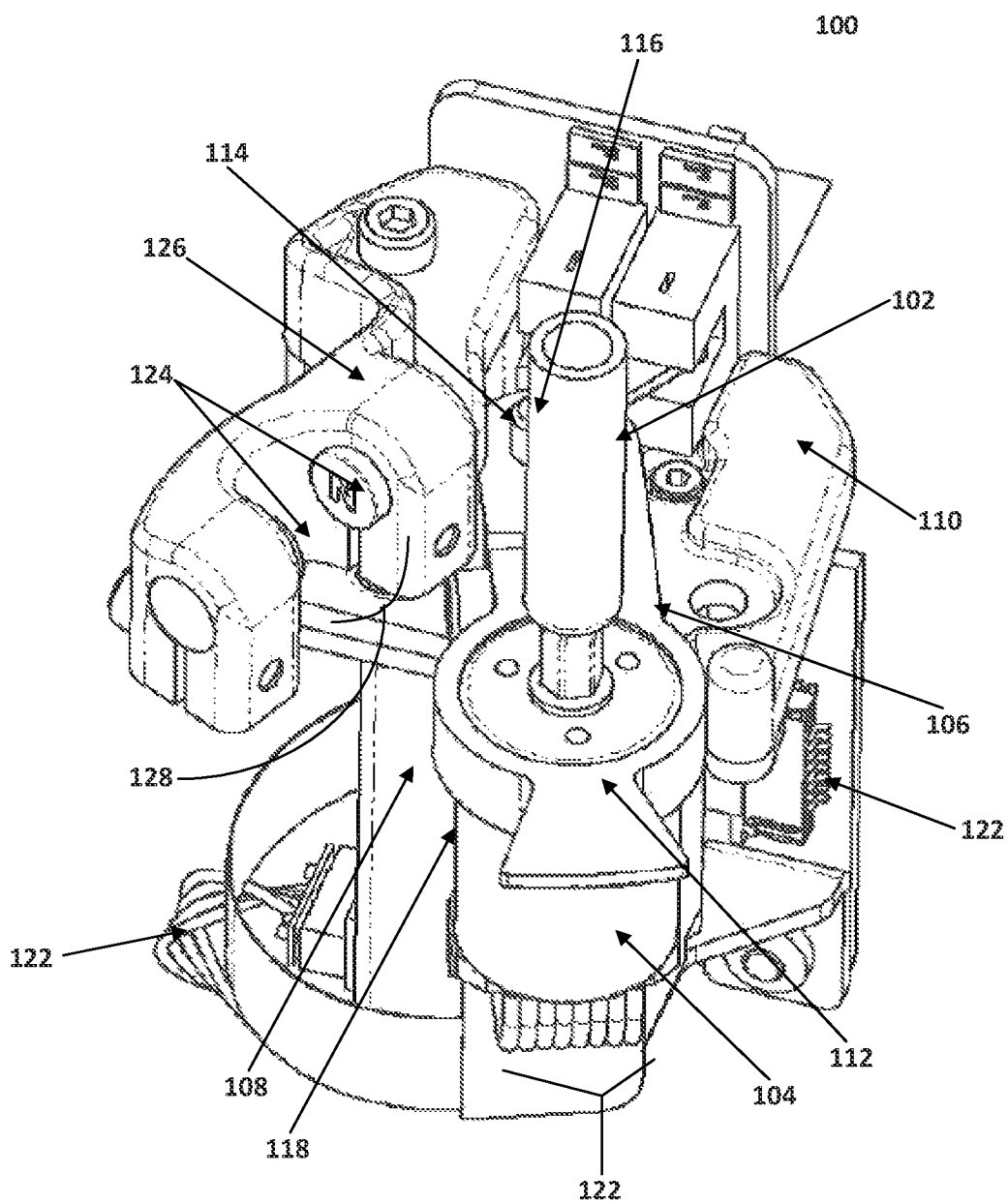
FIG. 1A schematically shows a sample processing unit with a cuvette in a second position from a perspective view according to one embodiment of the invention.
Figure 1B:
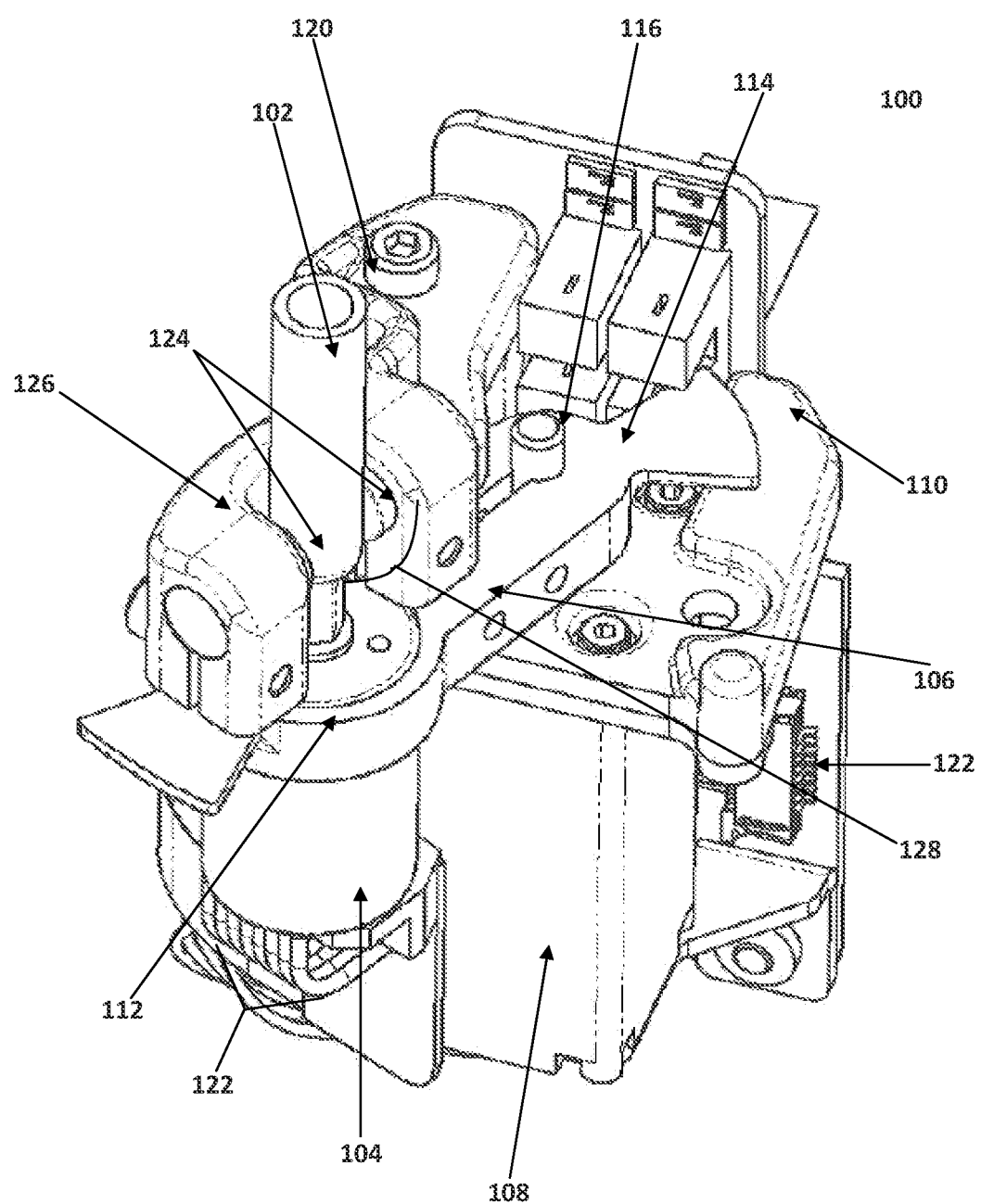
FIG. 1B schematically depicts the sample processing unit of FIG. 1A with the cuvette in a first position from a perspective view.
Figure 1C:
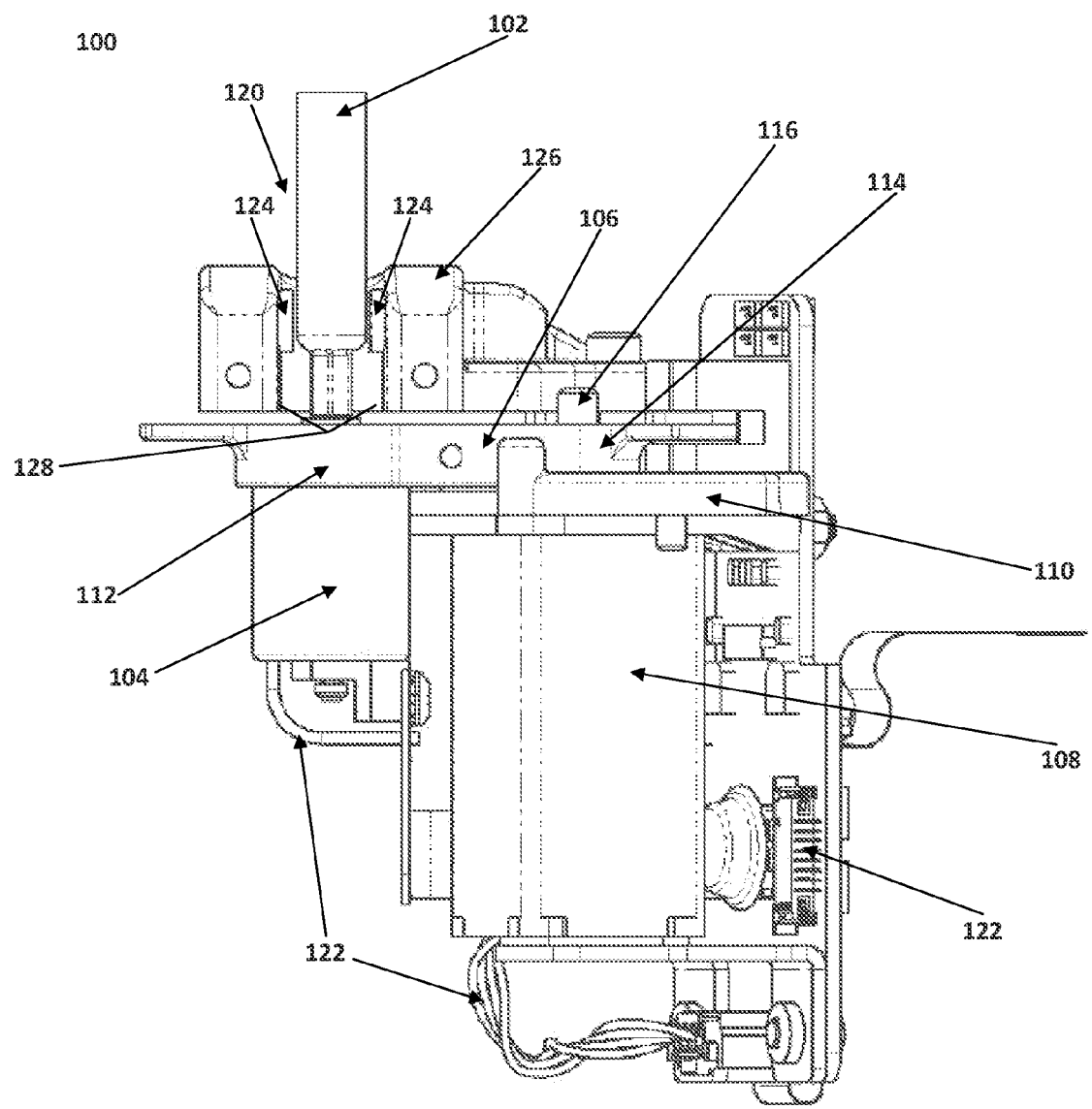
FIG. 1C schematically depicts the sample processing unit of FIG. 1A with the cuvette in a first position from a side elevation view.
Figure 1D:
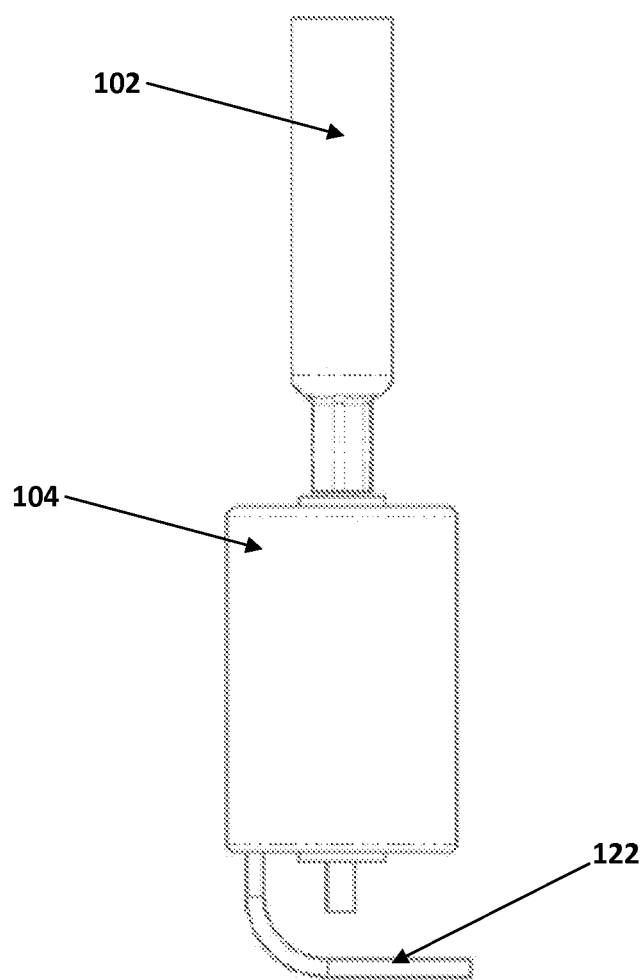
FIG. 1D schematically illustrates a detailed side elevation view of a motor operably connected to a cuvette of the sample processing unit of FIG. 1A.

Before describing the invention in detail, it is to be understood that this invention is not limited to particular sample processing units, systems, or methods, which can vary. As used in this specification and the appended claims, the singular forms "a," "an," and "the" also include plural referents unless the context clearly provides otherwise. Thus, for example, reference to "a sample processing unit" includes a combination of two or more sample processing units. It is also to be understood that the terminology used herein is for the purpose of describing particular embodiments only, and is not intended to be limiting. Further, unless defined otherwise, all technical and scientific terms used herein have the same meaning as commonly understood by one of ordinary skill in the art to which this invention pertains. In describing and claiming the invention, the following terminology, and grammatical variants thereof, will be used in accordance with the definitions set forth below.

The term "amplifying" or "amplification" in the context of nucleic acids refers to the production of multiple copies of a polynucleotide, or a portion of the polynucleotide, typically starting from a small amount of the polynucleotide (e.g., a single polynucleotide molecule), where the amplification products or amplicons are generally detectable. Amplification of polynucleotides encompasses a variety of chemical and enzymatic processes. The generation of multiple DNA copies from one or a few copies of a target or template DNA molecule during a polymerase chain reaction (PCR) or a ligase chain reaction (LCR) are forms of amplification. Amplification is not limited to the strict duplication of the starting molecule. For example, the generation of multiple cDNA molecules from a limited amount of RNA in a sample using reverse transcription (RT)-PCR is a form of amplification. Furthermore, the generation of multiple RNA molecules from a single DNA molecule during the process of transcription is also a form of amplification.

The term "base composition" refers to the number of each residue comprised in an amplicon or other nucleic acid, without consideration for the linear arrangement of these residues in the strand(s) of the amplicon. The amplicon residues comprise, adenosine (A), guanosine (G), cytidine, (C), (deoxy) thymidine (T), uracil (U), inosine (I), nitroindoles such as 5-nitroindole or 3-nitropyrrole, dP or dK (Hill F et al. (1998) "Polymerase recognition of synthetic oligodeoxyribonucleotides incorporating degenerate pyrimidine and purine bases" *Proc Natl Acad Sci U.S.A.* 95(8):4258-63), an acyclic nucleoside analog containing 5-nitroindazole (Van Aerschot et al., Nucleosides and Nucleotides, 1995, 14, 1053-1056), the purine analog 1-(2-deoxy-beta-D-ribofuranosyl)-imidazole-4-carboxamide, 2,6-diaminopurine, 5-propynyluracil, 5-propynylcytosine, phenoxazines, including G-clamp, 5-propynyl deoxy-cytidine, deoxy-thymidine nucleotides, 5-propynylcytidine, 5-propynyluridine and mass tag modified versions thereof, including 7-deaza-2'-deoxyadenosine-5'-triphosphate, 5-iodo-2'-deoxyuridine-5'-triphosphate, 5-bromo-2'-deoxyuridine-5'-triphosphate, 5-bromo-2'-deoxycytidine-5'-triphosphate, 5-iodo-2'-deoxycytidine-5'-triphosphate, 5-hydroxy-2'-deoxyuridine-5'-triphosphate, 4-thiothymidine-5'-triphosphate, 5-aza-2'-deoxyuridine-5'-triphosphate, 5-fluoro-2'-deoxyuridine-5'-triphosphate, $O^6$-methyl-2'-deoxyguanosine-5'-triphosphate, $N^2$-methyl-2'-deoxyguanosine-5'-triphosphate, 8-oxo-2'-deoxyguanosine-5'-triphosphate or thiothymidine-5'-triphosphate. In some embodiments, the mass-modified nucleobase comprises $^{15}N$ or $^{13}C$ or both $^{15}N$ and $^{13}C$. In some embodiments, the non-natural nucleosides used herein include 5-propynyluracil, 5-propynylcytosine and inosine. Herein the base composition for an unmodified DNA amplicon is notated as $A_wG_xC_yT_z$, wherein w, x, y and z are each independently a whole number representing the number of said nucleoside residues in an amplicon. Base compositions for amplicons comprising modified nucleosides are similarly notated to indicate the number of said natural and modified nucleosides in an amplicon. Base compositions are calculated from a molecular mass measurement of an amplicon, as described below. The calculated base composition for any given amplicon is then compared to a database of base compositions. A match between the calculated base composition and a single database entry reveals the identity of the bioagent.

The term "biopolymer" refers a biomolecule that includes at least two monomer units attached to one another. A "biomolecule" refers to an organic molecule that is made and/or used by an organism, and/or that is utilized to analyze the organism or components thereof. Exemplary biomolecules include nucleic acids, nucleotides, amino acids, polypeptides, peptides, peptide fragments, sugars, fatty acids, steroids, lipids, and combinations of these biomolecules (e.g., glycoproteins, ribonucleoproteins, or lipoproteins).

The term "captured" in the context of solid supports and target analytes refers to an analyte that is directly or indirectly joined or attached to a solid support via a covalent linkage, chelation, ionic interaction, and/or another mechanism. In some embodiments, target analytes are reversibly captured on solid supports, whereas in other embodiments, they are permanently captured.

The term "communicate" refers to the direct or indirect transfer or transmission, and/or capability of directly or indirectly transferring or transmitting, something at least from one thing to another thing. Objects "fluidly communicate" with one another when fluidic material is, or is capable of being, transferred from one object to another. In some embodiments, for example, material transfer components add and/or remove materials to/from the containers of sample processing units during a given purification process. Objects are in "magnetic communication" with one another when one object exerts or can exert a magnetic field of sufficient strength on another object to effect a change (e.g., a change in position or other movement) in the other object. In some embodiments, for example, containers (e.g., cuvettes, etc.) of sample processing units are moved sufficiently proximal to sample processing unit magnets such that magnetic fields generated by the magnets cause magnetically responsive particles (e.g., magnetically responsive beads with bound or otherwise captured nucleic acids) disposed within the containers to move and/or be retained proximal to surfaces of the containers when a given purification processing is being performed. Objects are in "sensory communication" when a characteristic or property of one object is or can be sense, perceived, or otherwise detected by another object. In certain embodiments, for example, carrier mechanisms of the systems described herein rotate the containers of sample processing units within sensory communication with detectors to detect one or more parameters (e.g., fluorescence, temperature, pH, or the like) of fluidic materials disposed in the containers.

The term "material" refers to something comprising or consisting of matter. The term "fluidic material" refers to material (such as, a liquid or a gas) that tends to flow or conform to the outline of its container.

The term "microplate" refers to a plate or other support structure that includes multiple cavities or wells that are structured to contain materials, such as fluidic materials. The wells typically have volume capacities of less than about 1.5 mL (e.g., about 1000 µL, about 800 µL, about 600 µL, about 400 µL, or less), although certain microplates (e.g., deep-well plates, etc.) have larger volume capacities, such as about 4 mL per well. Microplates can include various numbers of wells, for example, 6, 12, 24, 48, 96, 384, 1536, 3456, 9600, or more wells. In addition, the wells of a microplate are typically arrayed in a rectangular matrix. Microplates generally conform to the standards published by the American National Standards Institute (ANSI) on behalf of the Society for Biomolecular Screening (SBS), namely, ANSI/SBS 1-2004: Microplates—Footprint Dimensions, ANSI/SBS 2-2004: Microplates—Height Dimensions, ANSI/SBS 3-2004: Microplates—Bottom Outside Flange Dimensions, and ANSI/SBS 4-2004: Microplates—Well Positions, which are each incorporated by reference. Microplates are available from a various manufacturers including, e.g., Greiner America Corp. (Lake Mary, Fla., U.S.A.) and Nalge Nunc International (Rochester, N.Y., U.S.A.), among many others. Microplates are also commonly referred to by various synonyms, such as "microtiter plates," "micro-well plates," "multi-well containers," and the like The term "molecular mass" refers to the mass of a compound as determined using mass spectrometry, for example, ESI-MS. Herein, the compound is preferably a nucleic acid. In some embodiments, the nucleic acid is a double stranded nucleic acid (e.g., a double stranded DNA nucleic acid). In some embodiments, the nucleic acid is an amplicon. When the nucleic acid is double stranded the molecular mass is determined for both strands. In one embodiment, the strands may be separated before introduction into the mass spectrometer, or the strands may be separated by the mass spectrometer (for example, electro-spray ionization will separate the hybridized strands). The molecular mass of each strand is measured by the mass spectrometer.

The term "non-priority microplate" refers to a microplate that is processed or otherwise handled after at least one other microplate, or whose processing or handling is interrupted or deferred in order to process or otherwise handle at least one other microplate, in a given microplate handling system of the invention. That is, the order, schedule, or timing of processing or handling a non-priority microplate is subject to interruption or delay when a higher priority microplate is presented, such as a microplate including stat samples. In some embodiments, non-priority microplates are introduced into a given system via non-priority microplate storage units.

The term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-$N^6$-methyladenosine, aziridinylcytosine, pseudoisocytosine, 5-(carboxyhydroxyl-methyl)-uracil, 5-fluorouracil, 5-bromouracil, 5-carboxymethylaminomethyl-2-thiouracil, 5-carboxymethylaminomethyluracil, dihydrouracil, inosine, $N^6$-isopentenyladenine, 1-methyladenine, 1-methylpseudouracil, 1-methylguanine, 1-methylinosine, 2,2-dimethyl-guanine, 2-methyladenine, 2-methylguanine, 3-methyl-cytosine, 5-methylcytosine, $N^6$-methyladenine, 7-methylguanine, 5-methylaminomethyluracil, 5-methoxy-amino-methyl-2-thiouracil, beta-D-mannosylqueosine, 5'-methoxycarbonylmethyluracil, 5-methoxyuracil, 2-methylthio-N-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "priority microplate" refers to a microplate that is processed or otherwise handled before the processing or handling of a non-priority microplate is commenced or completed in a given microplate handling system of the invention. In some embodiments, one or more wells of priority microplates comprise stat or urgent samples. In certain embodiments, priority microplates are introduced into a given system via priority microplate storage units.

The phrase "solid support" refers to a solid material that can be derivatized with, or otherwise attached to, a chemical or biochemical moiety. Exemplary solid supports that are optionally utilized include matrices and particles free in solution, such as glass (e.g., controlled pore glass (CPG)), nitrocellulose, polyacrylate, nylon, mixed polymers, silane polypropylene, polystyrene, magnetically attractable or responsive particles (e.g., magnetic spheres or beads), and the like.

The term "system" refers a group of objects and/or devices that form a network for performing a desired objective. In some embodiments, for example, sample processing units having fluidic materials with magnetically responsive particles are included as part of systems in which nucleic acids are purified using the magnetically responsive particles such that the molecular masses of the nucleic acids can be more readily detected by mass spectrometers of these systems.

II. Introduction

The invention relates to sample purification, and in various embodiments provides sample processing units, carrier mechanisms, sample processing stations, systems, and related methods that are useful for this purpose. The sample processing units and related aspects of the invention can be used, or adapted for use, in a wide variety of sample purification processes. In certain embodiments, for example, microplates comprising nucleic acid amplification reaction mixtures are loaded into microplate storage units of a microplate handling system. In some of these embodiments, a microplate transport mechanism of the system transports the microplates to a microplate processing area, where a material transfer component transfers aliquots of the reaction mixtures from the wells of the microplates to a sample processing system. In these embodiments, the sample processing system is typically used to purify amplification products or amplicons in the reaction mixture aliquots for subsequent detection or other analysis. To further illustrate, in some of these embodiments, the molecular masses of these purified amplicons are measured using a mass spectrometer, e.g., an electrospray ionization time-of-flight mass spectrometer or the like. The base compositions of the amplicons are typically determined from the measured molecular masses and correlated with an identity or source of target nucleic acids in the amplification reaction mixtures, such as a pathogenic organism.

Particular embodiments of molecular mass-based detection methods and other aspects that are optionally adapted for use with the sample processing units and related aspects of the invention are described in various patents and patent applications, including, for example, U.S. Pat. Nos. 7,108,974; 7,217,510; 7,226,739; 7,255,992; 7,312,036; and 7,339,051; and US patent publication numbers 2003/0027135; 2003/0167133; 2003/0167134; 2003/0175695; 2003/0175696; 2003/0175697; 2003/0187588; 2003/0187593; 2003/0190605; 2003/0225529; 2003/0228571; 2004/0110169; 2004/0117129; 2004/0121309; 2004/0121310; 2004/0121311; 2004/0121312; 2004/0121313; 2004/0121314; 2004/0121315; 2004/0121329; 2004/0121335; 2004/0121340; 2004/0122598; 2004/0122857; 2004/0161770; 2004/0185438; 2004/0202997; 2004/0209260; 2004/0219517; 2004/0253583; 2004/0253619; 2005/0027459; 2005/0123952; 2005/0130196 2005/0142581; 2005/0164215; 2005/0266397; 2005/0270191; 2006/0014154; 2006/0121520; 2006/0205040; 2006/0240412; 2006/0259249; 2006/0275749; 2006/0275788; 2007/0087336; 2007/0087337; 2007/0087338 2007/0087339; 2007/0087340; 2007/0087341; 2007/0184434; 2007/0218467; 2007/0218467; 2007/0218489; 2007/0224614; 2007/0238116; 2007/0243544; 2007/0248969; WO2002/070664; WO2003/001976; WO2003/100035; WO2004/009849; WO2004/052175; WO2004/053076; WO2004/053141; WO2004/053164; WO2004/060278; WO2004/093644; WO 2004/101809; WO2004/111187; WO2005/023083; WO2005/023986; WO2005/024046; WO2005/033271; WO2005/036369; WO2005/086634; WO2005/089128; WO2005/091971; WO2005/092059; WO2005/094421; WO2005/098047; WO2005/116263; WO2005/117270; WO2006/019784; WO2006/034294; WO2006/071241; WO2006/094238; WO2006/116127; WO2006/135400; WO2007/014045; WO2007/047778; WO2007/086904; and WO2007/100397; WO2007/118222, which are each incorporated by reference as if fully set forth herein.

Exemplary molecular mass-based analytical methods and other aspects of use in the sample processing units and systems described herein are also described in, e.g., Ecker et al. (2005) "The Microbial Rosetta Stone Database: A compilation of global and emerging infectious microorganisms and bioterrorist threat agents" *BMC Microbiology* 5(1):19; Ecker et al. (2006) "The Ibis T5000 Universal Biosensor: An Automated Platform for Pathogen Identification and Strain Typing" *JALA* 6(10:341-351; Ecker et al. (2006) "Identification of Acinetobacter species and genotyping of *Acinetobacter baumannii* by multilocus PCR and mass spectrometry" *J Clin Microbiol.* 44(8):2921-32; Ecker et al. (2005) "Rapid identification and strain-typing of respiratory pathogens for epidemic surveillance" *Proc Natl Acad Sci USA.* 102(22):8012-7; Hannis et al. (2008) "High-resolution genotyping of *Campylobacter* species by use of PCR and high-throughput mass spectrometry" *J Clin Microbiol.* 46(4):1220-5; Blyn et al. (2008) "Rapid detection and molecular serotyping of adenovirus by use of PCR followed by electrospray ionization mass spectrometry" *J Clin Microbiol.* 46(2):644-51; Sampath et al. (2007) "Global surveillance of emerging Influenza virus genotypes by mass spectrometry" *PLoS ONE* 2(5): e489; Sampath et al. (2007) "Rapid identification of emerging infectious agents using PCR and electrospray ionization mass spectrometry" *Ann N Y Acad. Sci.* 1102:109-20; Hall et al. (2005) "Base composition analysis of human mitochondrial DNA using electrospray ionization mass spectrometry: a novel tool for the identification and differentiation of humans" *Anal Biochem.* 344(1):53-69; Hofstadler et al. (2003) "A highly efficient and automated method of purifying and desalting PCR products for analysis by electrospray ionization mass spectrometry" *Anal Biochem.* 316:50-57; Hofstadler et al. (2006) "Selective ion filtering by digital thresholding: A method to unwind complex ESI-mass spectra and eliminate signals from low molecular weight chemical noise" *Anal Chem.* 78(2):372-378; and Hofstadler et al. (2005) "TIGER: The Universal Biosensor" *Int J Mass Spectrom.* 242(1):23-41, which are each incorporated by reference.

In addition to the molecular mass and base composition analyses referred to above, essentially any other nucleic acid amplification technological process is also optionally adapted for use in the systems of the invention. Other exemplary uses of the systems and other aspects of the invention include numerous biochemical assays, cell culture purification steps, and chemical synthesis, among many others. Many of these as well as other exemplary applications of use in the systems of the invention are also described in, e.g., Current Protocols in Molecular Biology, Volumes I, II, and III, 1997 (F. M. Ausubel ed.); Perbal, 1984, A Practical Guide to Molecular Cloning; the series, Methods in Enzymology (Academic Press, Inc.); Sambrook et al., 2001, Molecular Cloning: A Laboratory Manual, Third Edition, Cold Spring Harbor Laboratory Press, Cold Spring Harbor, N.Y.; Oligonucleotide Synthesis, 1984 (M. L. Gait ed.); Nucleic Acid Hybridization, 1985, (Hames and Higgins); Transcription and Translation, 1984 (Hames and Higgins eds.); Animal Cell Culture, 1986 (R. I. Freshney ed.); Berger and Kimmel, Guide to Molecular Cloning Techniques, Methods in Enzymology volume 152 Academic Press, Inc., San Diego, Calif. (Berger), DNA Cloning: A Practical Approach, Volumes I and II, 1985 (D. N. Glover ed.); Immobilized Cells and Enzymes, 1986 (IRL Press); Gene Transfer Vectors for Mammalian Cells, 1987 (J. H. Miller and M. P. Calos eds., Cold Spring Harbor Laboratory); and Methods in Enzymology Vol. 154 and Vol. 155 (Wu and Grossman, and Wu, eds., respectively), which are each incorporated by reference.

III. Example Sample Processing Units and Carrier Mechanisms

FIGS. 1A-D schematically illustrate a sample processing unit or components thereof according to one embodiment of the invention. As shown, sample processing unit 100 includes cuvette 102 operably connected to first motor 104 (shown as a brushless DC motor). First motor 104 (i.e., one embodiment of a rotational mechanism) is configured to rotate cuvette 102 around a central longitudinal axis of cuvette 102. As also shown, first motor 104 is operably connected to support member 106 (shown as a swing arm). First motor 104 is optionally configured (e.g., under the control of an appropriately programmed controller) to rotate cuvette 102 in at least one pulsed mode, during which a substantial portion of the time of rotation, a rate of rotation of cuvette 102 exceeds a rate of rotation of sample material in cuvette 102 such that the sample material is sheared away from a surface of cuvette 102, e.g., to effect mixing of the sample material. To further illustrate, first motor 104 is optionally configured (e.g., again under the control of an appropriately programmed controller) to rotate cuvette 102 in at least one oscillating motion, e.g., also to effect mixing of sample materials. Controllers and rotational modes are described further herein.

Support member 106 is also operably connected to second motor 108 (shown as a brushless direct current motor) via mounting bracket 110. Support member 106 includes first end 112 and second end 114. Cuvette 102 is retained proximal to first end 112 of support member 106 via first motor 104, whereas second motor 108 is operably connected to support member 106 proximal to second end 114 of support member 106. Support member 106 is configured to rotate at least partially around a rotational axis extending through and proximal to second end 114 of support member 106. Pin 116 is fixedly coupled to second end 114 of support member 106 and aligned with the rotational axis. Pin 116 is also operably coupled to second motor 108, which effects rotation of cuvette 102 between second position 118 (e.g., a cuvette rotational or spin position) and first position 120 via pin 116 and support member 106. Collectively, second motor 108, pin 116, and support member 106 are components of one embodiment of an exemplary conveyance mechanism. As additionally shown, sample processing unit 100 includes circuitry 122 that electrically connects to first motor 104, second motor 108, and a controller or power source (not shown) to effect control of first motor 104 and second motor 108.

Sample processing unit 100 also includes magnets 124 (shown as permanent magnets) attached to magnet mounting arm 126, e.g., to facilitate certain processing steps that involve magnetically-based separation of materials. In some embodiments, electromagnets are utilized. Magnet mounting arm 126 is operably connected to mounting bracket 110 and holds magnets 124 in substantially fixed positions relative to cuvette 102 and support member 106. Magnets 124 are disposed proximal to receiving space 126. As illustrated, for example, in FIGS. 1 B and C, when cuvette 102 is in first position 120, cuvette 102 is located at least partially within receiving space 128.

In certain embodiments, the sample processing unit includes only a single magnet attached to mounting bracket via a magnet mounting arm in a substantially fixed positions relative to a cuvette, support member, and first motor. In addition to a support member, the conveyance mechanism of an exemplary sample processing unit may also include a second motor, which conveys a cuvette between a first position and a second position.

Figure 3A:
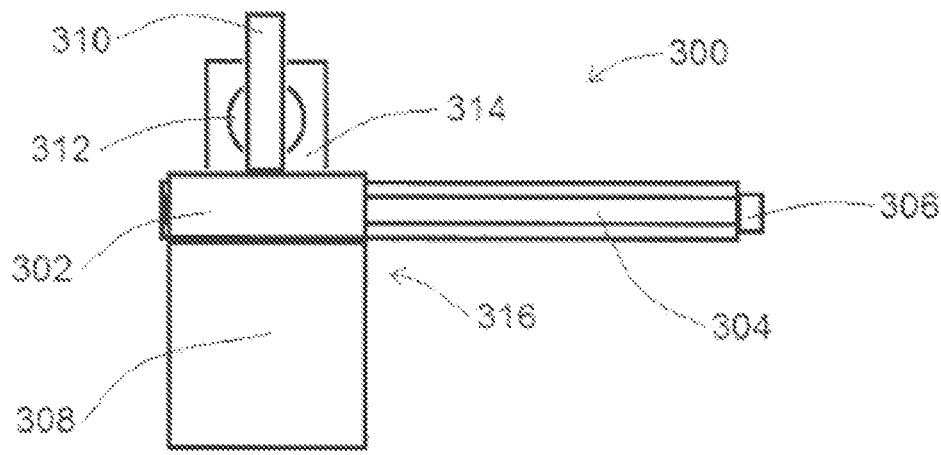
FIG. 3A schematically shows a sample processing unit with a slidable support member in a first position from a front elevation view according to one embodiment of the invention.
Figure 3B:
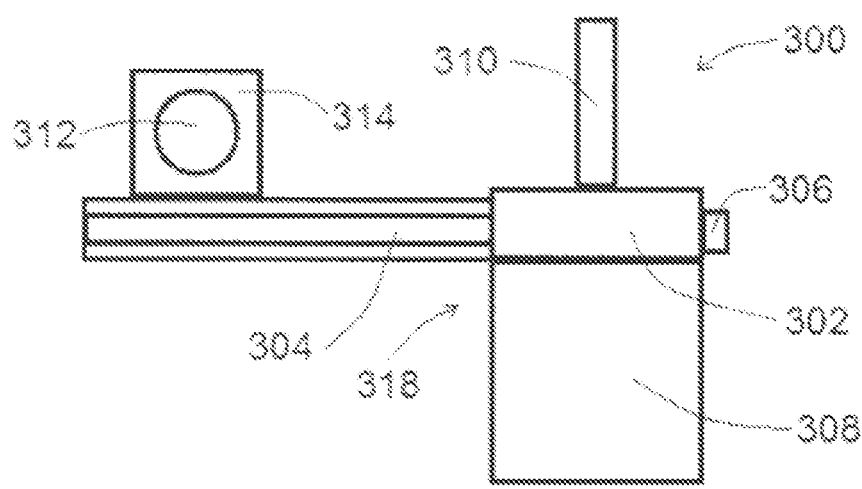
FIG. 3B schematically depicts the sample processing unit of FIG. with the slidable support member in a second position from a perspective view.
Figure 4A:
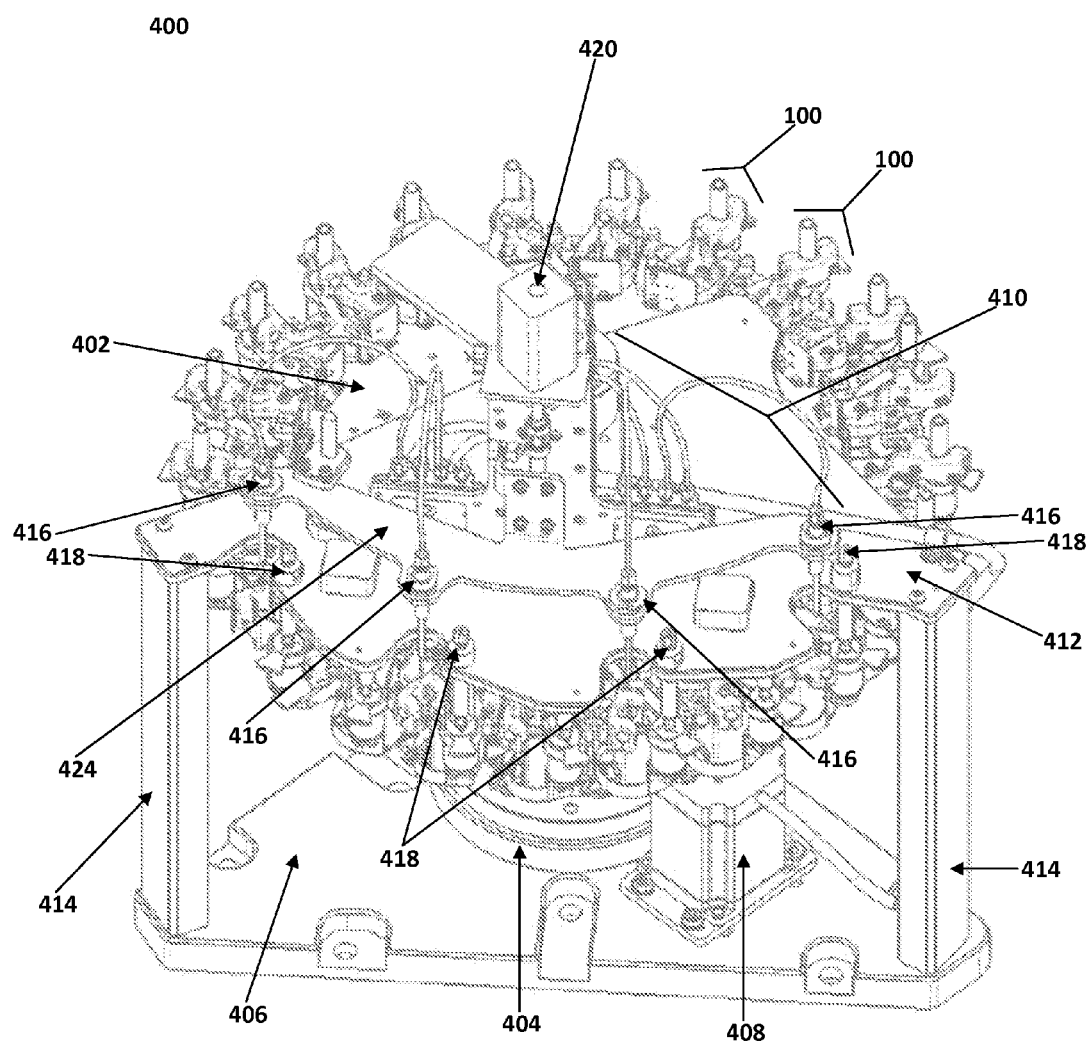
FIG. 4A schematically illustrates a carrier mechanism with a manifold from a perspective view according to one embodiment of the invention.
Figure 4B:
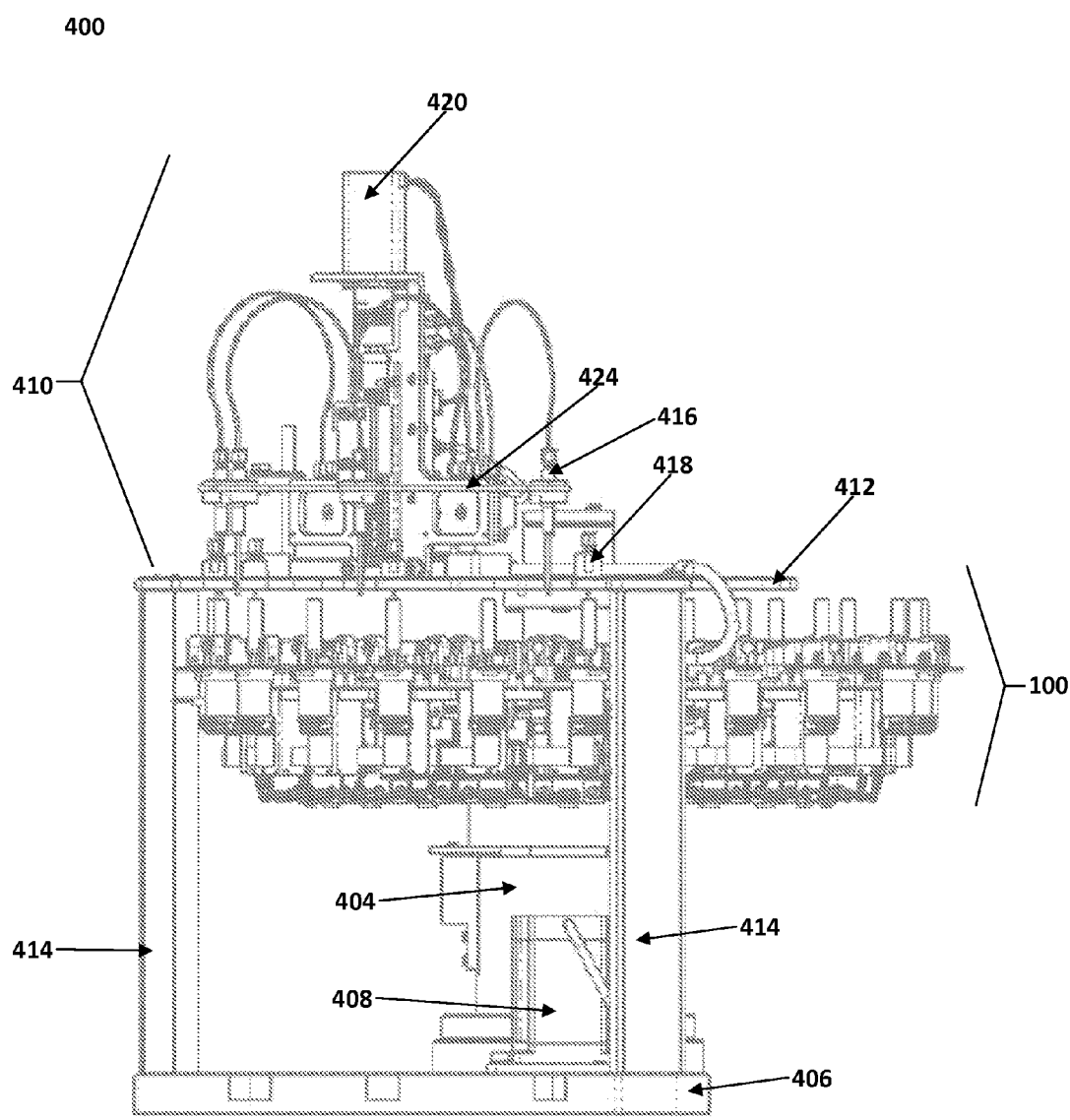
FIG. 4B schematically shows the carrier mechanism and manifold of FIG. 4A from a side elevation view.
Figure 4C:
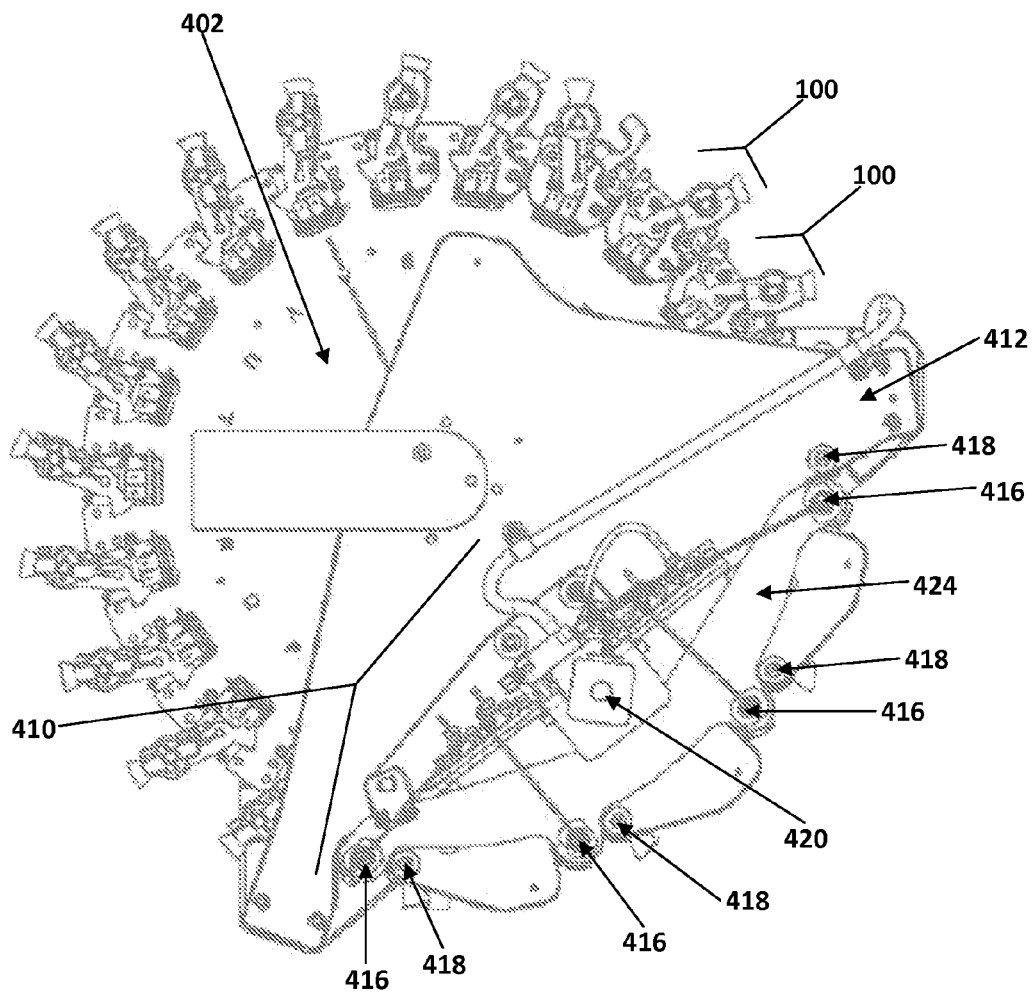
FIG. 4C schematically shows the carrier mechanism and manifold of FIG. 4A from a top view.
Figure 4D:
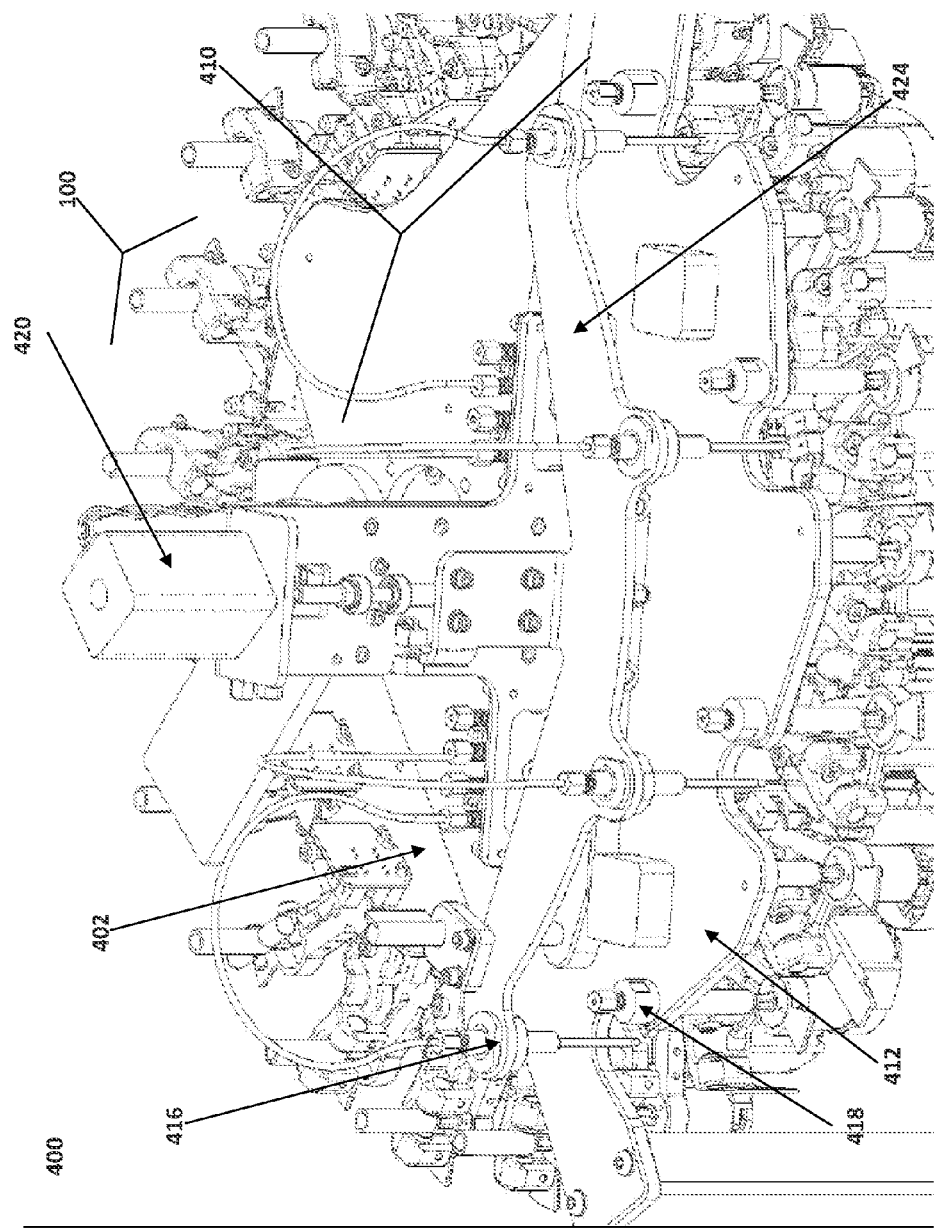
FIG. 4D schematically illustrates a detailed perspective view of the carrier mechanism and manifold of FIG. 4A.
Figure 4E:
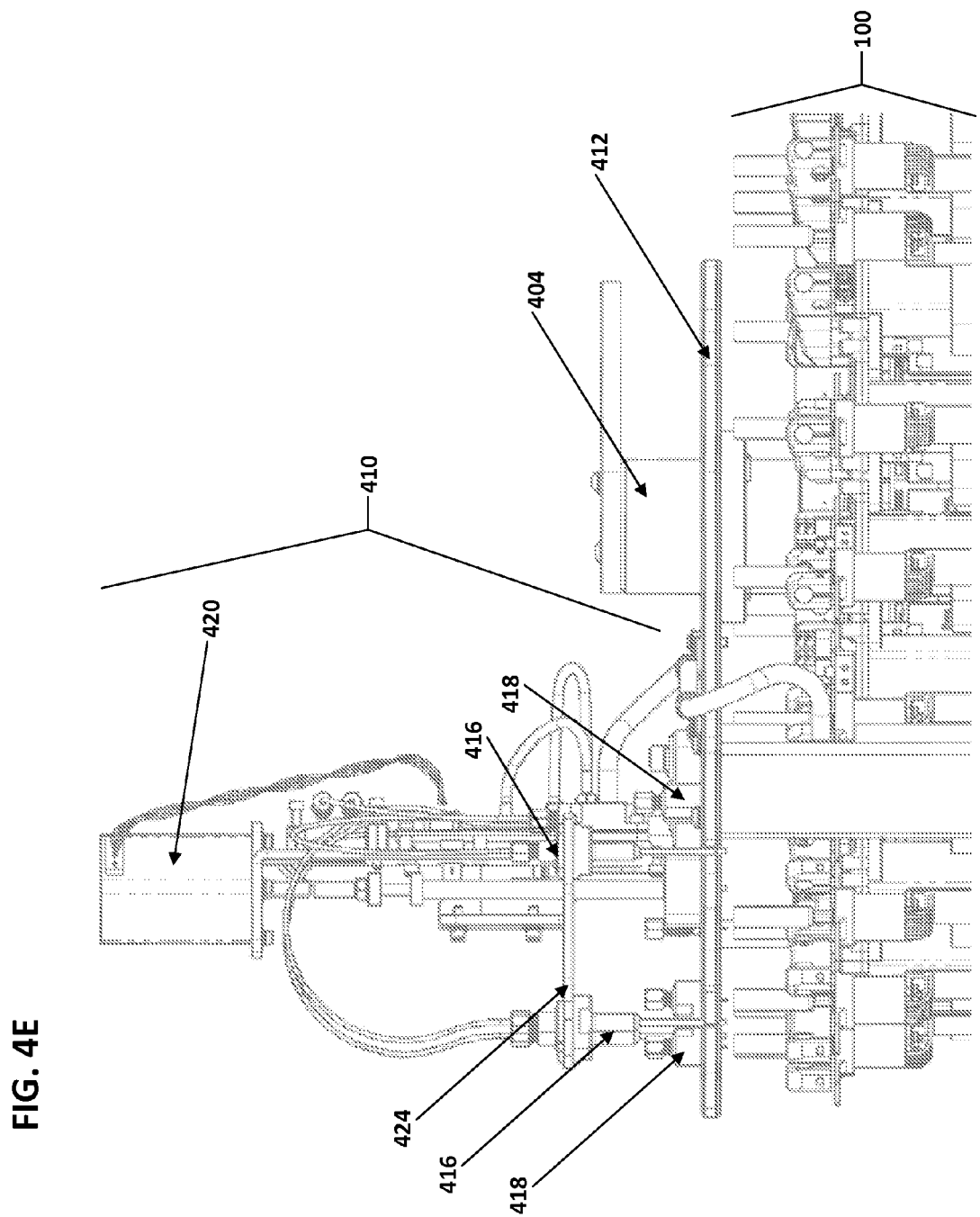
FIG. 4E schematically depicts a detailed side elevation view of the carrier mechanism and manifold of FIG. 4A.
Figure 4F:
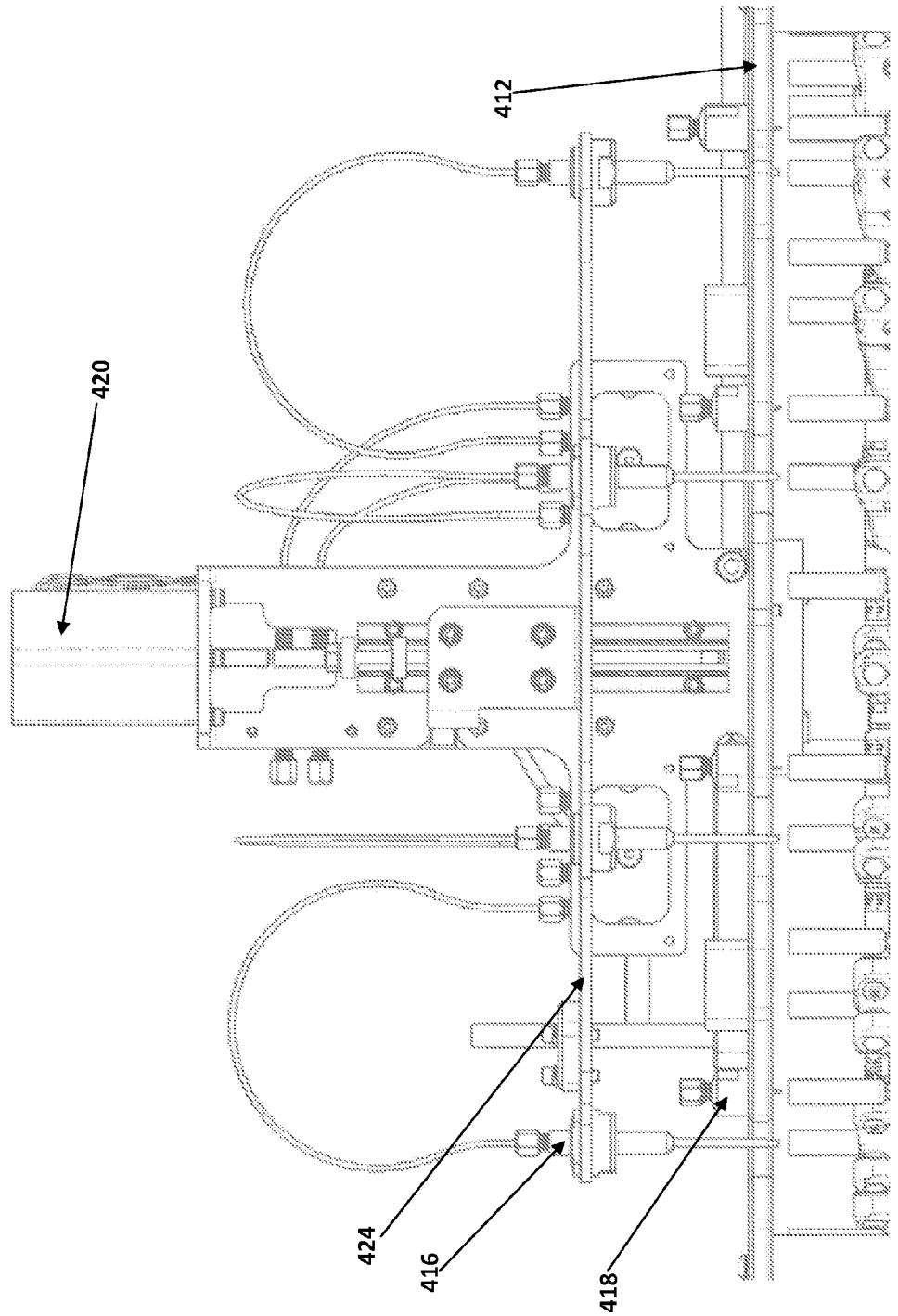
FIG. 4F schematically depicts a detailed front elevation view of the carrier mechanism and manifold of FIG. 4A.

The conveyance mechanisms of the sample processing units of the invention include various embodiments. As mentioned above, in certain embodiments, conveyance mechanisms are configured to rotate cuvettes or other types of containers between selected positions (e.g., between spin mixing, detection, and magnetic particle retention positions). Essentially any other mechanism that can convey containers to and from being within magnetic communication with the magnets of the sample processing units described herein is optionally utilized. As a further illustration, conveyance mechanisms include slidable support members in some embodiments. As shown in FIGS. 3A and B, for example, the conveyance mechanism of sample processing unit 300 includes support member 302 and gantry or linear slide track 304. Linear drive mechanism 306 is configured to move support member 302 along linear slide track 304. Further, rotational mechanism 308 (e.g., a motor or the like) is operably coupled with container 310 via support member 302. In addition, magnet 312 is operably connected to linear slide track 304 in a substantially fixed position via magnet mounting arm 314. Support member 302 and container 310 are shown in first position 316 in FIG. 3A, whereas they are shown in second position 318 in FIG. 3B.

In certain embodiments, carrier mechanisms are operably connected to sample processing units. Carrier mechanisms are typically configured to move sample processing units to one or more locations, e.g., where various processing steps are performed, such as adding and/or removing fluidic materials from sample processing unit containers. Typically, multiple sample processing units are included on a given carrier mechanism, e.g., to enhance the throughput of sample processing applications performed using the carrier mechanism. In some embodiments, for example, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more sample processing units are included on a given carrier mechanism. In addition, essentially any carrier mechanism format that can be used to move sample processing units to selected locations is optionally utilized. In some embodiments, for example, a carrier mechanism includes a carousel that is configured to rotate sample processing units to selected locations. In another representative embodiment, a carrier mechanism includes a conveyor track that is configured to convey sample processing units to one or more locations as desired. Both of these exemplary carrier mechanism embodiments are described further herein. To further illustrate, manifolds for substantially simultaneously distributing fluidic materials to and/or from the containers of multiple sample processing units of a given carrier mechanism are included in certain embodiments, e.g., to enhance process throughput.

One embodiment of a carrier mechanism with a manifold is schematically depicted in FIG. 4 A-F from various points of view. As shown, carousel 400 includes 22 sample processing units 100 mounted on circular support structure 402, which is operably connected to rotating assembly 404. Rotating assembly 404 includes a slip ring or rotary electrical interface that effects rotation of circular support structure 402 and sample processing units 100 to selected positions around carousel 400. Rotating assembly 404 is mounted on support base 406, which provides structural support to carousel 400. Carousel 400 control includes motor 408 (e.g., a stepper motor, such as a Model No. 5704M-10 or 5709L-06PD available from Lin Engineering, Santa Clara, Calif., U.S.A.) and one or more transmissive photomicrosensors (e.g., a Model No. EE-SX1071 available from Omron Electronics LLC, Schaumburg, Ill., U.S.A.).

As additionally shown, sample cleanup station or manifold 410 is also mounted above carousel 400 on manifold support structure 412, which is connected to rotating assembly 404 and manifold support pillars 414. Manifold 410 is used to aspirate and dispense fluidic materials from/into cuvettes 102 of sample processing units 100 as part of sample purification procedures. More specifically, manifold 410 includes aspirate heads 416 and dispense heads 418. Aspirate heads 416 typically fluidly communicate with fluidic material waste containers (not within view) via flexible tubing, whereas dispense heads 418 generally fluidly communicate with fluidic material sources or reservoirs via flexible tubing. Fluidic material is typically conveyed through the tubing using a fluid conveyance mechanism, such as a pump (e.g., a peristaltic pump, a vacuum pump, or the like). Manifold motor and linear motion component 420, which includes manifold stepper motor (e.g., a Model No. 211-13-02 or 211-20-02 available from Lin Engineering, Santa Clara, Calif., U.S.A.), is configured to raise and lower manifold plate 424. As shown, aspirate heads 416 are mounted on manifold plate 424. When fluidic materials are aspirated from cuvettes 102, rotating assembly 404 typically rotates selected cuvettes 102 into alignment with selected aspirate heads 416. Manifold motor and linear motion component 420 then typically lowers aspirate heads 416 such that needles of aspirate heads 416 contact fluidic materials disposed within the selected cuvettes 102 so that selected volumes of the fluidic materials can be aspirated from the selected cuvettes 102. In some of these embodiments, magnetically responsive particles (with bound or otherwise captured nucleic acids or other analytes) are included in the fluidic materials. In these embodiments, the selected cuvettes 102 are typically moved into magnetic communication with magnets 124 of the corresponding sample processing units 100 so that the magnetically responsive particles are retained within the selected cuvettes 102 as the selected aliquots are removed through the needles of the selected aspirate heads 416. After a given fluidic material aspiration step is performed, manifold motor and linear motion component 420 typically raises manifold plate 424 and aspirate heads 416 a sufficient distance such that rotating assembly 404 can rotate cuvettes 102 to other locations without contacting the needles of aspirate heads 416. As further illustrated, dispense heads 418 are mounted in substantially fix positions on manifold support structure 412 such that they can fluidly communicate with cuvettes 102 when cuvettes 102 are positioned beneath and aligned with the needles of dispense heads 418. During operation, e.g., before or after a given aspiration step is performed, rotating assembly 404 typically rotates selected cuvettes 102 into alignment with selected dispense heads 418 so that selected volumes of fluidic material (e.g., reagent mixtures, elution buffers, etc.) can be dispensed into the selected cuvettes 102. Before or after a given aspiration or dispensing step is performed, selected cuvettes 102 are typically spun using first motors 104 of sample processing units 100 to mix fluidic materials in the selected cuvettes 102. Exemplary systems that include carousels and manifolds are described further herein.

Figure 5A:
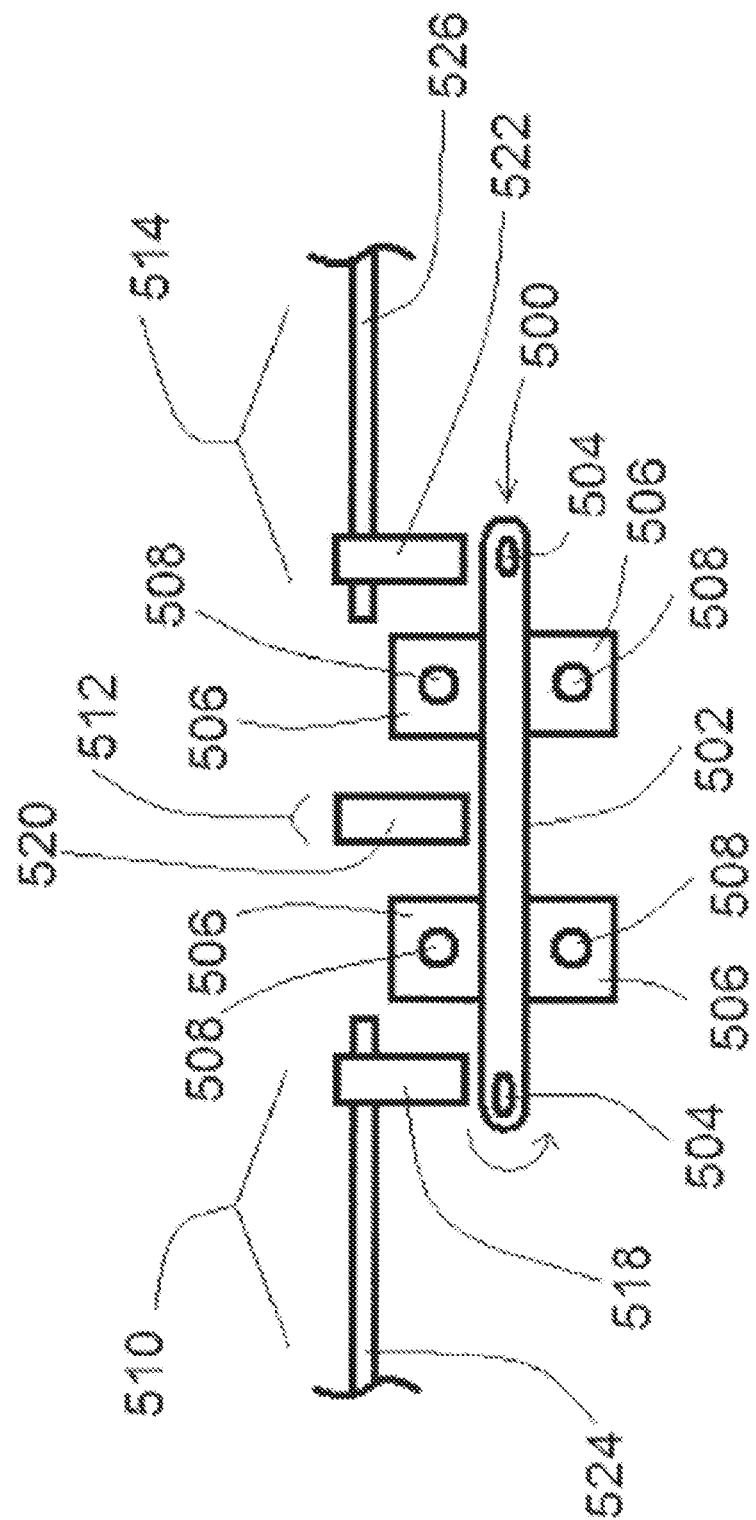
FIG. 5A schematically illustrates a carrier mechanism that includes a conveyor track from a top view according to one embodiment of the invention.
Figure 5B:
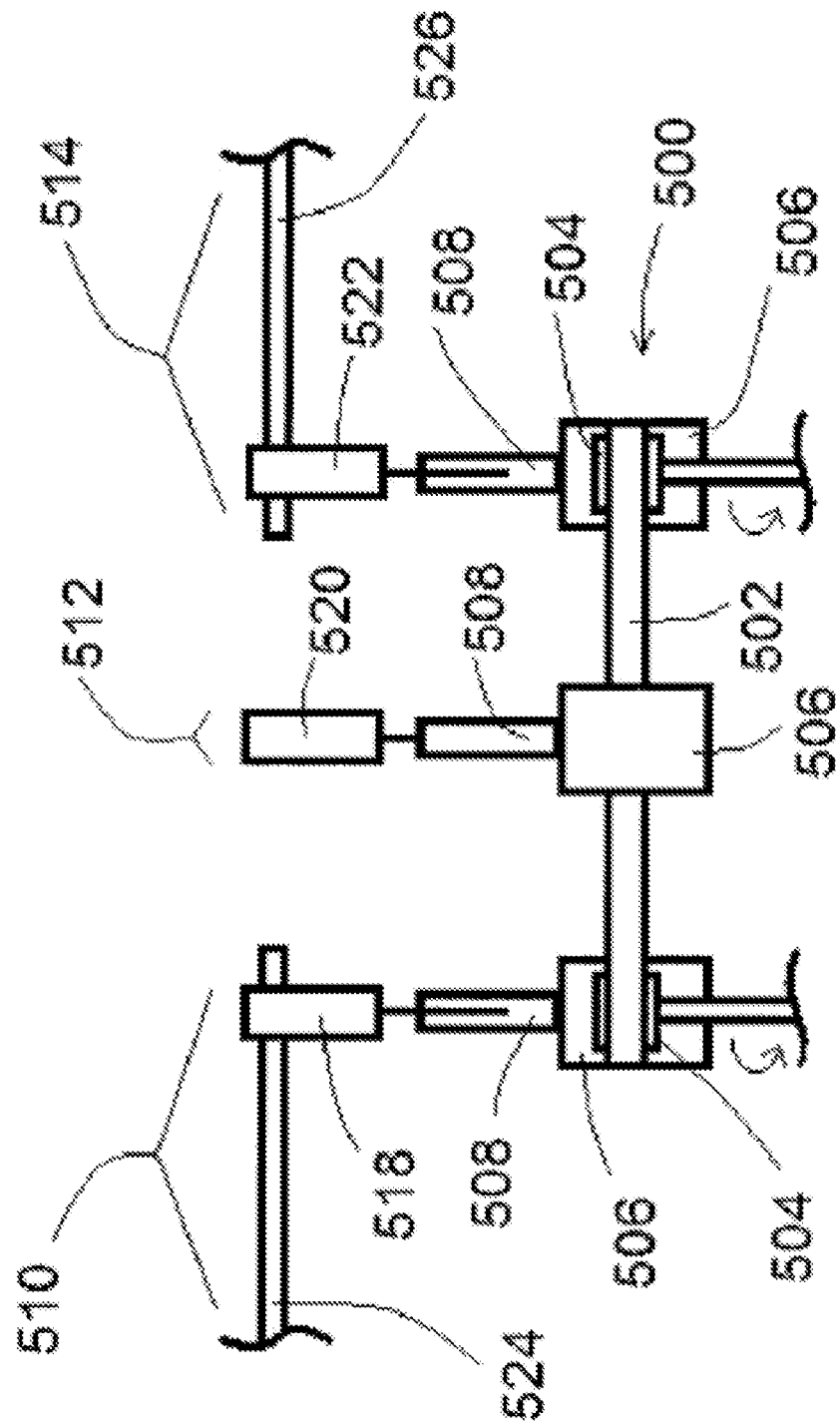
FIG. 5B schematically illustrates the carrier mechanism from FIG. 5A from a side elevation view.

To illustrate another exemplary embodiment, FIGS. 5 A and B schematically depict a carrier mechanism that includes a conveyor track from top and side elevation views, respectively. As shown, carrier mechanism 500 includes conveyor track 502 (e.g., a conveyor belt, etc.), which is configured to rotate counter-clockwise around rotational couplings 504 (e.g., pulleys or the like). Sample processing units 506, which include containers 508, are connected to conveyor track 502. During operation, rotational couplings 504 rotate sample processing units 506 to fluid transfer stations 510, 512, and 516, which include fluid transfer heads 518, 520, and 522, respectively, that each have an aspirate/dispense needle. Fluid transfer heads 518, 520, and 522 are configured to be raised and lowered. As shown, for example, in FIG. 5B, when sample processing units 506 are aligned beneath fluid transfer heads 518, 520, and 522, the heads are typically lowered so that the aspirate/dispense needles can fluidly communicate with containers 508. Note that the container of the sample processing unit depicted on the near side of conveyor track 502 in FIG. 5B partially obscures the needle of fluid transfer head 520, which is lowered into the container of the sample processing unit (not within view in FIG. 5B) on the far side of conveyor track 502. When sample processing units 506 are rotated around rotational couplings 504, transfer heads 518, 520, and 522 are typically raised a sufficient height to permit the unobstructed passage of containers 508 beneath the needles of transfer heads 518, 520, and 522. As also shown, transfer heads 518 and 522 are also configured to move along gantry tracks 524 and 526, respectively.

IV. Example Controllers and Related Systems

Controllers are typically operably connected to sample processing units and carrier mechanisms, whether they are used as stand-alone sample processing stations or as system components. The controllers of the sample processing stations and systems described herein are generally configured to effect, e.g. the rotation of sample processing unit containers to mix sample materials in the containers (e.g., in various selectable modes of rotation, etc.), the movement of containers to and from being within magnetic communication with the magnets of sample processing units, the movement of carrier mechanisms to position sample processing units relative to material transfer components, the transfer of materials to and from the containers of sample processing units, the detection of one or more parameters of sample materials disposed in the containers of sample processing units or of aliquots of those materials taken from those containers, and the like. Controllers are typically operably connected to one or more system components, such as motors (e.g., via motor drives), thermal modulating components, detectors, motion sensors, fluidic handling components, robotic translocation devices, or the like, to control operation of these components. More specifically, controllers are generally included either as separate or integral system components that are utilized to effect, e.g., the rotation of the containers of sample processing units according to one or more selectable rotational modes, the transfer of materials to and/or from the containers of sample processing units, the detection and/or analysis of detectable signals received from sample materials by detectors, etc. Controllers and/or other system components is/are generally coupled to an appropriately programmed processor, computer, digital device, or other logic device or information appliance (e.g., including an analog to digital or digital to analog converter as needed), which functions to instruct the operation of these instruments in accordance with preprogrammed or user input instructions (e.g., mixing mode selection, fluid volumes to be conveyed, etc.), receive data and information from these instruments, and interpret, manipulate and report this information to the user.

Figure 6:
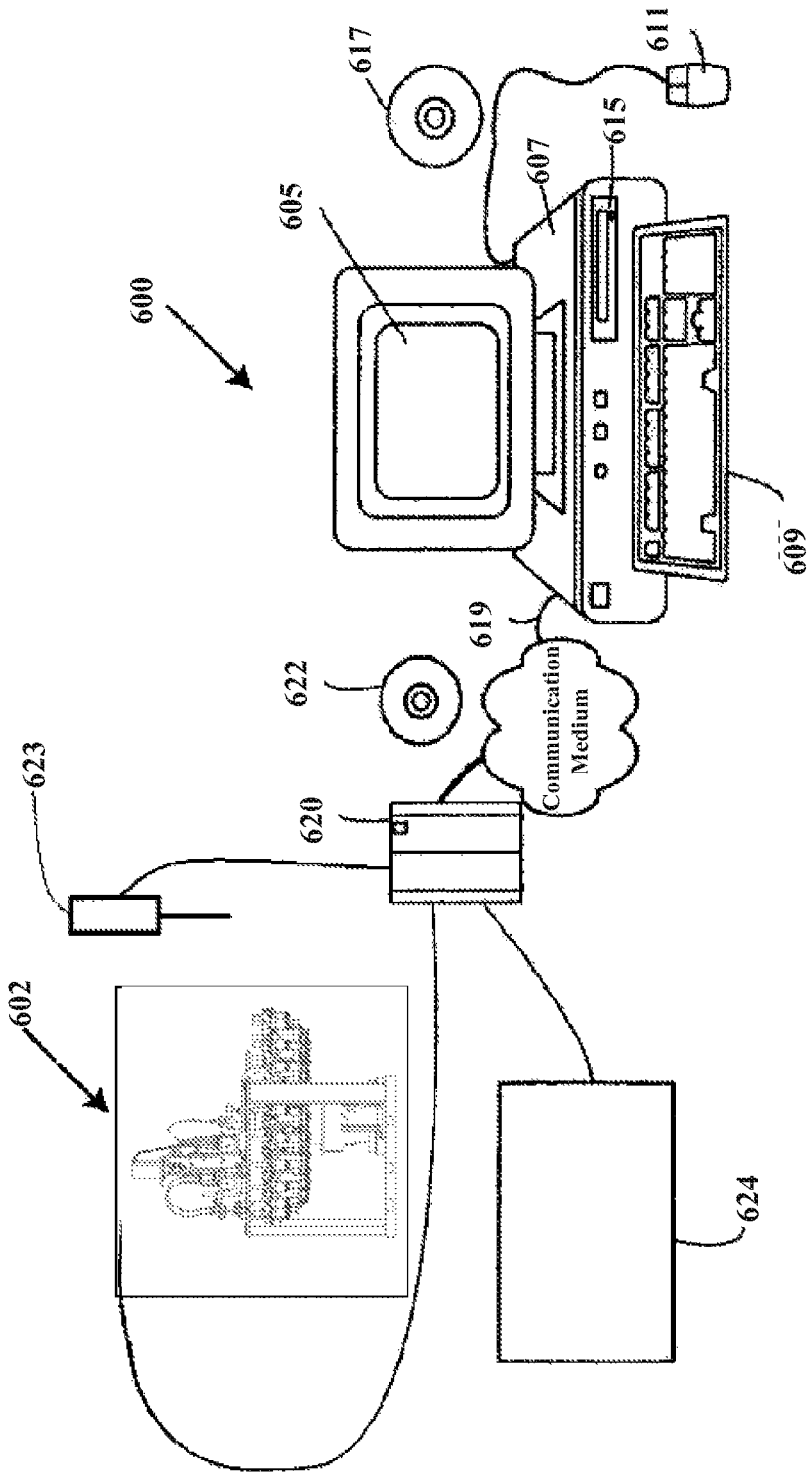
FIG. 6 is a block diagram showing a representative logic device in which various aspects of the present invention may be embodied.

A controller or computer optionally includes a monitor which is often a cathode ray tube ("CRT") display, a flat panel display (e.g., active matrix liquid crystal display, liquid crystal display, etc.), or others. Computer circuitry is often placed in a box, which includes numerous integrated circuit chips, such as a microprocessor, memory, interface circuits, and others. The box also optionally includes a hard disk drive, a floppy disk drive, a high capacity removable drive such as a writeable CD-ROM, and other common peripheral elements. Inputting devices such as a keyboard or mouse optionally provide for input from a user. An exemplary system comprising a computer is schematically illustrated in FIG. 6.

The computer typically includes appropriate software for receiving user instructions, either in the form of user input into a set of parameter fields, e.g., in a GUI, or in the form of preprogrammed instructions, e.g., preprogrammed for a variety of different specific operations. The software then converts these instructions to appropriate language for instructing the operation of one or more controllers to carry out the desired operation, e.g., rotating sample processing unit containers to mix sample materials in the containers, aspirating fluidic materials from sample processing unit containers, dispensing materials into sample processing unit containers, or the like. The computer then receives the data from, e.g., sensors/detectors included within the system, and interprets the data, either provides it in a user understood format, or uses that data to initiate further controller instructions, in accordance with the programming, e.g., such as in monitoring detectable signal intensity, rates or modes of sample processing unit container rotation, or the like.

More specifically, the software utilized to control the operation of the sample processing stations and systems of the invention typically includes logic instructions that selectively direct, e.g., motors to rotate cuvettes in pulsed modes, during which a substantial portion of the time of rotation, a rate of rotation of the cuvettes exceeds a rate of rotation of the samples in the cuvettes such that the samples are sheared away from surfaces of the cuvettes to effect sample mixing, motors to rotate the cuvettes in oscillating motions, and the like. The logic instructions of the software are typically embodied on a computer readable medium, such as a CD-ROM, a floppy disk, a tape, a flash memory device or component, a system memory device or component, a hard drive, a data signal embodied in a carrier wave, and/or the like. Other computer readable media are known to persons of skill in the art. In some embodiments, the logic instructions are embodied in read-only memory (ROM) in a computer chip present in one or more system components, without the use of personal computers.

The computer can be, e.g., a PC (Intel x86 or Pentium chip-compatible DOS™, OS2™, WINDOWST™, WINDOWS NT™, WINDOWS98™, WINDOWS2000™, WINDOWS XP™, WINDOWS Vista™, LINUX-based machine, a MACINTOSHT™, Power PC, or a UNIX-based (e.g., SUN™ work station) machine) or other common commercially available computer which is known to one of skill. Standard desktop applications such as word processing software (e.g., Microsoft Word™ or Corel WordPerfect™) and database software (e.g., spreadsheet software such as Microsoft Excel™, Corel Quattro Pro™, or database programs such as Microsoft Access™ or Paradox™) can be adapted to the present invention. Software for performing, e.g., sample processing unit container rotation, material conveyance to and/or from sample processing unit containers, mixing process monitoring, assay detection, and data deconvolution is optionally constructed by one of skill using a standard programming language such as Visual basic, C, C++, Fortran, Basic, Java, or the like.

The sample processing stations and related systems of the invention optionally include detectors or detection components configured to detect one or more detectable signals or parameters from a given process, e.g., from materials disposed within sample processing unit container or taken therefrom. In some embodiments, systems are configured to detect detectable signals or parameters that are upstream and/or downstream of a given process involving the sample processing units described herein. Suitable signal detectors that are optionally utilized in these systems detect, e.g., pH, temperature, pressure, density, salinity, conductivity, fluid level, radioactivity, luminescence, fluorescence, phosphorescence, molecular mass, emission, transmission, absorbance, and/or the like. In some embodiments, the detector monitors a plurality of signals, which correspond in position to "real time" results. Example detectors or sensors include PMTs, CCDs, intensified CCDs, photodiodes, avalanche photodiodes, optical sensors, scanning detectors, or the like. Each of these as well as other types of sensors is optionally readily incorporated into the sample processing stations and systems described herein. The detector optionally moves relative to the stations, sample containers or other assay components, or alternatively, the stations, sample containers or other assay components move relative to the detector. Optionally, the stations and systems of the invention include multiple detectors. In these stations and systems, such detectors are typically placed either in or adjacent to, e.g., a sample processing unit cuvette or other vessel, such that the detector is in sensory communication with the sample processing unit cuvette or other vessel (i.e., the detector is capable of detecting the property of the cuvette or vessel or portion thereof, the contents of a portion of the cuvette or vessel, or the like, for which that detector is intended).

The detector optionally includes or is operably linked to a computer, e.g., which has system software for converting detector signal information into assay result information or the like. For example, detectors optionally exist as separate units, or are integrated with controllers into a single instrument. Integration of these functions into a single unit facilitates connection of these instruments with the computer, by permitting the use of a few or even a single communication port for transmitting information between system components. Detection components that are optionally included in the systems of the invention are described further in, e.g., Skoog et al., Principles of Instrumental Analysis, 6$^{th}$ Ed., Brooks Cole (2006) and Curren, Analytical Instrumentation: Performance Characteristics and Quality, John Wiley & Sons, Inc. (2000), which are both incorporated by reference.

The sample processing stations and systems of the invention optionally also include at least one robotic translocation or gripping component that is structured to grip and translocate containers or other processing components between components of the stations or systems and/or between the stations or systems and other locations (e.g., other work stations, etc.). A variety of available robotic elements (robotic arms, movable platforms, etc.) can be used or modified for use with these systems, which robotic elements are typically operably connected to controllers that control their movement and other functions.

FIG. 6 is a schematic showing a representative system including an information appliance in which various aspects of the present invention may be embodied. Other exemplary systems are also described herein. As will be understood by practitioners in the art from the teachings provided herein, the invention is optionally implemented in hardware and software. In some embodiments, different aspects of the invention are implemented in either client-side logic or server-side logic. As will also be understood in the art, the invention or components thereof may be embodied in a media program component (e.g., a fixed media component) containing logic instructions and/or data that, when loaded into an appropriately configured computing device, cause that apparatus or system to perform according to the invention. As will additionally be understood in the art, a fixed media containing logic instructions may be delivered to a viewer on a fixed media for physically loading into a viewer's computer or a fixed media containing logic instructions may reside on a remote server that a viewer accesses through a communication medium in order to download a program component.

FIG. 6 shows information appliance or digital device 600 that may be understood as a logical apparatus (e.g., a computer, etc.) that can read instructions from media 617 and/or network port 619, which can optionally be connected to server 620 having fixed media 622. Information appliance 600 can thereafter use those instructions to direct server or client logic, as understood in the art, to embody aspects of the invention. One type of logical apparatus that may embody the invention is a computer system as illustrated in 600, containing CPU 607, optional input devices 609 and 611, disk drives 615 and optional monitor 605. Fixed media 617, or fixed media 622 over port 619, may be used to program such a system and may represent a disk-type optical or magnetic media, magnetic tape, solid state dynamic or static memory, or the like. In specific embodiments, the aspects of the invention may be embodied in whole or in part as software recorded on this fixed media. Communication port 619 may also be used to initially receive instructions that are used to program such a system and may represent any type of communication connection. Optionally, aspects of the invention are embodied in whole or in part within the circuitry of an application specific integrated circuit (ACIS) or a programmable logic device (PLD). In such a case, aspects of the invention may be embodied in a computer understandable descriptor language, which may be used to create an ASIC, or PLID.

In addition, FIG. 6 also shows sample processing station 602, which is operably connected to information appliance 600 via server 620. Optionally, sample processing station 602 is directly connected to information appliance 600. During operation, sample processing station 602 typically mixes and retains selected materials (e.g., magnetically responsive particles with captured target materials, etc.) in the cuvettes of the sample processing units of sample processing station 602, e.g., as part of an assay or other process. FIG. 6 also shows material transfer component 623 and detector 624, which are optionally included in the systems of the invention. As shown, material transfer component 623 and detector 624 are operably connected to information appliance 600 via server 620. In some embodiments, material transfer component 623 and/or detector 624 is directly connected to information appliance 600. Material transfer component 623 is typically configured to transfer materials to and/or from the cuvettes of the sample processing units of sample processing station 602. In certain embodiments, detector 624 is configured to detect detectable signals produced in the cuvettes of the sample processing units of sample processing station 602 or in aliquots of materials removed from and/or to be added to those cuvettes.

V. Example Sample Processing System and Related Process Embodiments

To further illustrate exemplary embodiments of the invention, FIG. 7 A-G schematically depict a portion of a representative system for nucleic acid amplification product desalting and molecular mass measurement that includes a sample processing station as a sub-system component. The measured molecular masses of the amplification products are typically used to determine base compositions of the corresponding amplification products, which are then generally correlated with the identities or organismal sources of the initial template nucleic acids, for example, as part of a research or in-vitro diagnostic application, among many others.

As shown in FIG. 7 A-G, components of representative system 700 include microplate handling component or system 10, material transfer component 702, mixing station 704, wash stations 706 and 708, sample processing component 710, and sample injector 712. During operation, microplates are typically stored or positioned in input non-priority microplate storage unit 12, output non-priority microplate storage unit 14, priority microplate storage unit 16, microplate processing area 18, and non-priority microplate holding area 20 (e.g., on non-priority microplate holding component 22) of microplate handling component 10. As also shown, microplate handling component 10 also includes barcode reader 36. In the exemplary embodiment shown, barcode reader 36 is configured to read barcodes disposed on microplates when the microplates are disposed in or proximal to non-priority microplate holding area 20, e.g., to track the microplates or samples contained in the microplates in microplate handling system 10. In some embodiments, for example, non-priority microplates are stored in input non-priority microplate storage unit 12 and priority microplates are stored in priority microplate storage unit 16 after target regions of template nucleic acids in those plates have been amplified, e.g., at a separate thermocycling station or nucleic acid amplification component. Essentially any thermal cycling station or device is optionally adapted for use with a system of the invention, such as system 700. Examples of suitable thermocycling devices that are optionally utilized are available from many different commercial suppliers, including Mastercycler® devices (Eppendorf North America, Westbury, N.Y., U.S.A.), the COBAS® AMPLICOR Analyzer (Roche Molecular Systems, Inc., Pleasanton, Calif., U.S.A.), Mycycler and iCycler Thermal Cyclers (Bio-Rad Laboratories, Inc., Hercules, Calif., U.S.A.), and the SmartCycler System (Cepheid, Sunnyvale, Calif., U.S.A.), among many others. In other exemplary embodiments, sample preparation components, nucleic acid amplification components, and related fluid handling or material transfer components are integrated with the systems described herein, e.g., to fully automate a given nucleic acid amplification and analysis process. Instruments that can be adapted for this purpose include, for example, the m2000™ automated instrument system (Abbott Laboratories, Abbott Park, Ill., U.S.A.), the GeneXpert System (Cepheid, Sunnyvale, Calif. U.S.A.), and the COBAS® AmpliPrep® System (Roche Molecular Systems, Inc., Pleasanton, Calif., U.S.A.), and the like.

Figure 7A:
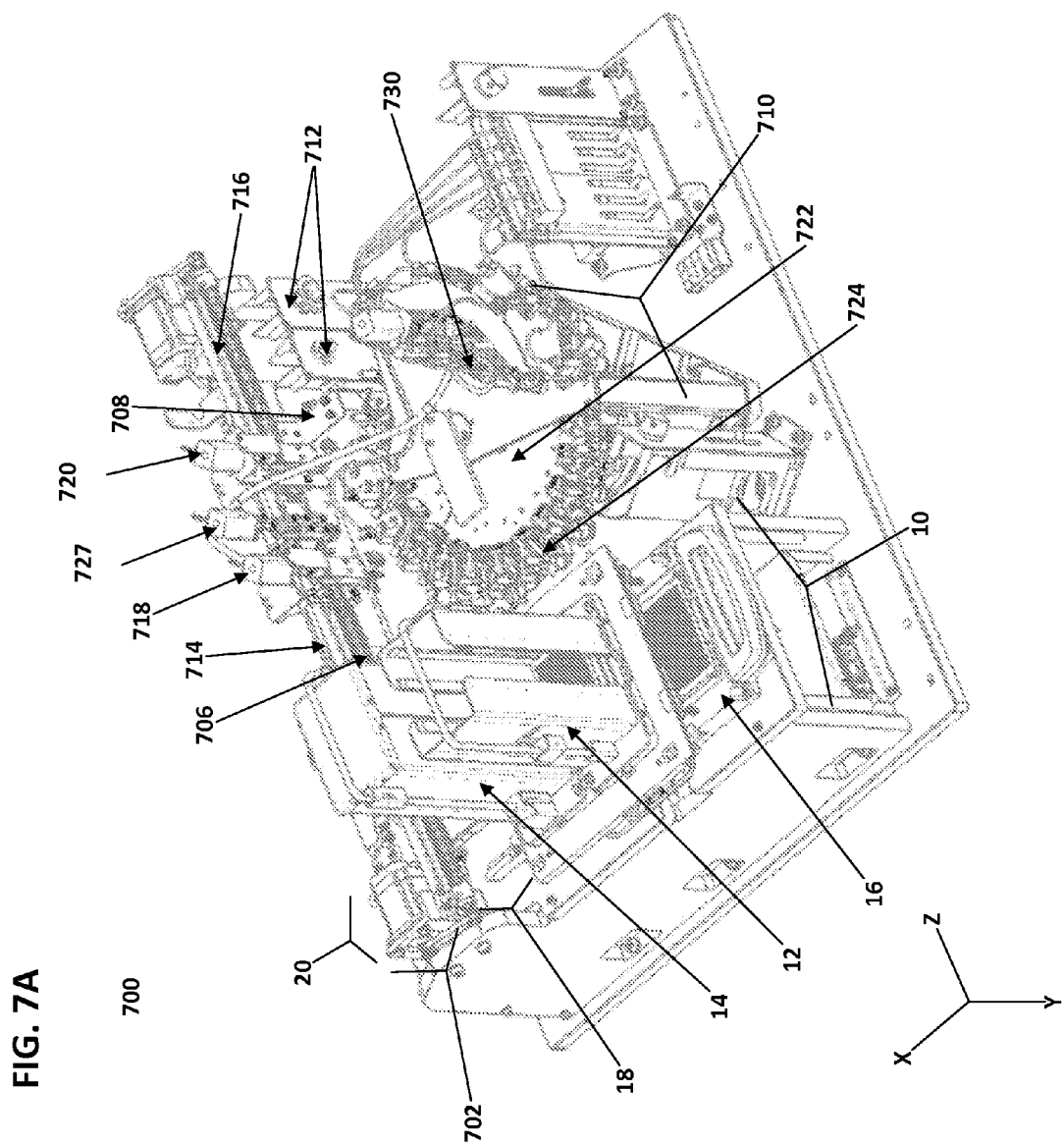
FIG. 7A schematically illustrates selected components of a representative system that includes a sample processing station as a sub-system component from a perspective view according to one embodiment of the invention.
Figure 7B:
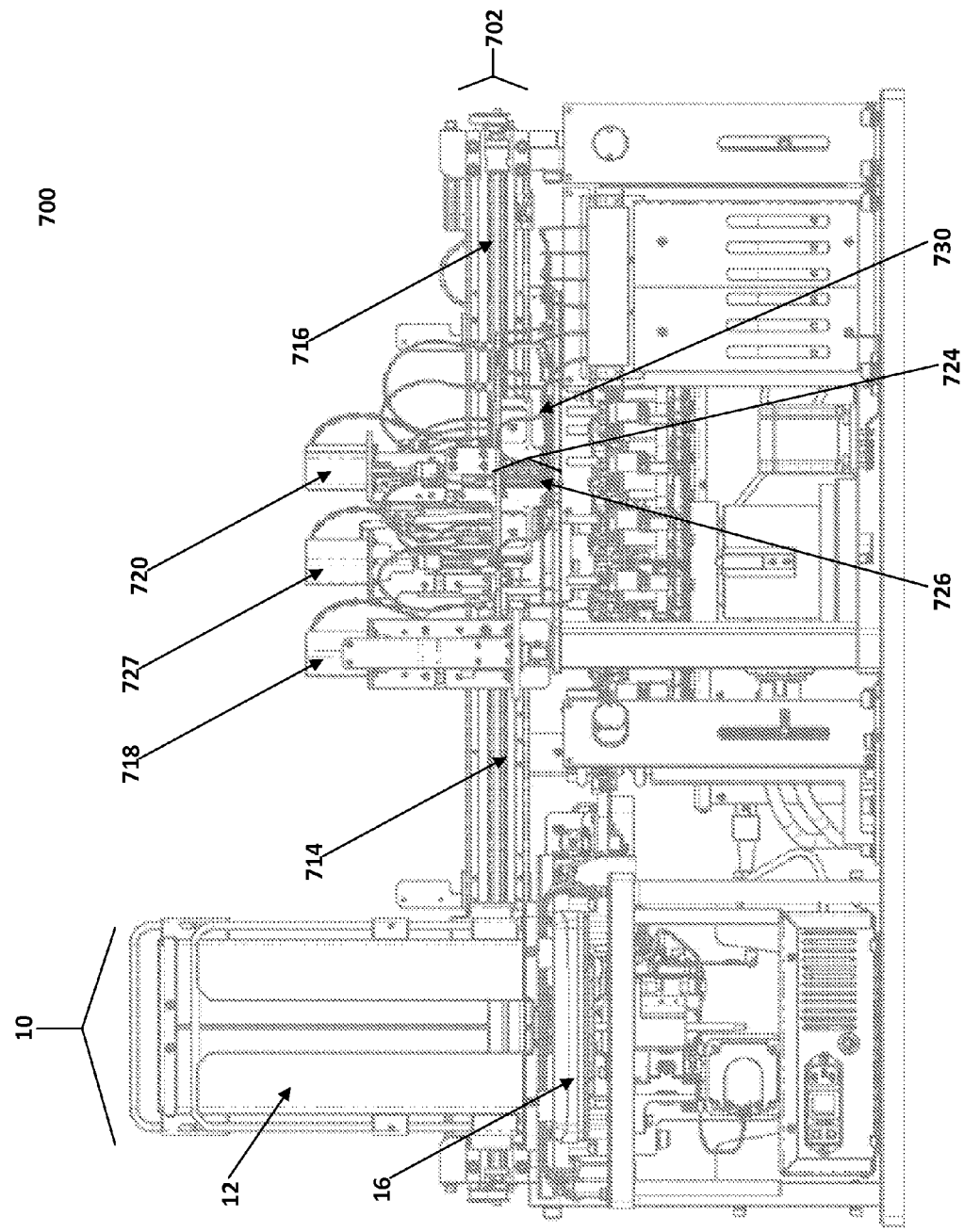
FIG. 7B schematically shows the representative system of FIG. 7A from a front elevation view.
Figure 7C:
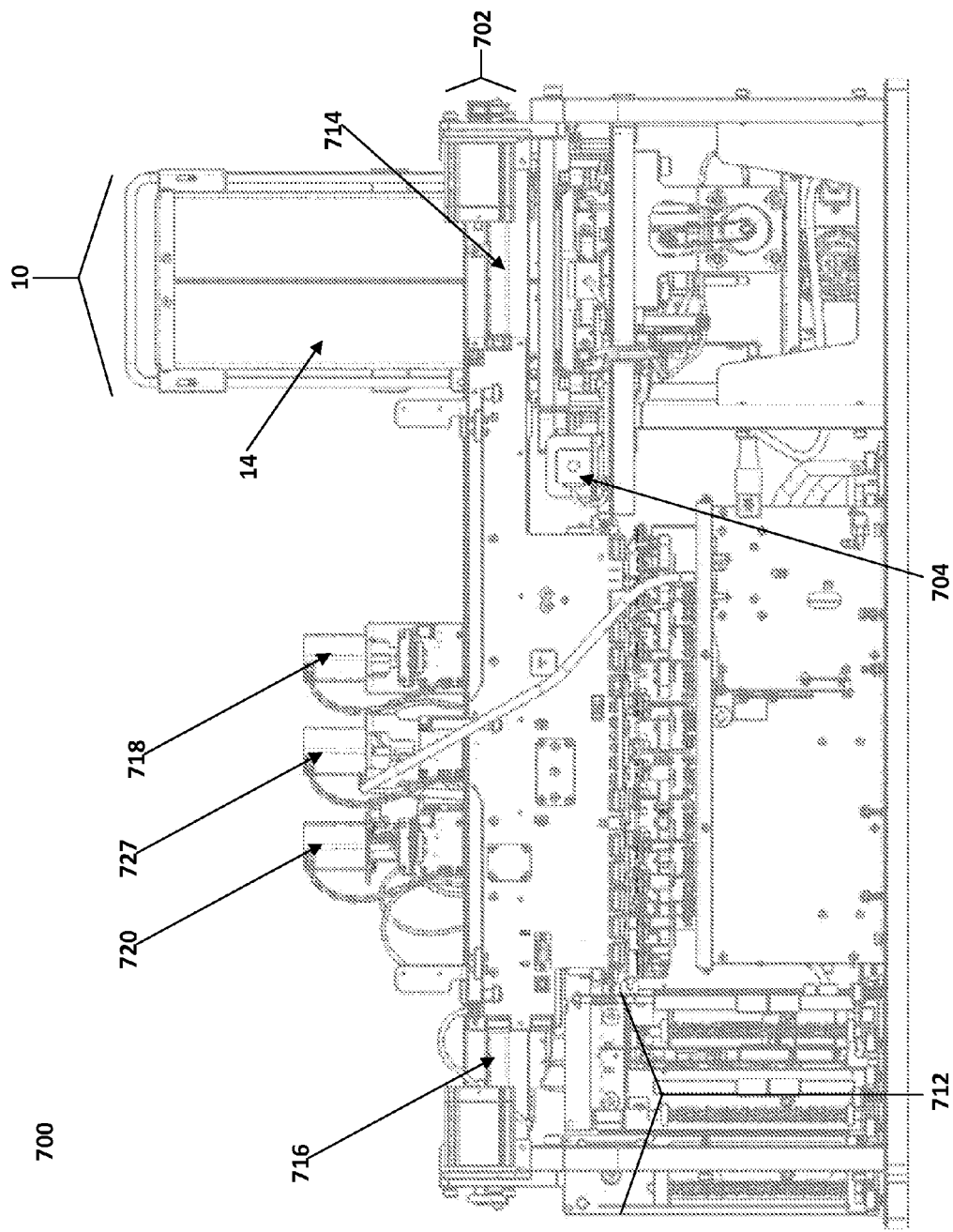
FIG. 7C schematically depicts the representative system of FIG. 7A from a rear elevation view.
Figure 7D:
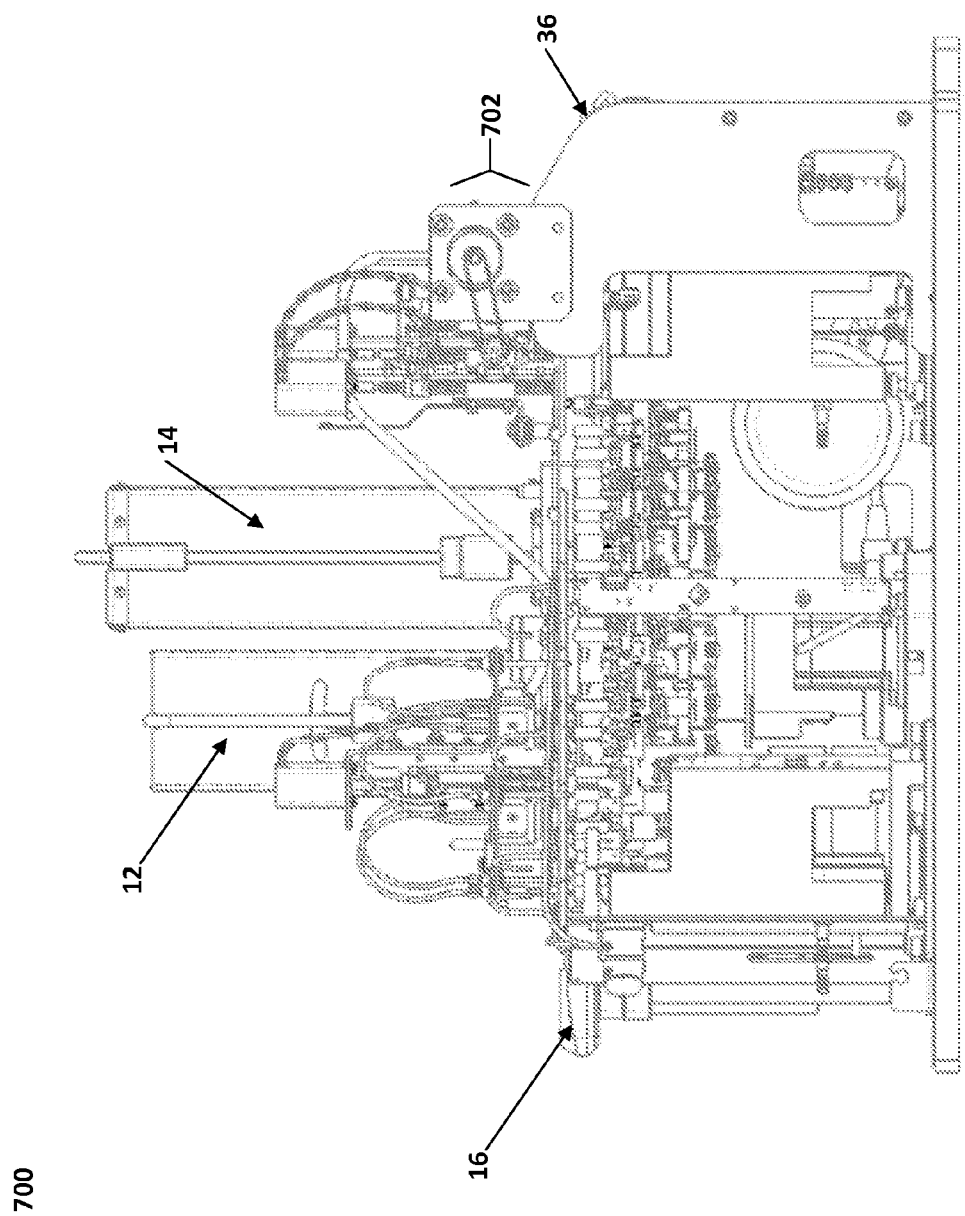
FIG. 7D schematically shows the representative system of FIG. 7A from a side elevation view.
Figure 7E:
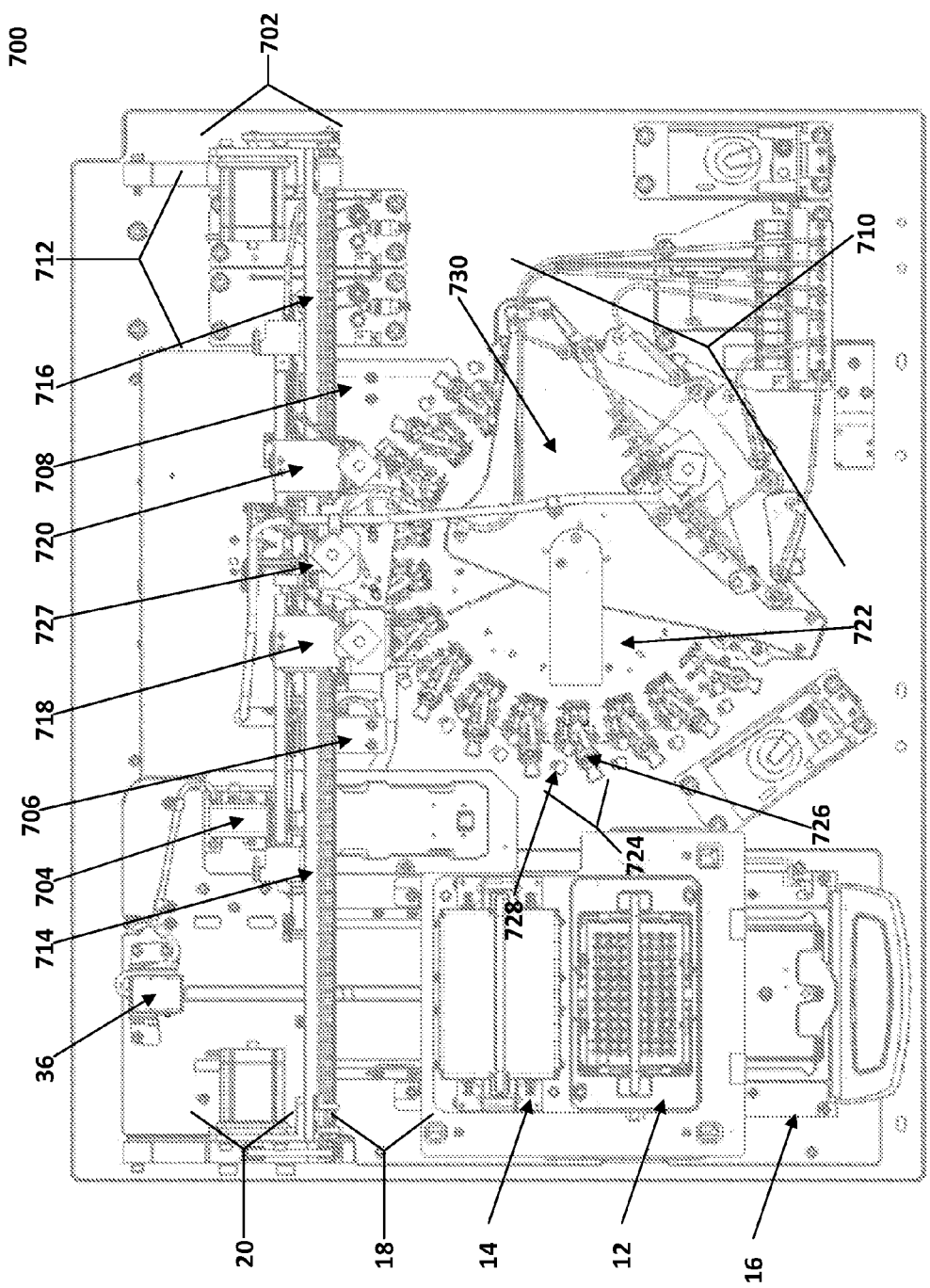
FIG. 7E schematically illustrates the representative system of FIG. 7A from a top elevation view.
Figure 7F:
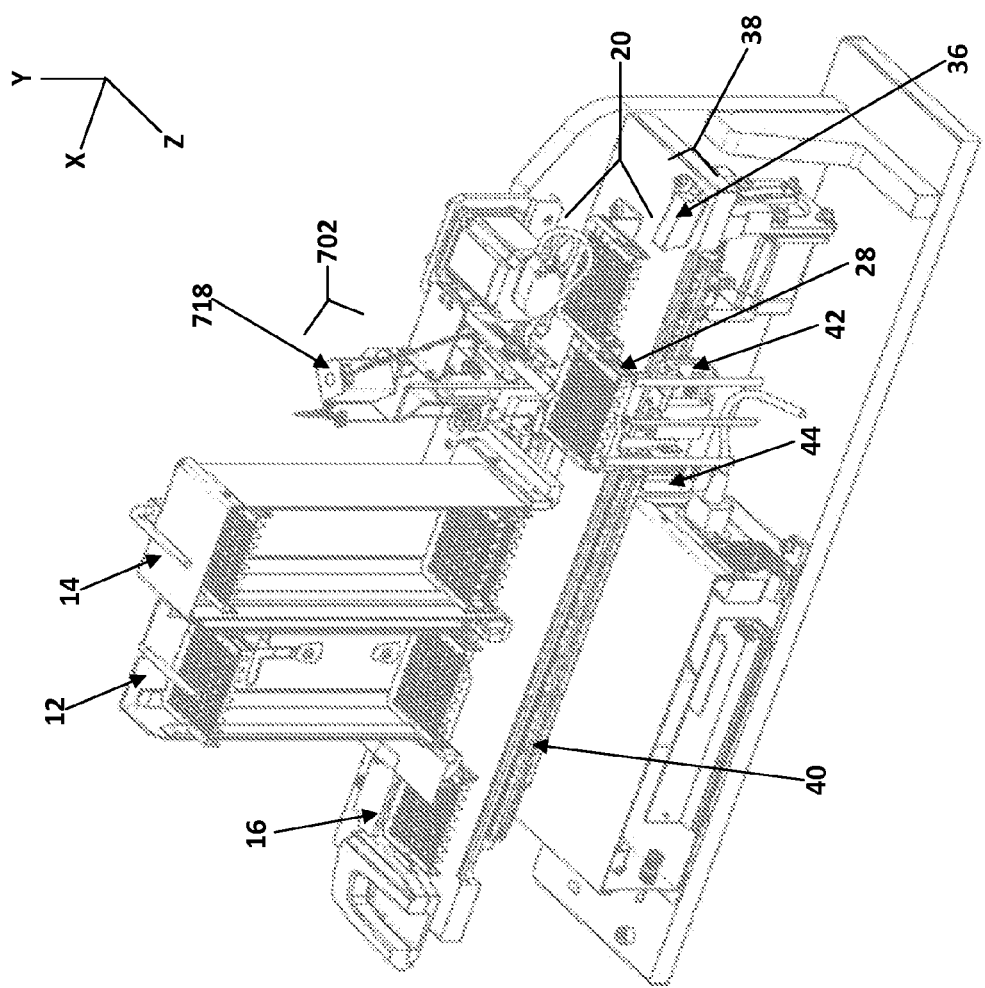
FIG. 7F schematically depicts the representative system of FIG. 7A from a cross-sectional view.
Figure 7G:
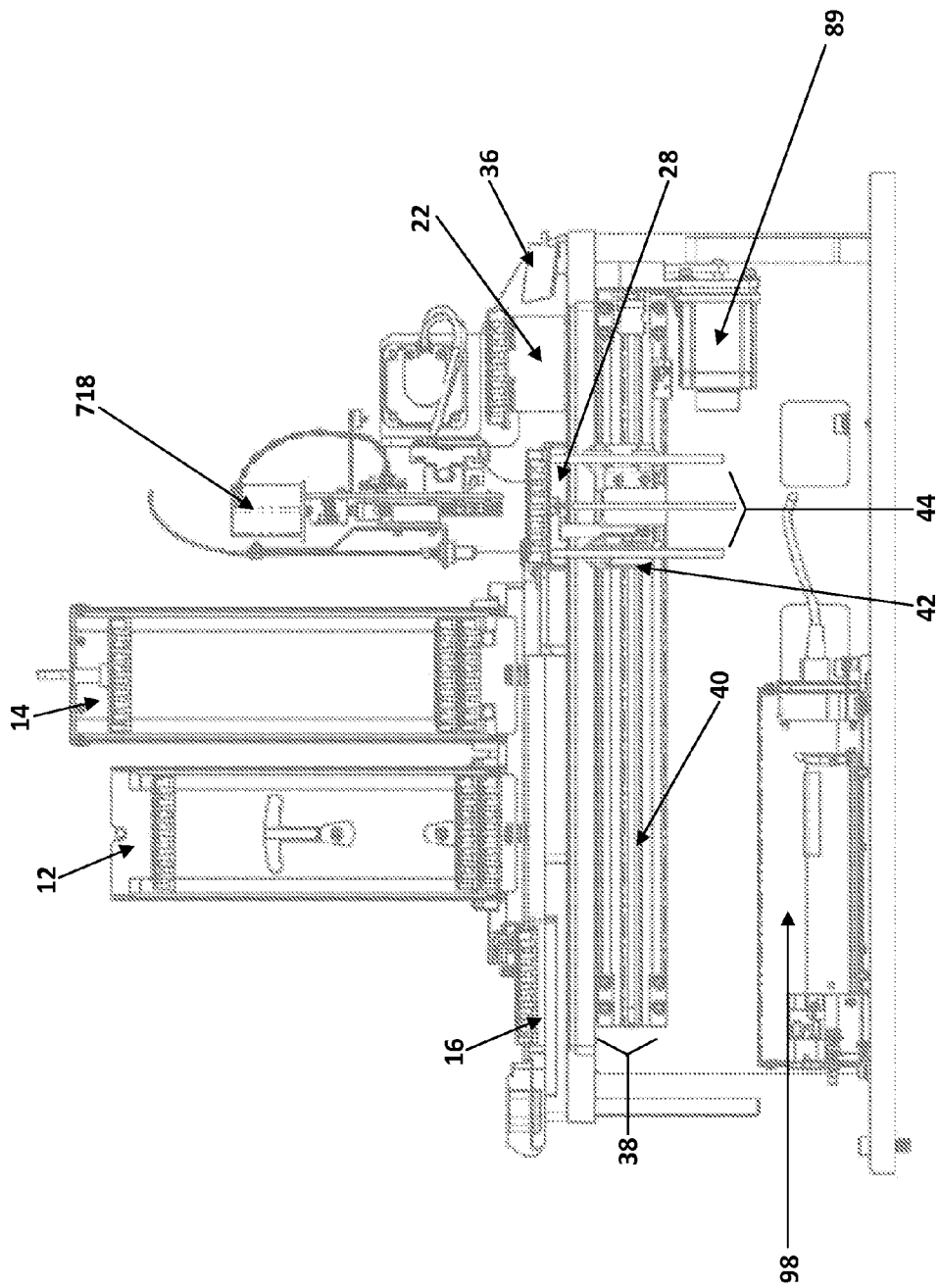
FIG. 7G schematically illustrates the representative system of FIG. 7A from a cross-sectional view.

Microplates are transferred from input non-priority microplate storage unit 12 or priority microplate storage unit 16 to microplate processing area 18 using platform 28 of a microplate transport mechanism. As referred to above and as shown in, e.g., FIGS. 7 F and G, platform 28 is operably connected to X-axis linear motion component 38. X-axis linear motion component 38 includes gantry 40. Platform 28 is operably connected to carriage 42, which moves along gantry 40, driven by motor 89. As further shown in FIGS. 7 F and G, microplate transport mechanism 26 also includes Y-axis linear motion component 44 operably connected to carriage 42 and to platform 28. Y-axis linear motion component 44 is configured to raise and lower platform 28 along the Y-axis. Suitable linear motion components, motors, and motor drives are generally available from many different commercial suppliers including, e.g., Techno-Isel Linear Motion Systems (New Hyde Park, N.Y., U.S.A.), NC Servo Technology Corp. (Westland, Mich., USA), Enprotech Automation Services (Ann Arbor, Mich., U.S.A.), Yaskawa Electric America, Inc. (Waukegan, Ill., U.S.A.), ISL Products International, Ltd. (Syosset, N.Y., U.S.A.), AMK Drives & Controls, Inc. (Richmond, Va., U.S.A.), Aerotech, Inc. (Pittsburgh, Pa., U.S.A.), HD Systems Inc. (Hauppauge, N.Y., U.S.A.), and the like. Additional detail relating to motors and motor drives are described in, e.g., Polka, Motors and Drives, ISA (2002) and Hendershot et al., Design of Brushless Permanent-Magnet Motors, Magna Physics Publishing (1994), which are both incorporated by reference. Microplate handling components are also described in, e.g., U.S. Provisional Patent Application No. 61/097,523, entitled "MICROPLATE HANDLING SYSTEMS AND RELATED COMPUTER PROGRAM PRODUCTS AND METHODS" filed Sep. 16, 2008 by Hofstadler et al., which is incorporated by reference in its entirety. FIG. 7G also shows power source 98, which provides power for the system shown in this figure.

Material transfer component 702 includes sample input gantry 714 and sample output gantry 716. Input gantry head 718 is configured to move along sample input gantry 714, whereas output gantry head 720 is configured to move along sample output gantry 716. Input gantry head 718 and output gantry head 720 each include needles that are configured to aspirate and dispense fluidic materials. Further, input gantry head 718 and output gantry head 720 are each configured to be raised and lowered along the Y-axis. During operation of exemplary system 700, the needle or pipetting tip of input gantry head 718 is typically used to aspirate an aliquot of magnetically responsive particles (e.g., magnetically responsive beads, such as BioMag®Plus Amine superparamagnetic microparticles available from Bangs Laboratories, Inc., Fishers, Ind., U.S.A.) that bind nucleic acids from a mixing cartridge positioned at mixing station 704. Magnetically responsive particle sources and mixing stations are also described in, e.g., U.S. Provisional Patent Application No. 61/097,520, entitled "MIXING CARTRIDGES, MIXING STATIONS, AND RELATED KITS, SYSTEMS, AND METHODS" filed Sep. 16, 2008 by Hofstadler et al., which is incorporated by reference in its entirety. Nucleic acid purification involving magnetically responsive particles is also described in, e.g., U.S. Patent App. Pub. No. US 2005/0164215, entitled "METHOD FOR RAPID PURIFICATION OF NUCLEIC ACIDS FOR SUBSEQUENT ANALYSIS BY MASS SPECTROMETRY BY SOLUTION CAPTURE," filed May 12, 2004 by Hofstadler et al., and U.S. Patent App. Pub. No. US 2005/0130196, entitled "METHOD FOR RAPID PURIFICATION OF NUCLEIC ACIDS FOR SUBSEQUENT ANALYSIS BY MASS SPECTROMETRY BY SOLUTION CAPTURE," filed Sep. 17, 2004 by Hofstadler et al., which are both incorporated by reference in their entirety. Optionally before, but typically after aspirating the aliquot of magnetically responsive particles (e.g., to minimize the possibility of cross-contaminating samples), the needle of input gantry head 718 is also generally used to aspirate an aliquot of an amplification product sample from a selected well of a microplate positioned in microplate processing area 18 of microplate handling system 10. The resulting mixture of magnetically responsive particle and amplification product sample aliquots disposed within the needle of input gantry head 718 is then typically transferred to sample processing component 710 along sample input gantry 714. After dispensing the mixture at sample processing component 710, the needle of input gantry head 718 is typically washed at wash station 706, e.g., to minimize the probability of cross-contaminating samples, prior to repeating this transfer cycle for other amplification product samples contained in the wells of a given microplate (e.g., priority or non-priority microplates) positioned in microplate processing area 18 of microplate handling system 10.

In the embodiment shown, sample processing station or component 710 is a desalting station that is used to desalt or otherwise purify nucleic acid amplification products in the sample mixture prior to mass spectrometric analysis. Sample processing component 710 includes carrier mechanism 722 (shown as a carousel), which includes a plurality of sample processing units 724. In the illustrated embodiment, each sample processing unit 724 includes cuvette 726 and magnet 728. After a mixture of magnetically responsive particle and amplification product sample aliquots is dispensed into a given cuvette 726, that cuvette is typically rotated in a counter-clockwise direction on carrier mechanism 722 to various positions within sample processing component 710 where various reagents (e.g., washes with ammonium bicarbonate and/or MeOH, etc.) are added to and/or removed from that cuvette (e.g., via various fluidic handling components of manifold 730) as part of the process of purifying the amplification products captured or otherwise bound to the magnetically responsive particles in the mixture. When fluidic materials are removed from the cuvette at a given position within sample processing component 710, the cuvette is typically moved proximal to the magnet of the particular sample processing unit (e.g., cuvette 726 is moved proximal to magnet 728 of sample processing unit 724) using a conveyance mechanism to establish sufficient magnetic communication between the magnet and the magnetically responsive particles such that the magnetically responsive particles are moved to and retained on an internal surface of the cuvette while fluidic materials are removed from the cuvette. At the conclusion of a purification process for a given sample, the purified amplification products are then typically aspirated from the particular cuvette using the needle of output gantry head 720. During or prior this step, the nucleic acid amplification products are eluted (e.g., using a solution that includes piperidine, imidazole, MeOH, and optionally peptide calibration standards (used as part of subsequent mass spectrometric analyses), or the like) from the magnetically responsive particles. After purified amplification products have been removed from a given cuvette, that cuvette is then generally rotated on carrier mechanism 722 into communication with cuvette wash station 727, where the cuvette is washed prior to commencing another purification cycle involving the cuvette and another sample. Sample desalting/purification methods are also described in, e.g., U.S. Patent App. Pub. No. US 2005/0164215, entitled "METHOD FOR RAPID PURIFICATION OF NUCLEIC ACIDS FOR SUBSEQUENT ANALYSIS BY MASS SPECTROMETRY BY SOLUTION CAPTURE," filed May 12, 2004 by Hofstadler et al., and U.S. Patent App. Pub. No. US 2005/0130196, entitled "METHOD FOR RAPID PURIFICATION OF NUCLEIC ACIDS FOR SUB- SEQUENT ANALYSIS BY MASS SPECTROMETRY BY SOLUTION CAPTURE," filed Sep. 17, 2004 by Hofstadler et al., and Hofstadler et al. (2003) "A highly efficient and automated method of purifying and desalting PCR products for analysis by electrospray ionization mass spectrometry" *Anal Biochem.* 316:50-57, which are each incorporated by reference in their entirety.

Purified and eluted amplification products that have been aspirated from a particular cuvette of sample processing component 710 are typically transported along sample output gantry 716 to sample injector 712 (shown as a two channel time-of-flight injector) using output gantry head 720. That is, the amplification products are typically dispensed from the needle or pipetting tip of output gantry head 720 into one of the two channels of sample injector 712, which generally comprise two independent sample injection syringe pumps that are configured to receive the amplification products. After dispensing the amplification products at sample injector 712, the needle of output gantry head 720 is typically washed at wash station 708 prior to aspirating another purified amplification product sample from sample processing component 710, e.g., to reduce the potential for carryover contamination between samples.

Figure 8A:
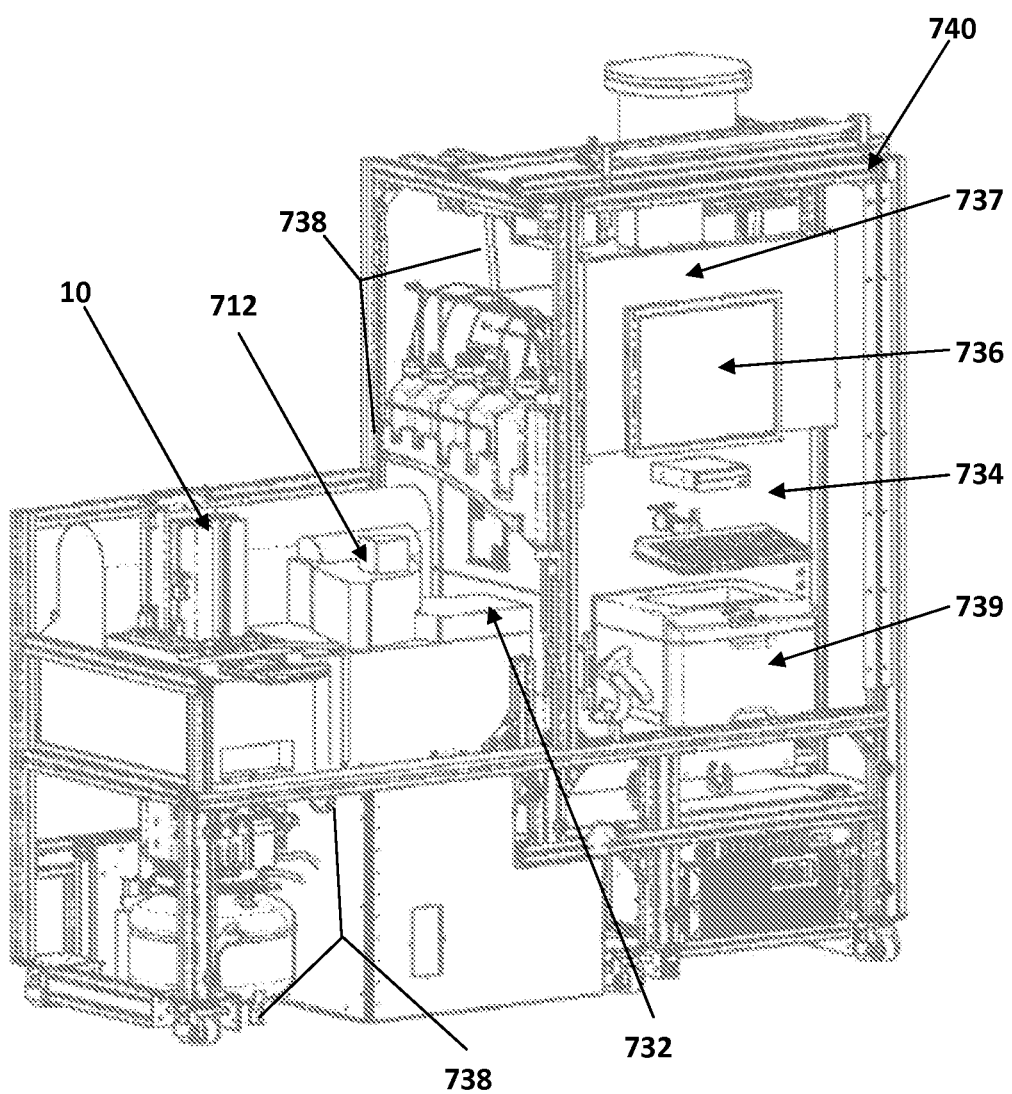
FIG. 8A and FIG. 8B schematically show additional components of a representative system of FIG. 7A from a perspective view.
Figure 8B:
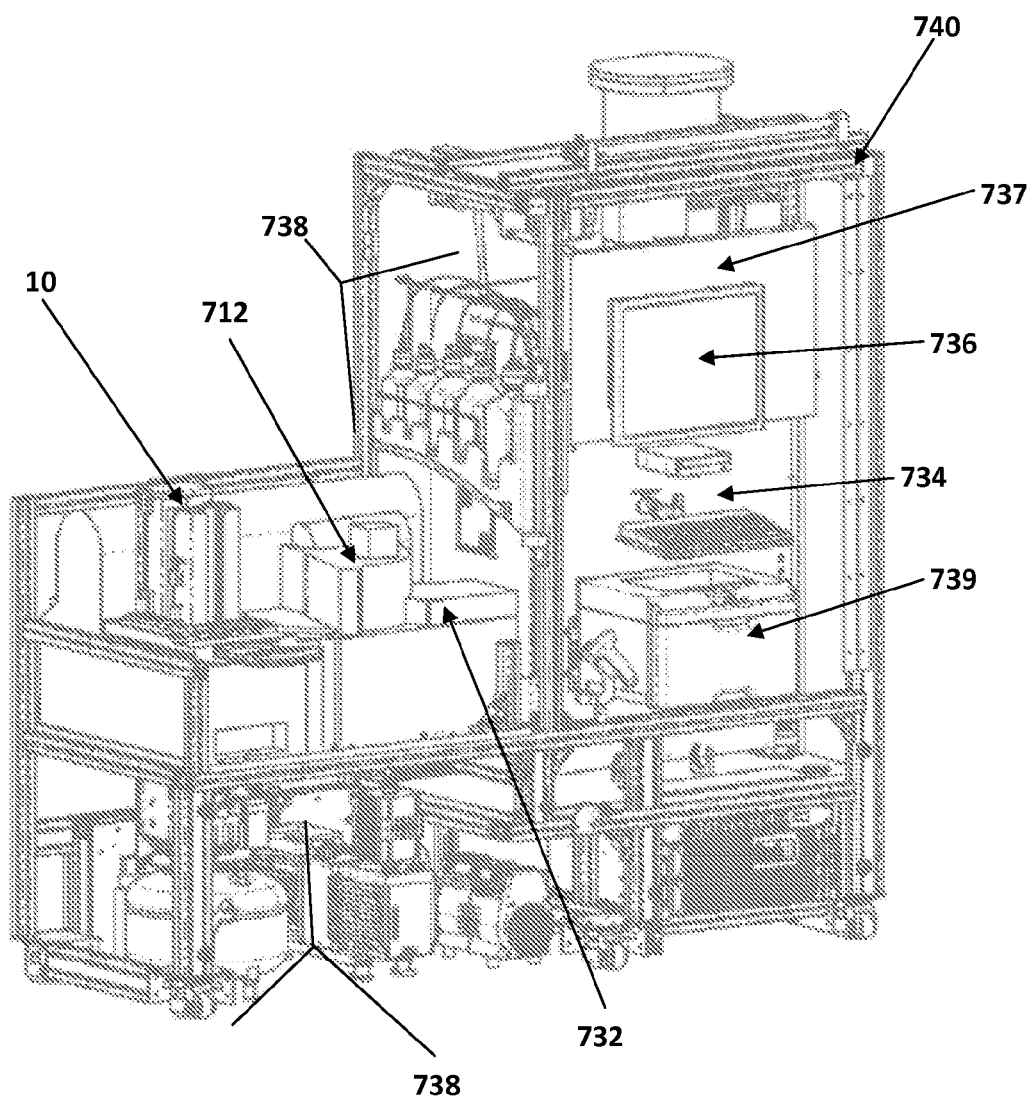
Figure 9A:
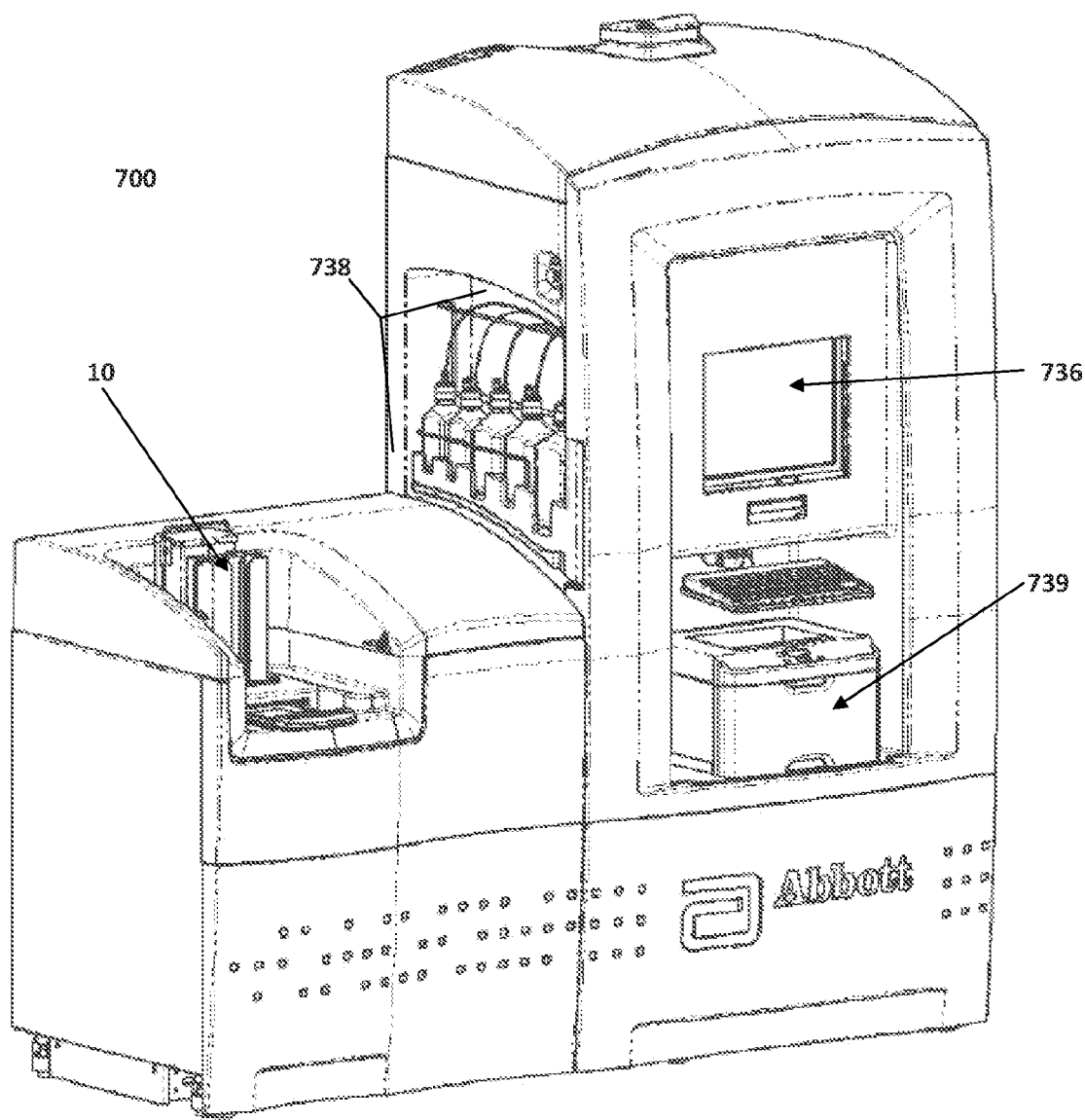
FIG. 9A schematically illustrates the representative system of FIG. 7A with an external covering from a perspective view.
Figure 9B:
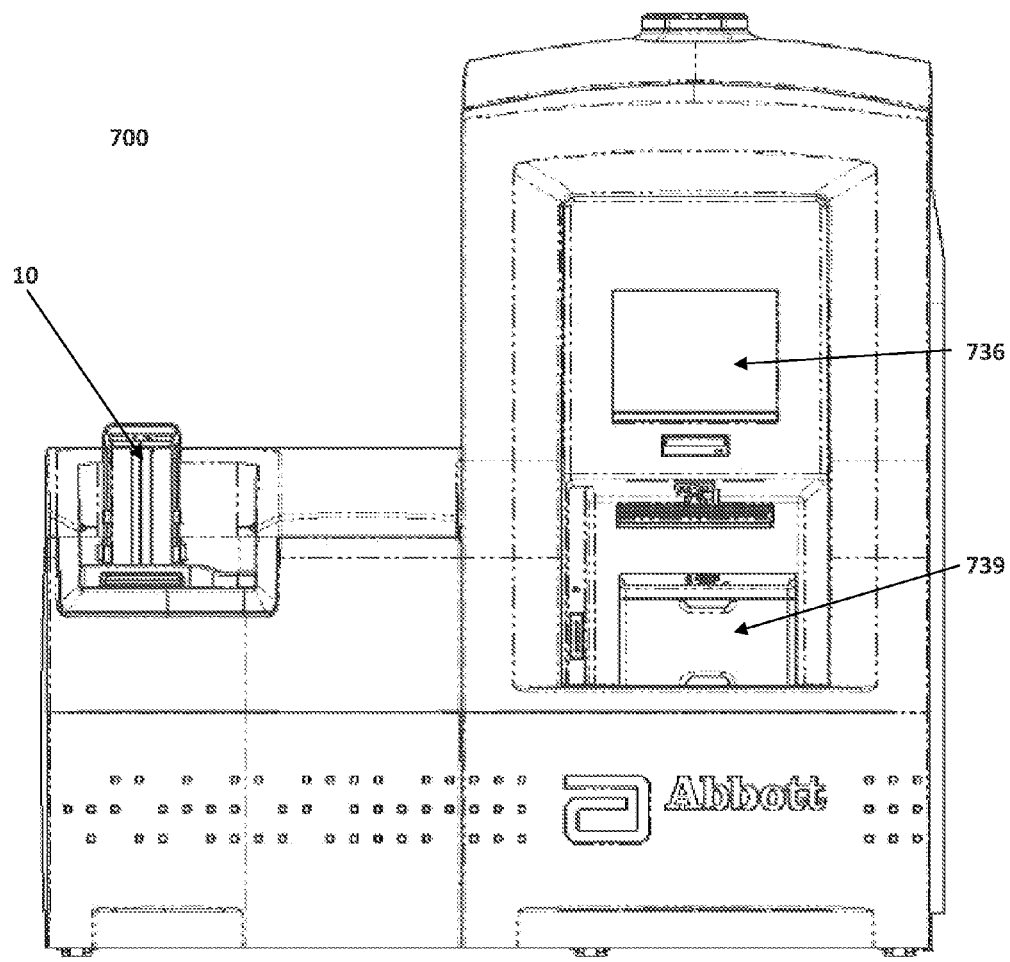
FIG. 9B schematically illustrates the representative system of FIG. 7A with an external covering from a front elevation view.
Figure 9C:
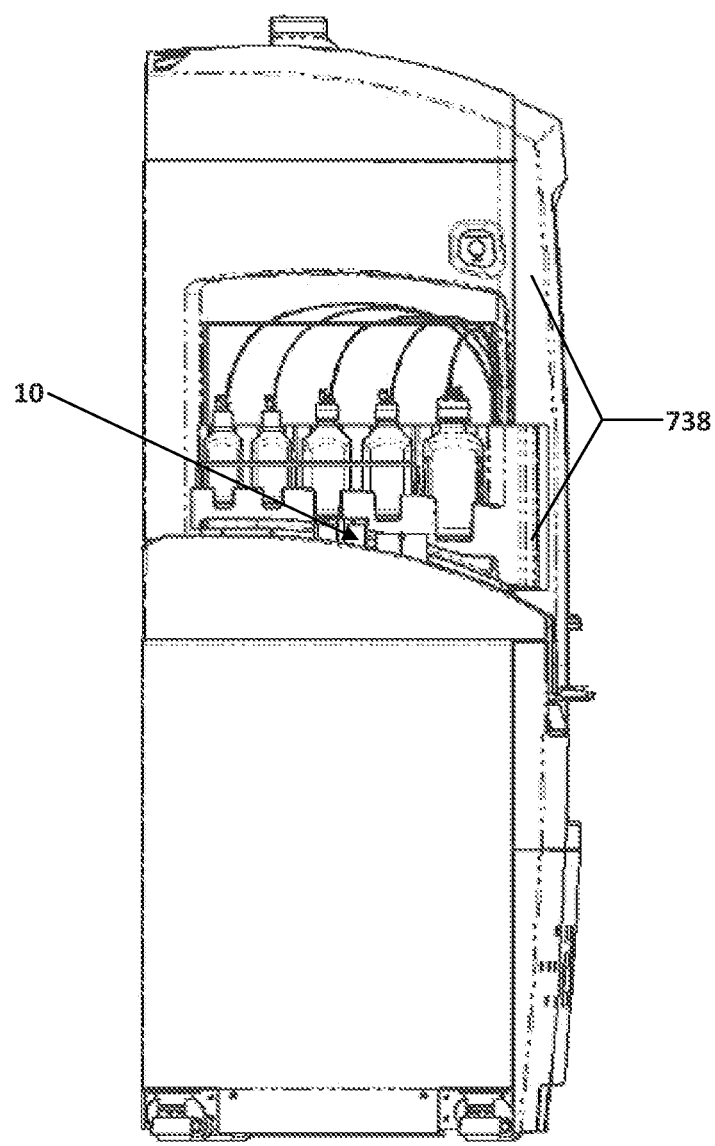
FIG. 9C schematically shows the representative system of FIG. 7A with an external covering from a side view.

Now referring to FIG. 8, which schematically shows additional components of representative system 700 (sample processing component 710 is not shown so that other system components are within view) from a perspective view. As shown, the additional components include dual sprayer module 732, which includes two independent electrospray ionization sprayers, and time-of-flight mass spectrometer 734. Amplification product samples received at sample injector 712 are typically injected into one of the two sprayers of dual sprayer module 732 for electrospray ionization and mass measurement in time-of-flight mass spectrometer 734. As further shown, the additional components of representative system 700 also include input/output device 736 (shown as a touch screen monitor), computer 737, output device 739 (shown as a printer), reagent and/or waste modules 738, and chassis 740. Input/output device 736, computer 737, and output device 739 are components of a controller of system 700. Controllers are described further herein. Reagent module 738 provides reagent sources, and the waste module 738 provides waste receptacles for system 700. Chassis 740 provides mechanical support for microplate handling system 10, sample processing component 710, and other components of system 700. To further illustrate, FIGS. 11A-C schematically show representative system 700 with an external covering from various views.

In some embodiments, the base compositions of amplification products are determined from detected molecular masses. In these embodiments, base compositions are typically correlated with the identity of an organismal source, genotype, or other attribute of the corresponding template nucleic acids in a given sample. Suitable software and related aspects, e.g., for determining base compositions from detected molecular masses and for performing other aspects of base composition analysis are commercially available from Ibis Biosciences, Inc. (Carlsbad, Calif., U.S.A.). Nucleic acid base composition analysis is also described in many of the publications referred to herein, including, e.g., U.S. Pat. No. 7,255,992, entitled "METHODS FOR RAPID DETECTION AND IDENTIFICATION OF BIOAGENTS FOR ENVIRONMENTAL AND PRODUCT TESTING," which issued Aug. 14, 2007 to Ecker et al., U.S. Pat. No. 7,226,739, entitled "METHODS FOR RAPID DETECTION AND IDENTIFICATION OF BIOAGENTS IN EPIDEMIOLOGICAL AND FORENSIC INVESTIGATIONS," which issued Jun. 5, 2007 to Ecker et al., U.S. Pat. No. 7,217,510, entitled "METHODS FOR PROVIDING BACTERIAL BIOAGENT CHARACTERIZING INFORMATION," which issued May 15, 2007 to Ecker et al., and U.S. Pat. No. 7,108,974, entitled "METHOD FOR RAPID DETECTION AND IDENTIFICATION OF BIOAGENTS," which issued Sep. 19, 2006 to Ecker et al., which are each incorporated by reference in their entirety.

VI. Fabrication Methods and Materials

Sample processing units or components thereof, carrier mechanisms or components thereof, and station or system components (e.g., mixing stations, microplate storage units, microplate transport mechanisms, support bases, etc.) are optionally formed by various fabrication techniques or combinations of such techniques including, e.g., machining, embossing, extrusion, stamping, engraving, injection molding, cast molding, etching (e.g., electrochemical etching, etc.), or other techniques. These and other suitable fabrication techniques are generally known in the art and described in, e.g., Molinari et al. (Eds.), Metal Cutting and High Speed Machining, Kluwer Academic Publishers (2002), Altintas, Manufacturing Automation: Metal Cutting Mechanics, Machine Tool Vibrations, and CNC Design, Cambridge University Press (2000), Stephenson et al., Metal Cutting Theory and Practice, Marcel Dekker (1997), Fundamentals of Injection Molding, W. J. T. Associates (2000), Whelan, Injection Molding of Thermoplastics Materials, Vol. 2, Chapman & Hall (1991), Rosato, Injection Molding Handbook, $3^{rd}$ Ed., Kluwer Academic Publishers (2000), Fisher, Extrusion of Plastics, Halsted Press (1976), and Chung, Extrusion of Polymers: Theory and Practice, Hanser-Gardner Publications (2000), which are each incorporated by reference. Exemplary materials optionally used to fabricate sample processing units, carrier mechanisms, manifolds, or components thereof include metal (e.g., steel, aluminum, etc.), glass, polymethylmethacrylate, polyethylene, polydimethylsiloxane, polyetheretherketone, polytetrafluoroethylene, polystyrene, polyvinylchloride, polypropylene, polysulfone, polymethylpentene, and polycarbonate, among many others. In certain embodiments, following fabrication, system components are optionally further processed, e.g., by coating surfaces with a hydrophilic coating, a hydrophobic coating (e.g., a Xylan 1010DF/870 Black coating available from Whitford Corporation (West Chester, Pa.), etc.), or the like, e.g., to prevent interactions between component surfaces and reagents, samples, or the like.

VII. Examples

It is understood that the examples and embodiments described herein are for illustrative purposes only and are not intended to limit the scope of the claimed invention. It is also understood that various modifications or changes in light the examples and embodiments described herein will be suggested to persons skilled in the art and are to be included within the spirit and purview of this application and scope of the appended claims.

I. PCR Product Purification and Desalting Example

1. PCR Product Purification

PCR products were thoroughly purified and desalted before ESI MS. This step typically precedes ESI-MS analysis, because PCR salts and buffer components generally have a deleterious effect on the ESI process. Even small amounts of salts (<1 µmol/L) will typically significantly reduce ESI sensitivity, owing to the appearance of multiple cation adducts in the mass spectra. The protocol used in this example is based on a weak anion-exchange method, in which amplified DNA was bound to a weak anion-exchange resin coated on the outside of magnetic bead particles. Unconsumed deoxy-nucleoside triphosphates, salts, and other low-molecular-weight species that could interfere with subsequent ESI-MS analysis were removed using a sample processing station system described herein and the PCR cleanup process outlined as follows:
1. Loaded 40 µL PCR Product and 50 µL magnetic bead solution into a clean cuvette;
2. Mixed the beads for 4.5 minutes to allow the DNA to bind the magnetic beads;
3. Positioned the cuvette at the magnet for 30 seconds to separate the beads from the solution;
4. Aspirated the liquid from the cuvette and dispensed 80 µL of 100 mM ammonium bicarbonate in a 50:50 methanol: water solution;
5. Resuspended and washed the beads by mixing for 35 seconds;
6. Positioned the cuvette at the magnet for 15 seconds to separate the beads from the solution;
7. Aspirated the liquid from the cuvette and dispensed 80 µL of 100 mM ammonium bicarbonate in a 50:50 methanol: water solution;
8. Resuspended and washed the beads by mixing for 35 seconds;
9. Positioned the cuvette at the magnet for 15 seconds to separate the beads from the solution;
10. Aspirated the liquid from the cuvette and dispensed 80 µL of 50:50 methanol:water solution;
11. Resuspended and washed the beads by mixing for 35 seconds;
12. Positioned the cuvette at the magnet for 15 seconds to separate the beads from the solution;
13. Aspirated the liquid from the cuvette and dispensed 40 µL of 25 mM piperidine and 25 mM imidazole in 35:65 methanol:water solution;
14. Resuspended the magnetic beads and allowed time for the DNA to elute from the beads for 2 minutes;
15. Positioned the cuvette at the magnet for 30 seconds to separate the beads from the solution; and
16. Aspirated the solution and injected into the ESI-MS for analysis.

TOTAL PCR PRODUCT CLEANUP TIME=10 minutes

II. 2. Cuvette Cleaning Protocol

The cuvette cleaning protocol utilized to clean the cuvette after PCR products were purified and desalted was as follows:
1. Dispensed 160 µL of 25 mM piperidine and 25 mM imidazole in 35:65 methanol:water solution and mixed for 15 seconds;
2. Aspirated solution and dispensed 160 µL of clean (Type I) water into the cuvette;
3. Mixed for 15 seconds; and
4. Aspirated liquid from cuvette.

TOTAL CUVETTE CLEANUP TIME=2 minutes

II. 3. ESI-TOF Mass Spectrometry

Figure 2:
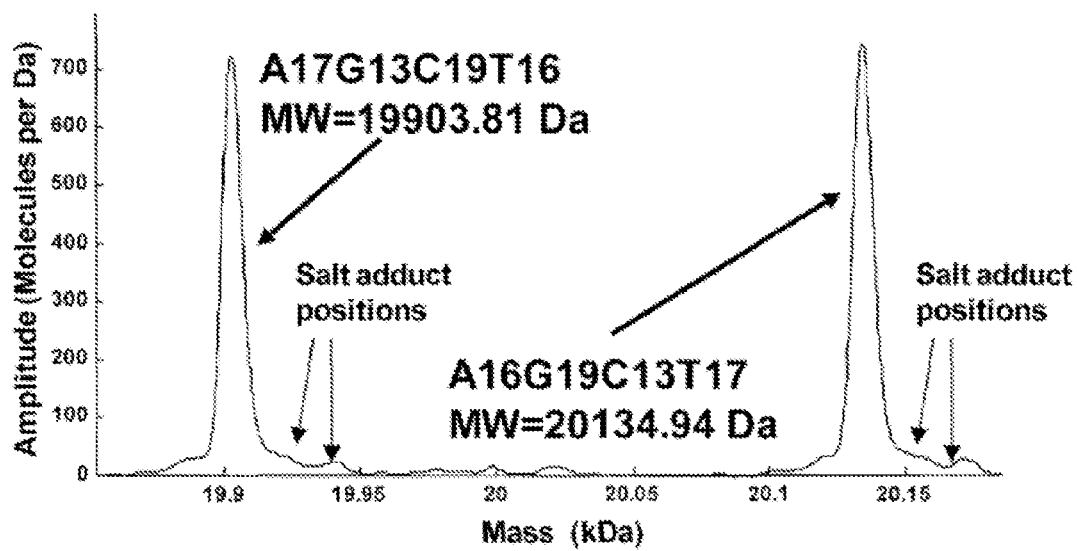
FIG. 2 is a mass spectrum obtained for a 65-mer PCR product following a purification and desalting protocol described herein. The two peaks correspond to sense and antisense strands of the PCR amplicons, which separate under the conditions of ESI. Low amplitude salt adducts indicated effective cleanup of the PCR product.

A Bruker Daltonics (Billerica, Mass., U.S.A.) MicroTOF-ESI time-of-flight (TOF) mass spectrometer was used to analyze purified and desalted PCR products in this example. Ions from the ESI source underwent orthogonal ion extraction and were focused in a reflectron prior to detection. Ions were formed in the standard MicroTOF-ESI source, which was equipped with an off-axis sprayer and glass capillary. For operation in the negative ion mode, the atmospheric pressure end of the glass capillary was biased at 3500 V relative to the ESI needle during data acquisition. A countercurrent flow of dry $N_2$ gas was employed to assist in the desolvation process. External ion accumulation was employed to improve ionization duty cycle during data acquisition and to enhance sensitivity in the m/z range of interest. In this example, each 75 µs scan was comprised of 75,000 data points (a 37.5 µs delay followed by a 37.5 µs digitization event at 2 GHz). For each spectrum, 660 000 scans were co-added. Example data obtained from this analysis is shown in FIG. 2.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

We claim:

1. A sample processing unit, comprising:
    at least one sample comprising at least one magnetically responsive particle;
    at least one magnet that generates, or is configured to generate, at least one magnetic field, which magnet is in a substantially fixed position relative to the sample;
    at least one conveyance mechanism configured to convey the sample between at least first and second positions, wherein at least the first position is within magnetic communication with the magnet when the magnet generates the magnetic field; and,
    at least one rotational mechanism, which rotational mechanism is configured to rotate the sample when the sample is in at least the second position.

2. The sample processing unit of claim 1, wherein the magnet comprises a permanent magnet.

3. The sample processing unit of claim 1, wherein the magnet comprises an electromagnet.

4. The sample processing unit of claim 1, wherein the conveyance mechanism comprises at least one motor.

5. The sample processing unit of claim 4, wherein at least one motor comprises a stepper motor.

6. The sample processing unit of claim 4, wherein at least one motor comprises a brushless direct current motor.

7. The sample processing unit of claim 1, wherein the conveyance mechanism is configured to rotate the sample between the first and second positions.

8. The sample processing unit of claim 1, wherein the conveyance mechanism is configured to slide the sample between the first and second positions.

9. The sample processing unit of claim 1, wherein the rotational mechanism is configured to rotate the sample in at least one oscillating motion.

10. The sample processing unit of claim 1, comprising at least one mounting bracket that is operably connected to one or more of: the magnet, the conveyance mechanism, or the rotational mechanism.

11. the sample processing unit of claim 1, comprising a desalting station, a sample wash station, a fluid transfer station, or a mixing station.

12. The sample processing unit of claim 1, comprising at least one wash reagent.

13. The sample processing unit of claim 1, comprising at least one elution reagent.

14. The sample processing unit of claim 1, wherein the magnetically responsive particle comprises an anion exchange resin.

15. The sample processing unit of claim 14, wherein the magnetically responsive particle comprises at least one biopolymer capture reagent.

16. The sample processing unit of claim 15, wherein the biopolymer capture reagent comprises at least one anion exchange functional group.

17. The sample processing unit of claim 16, wherein the anion exchange functional group comprises a $pK_a$ value of 9.0 or greater.

18. The sample processing unit of claim 16, wherein the anion exchange functional group is selected from the group consisting of a primary amine, a second amine, a tertiary amine, a quaternary amine, a polyethyleneimine, a charged aromatic amine, a diethylaminomethyl, and a diethylaminoethyl.

19. The sample processing unit of claim 1, wherein the sample processing unit comprises a controller comprising a programmed processor, a computer, a digital device, a logic device or an information appliance.

* * * * *